US008802099B2

(12) United States Patent
Gelfand et al.

(10) Patent No.: US 8,802,099 B2
(45) Date of Patent: Aug. 12, 2014

(54) METHODS TO TREAT ALLERGIC CONDITIONS

(75) Inventors: Erwin W. Gelfand, Englewood, CO (US); Meiqin Wang, Glendale, CO (US)

(73) Assignee: National Jewish Health, Denver, CO (US)

(*) Notice: Subject to any disclaimer, the term of this patent is extended or adjusted under 35 U.S.C. 154(b) by 0 days.

(21) Appl. No.: 13/293,911

(22) Filed: Nov. 10, 2011

(65) Prior Publication Data
US 2012/0114663 A1   May 10, 2012

Related U.S. Application Data

(60) Provisional application No. 61/412,194, filed on Nov. 10, 2010.

(51) Int. Cl.
| A61K 39/395 | (2006.01) |
| A61K 38/00 | (2006.01) |
| A61K 38/46 | (2006.01) |
| A61K 31/405 | (2006.01) |
| A61K 31/00 | (2006.01) |
| A61K 31/70 | (2006.01) |
| A01N 43/38 | (2006.01) |
| A01N 43/00 | (2006.01) |
| A01N 43/04 | (2006.01) |
| A61K 31/7052 | (2006.01) |
| A61K 31/553 | (2006.01) |
| A61K 31/4045 | (2006.01) |

(52) U.S. Cl.
CPC ............ *A61K 31/553* (2013.01); *A61K 31/7052* (2013.01); *A61K 31/00* (2013.01); *A61K 31/4045* (2013.01)
USPC ........... 424/158.1; 424/172.1; 424/94.5; 424/94.6; 514/1.1; 514/52; 514/211.08; 514/415

(58) Field of Classification Search
CPC ..... A61K 38/00; A61K 38/46; A61K 39/395; A61K 39/31; A61K 39/405; A61K 31/00; A61K 31/70; A01N 43/38; A01N 43/43; A01N 43/04
USPC .......... 424/158.1, 172.1, 94.5, 94.6; 514/415, 514/52, 1.1, 211.08
See application file for complete search history.

(56) References Cited

U.S. PATENT DOCUMENTS

| 2004/0142864 A1* | 7/2004 | Bremer et al. ................ 514/12 |
| 2007/0299049 A1* | 12/2007 | Coutre ..................... 514/211.08 |

FOREIGN PATENT DOCUMENTS

| WO | WO 00/62781 | 10/2000 |
| WO | WO 2004/058042 | 7/2004 |
| WO | WO 2004/058749 | 7/2004 |
| WO | WO 2004058749 A1 * | 7/2004 |
| WO | WO 2006/002422 | 1/2006 |

OTHER PUBLICATIONS

Shin et al., (J Allergy Clin Immun. Feb. 1, 2010. 125(3):AB63, #247).*

(Continued)

*Primary Examiner* — Cherie M Stanfield
(74) *Attorney, Agent, or Firm* — Sheridan Ross P.C.

(57) ABSTRACT

Disclosed are methods to treat allergic conditions, including pulmonary and non-pulmonary conditions, in a subject by administering a composition that inhibits Pim kinase. Also disclosed are methods to treat allergic conditions in a subject by administering a composition that induces expression of Runx3.

8 Claims, 46 Drawing Sheets

(56) References Cited

OTHER PUBLICATIONS

Serre et al., (Mol Immunol. Apr. 13, 2010; 47:1914-1922).*
Stout et al., (J Immunol. 2004;173:6409-6417).*
Anderson (Lancet. 2008;372:1107-19).*
Wang et al., (J All Clin Immunol. Aug. 2010; 126(2):306-316. Epub Jul. 10, 2010).*
Kim et al., (J Cell Biochem. 2008;105:1048-1058).*
Li et al., (J Allergy Clin Immunol. Jul. 2000; 106(1)Part 1:150-158).*
Olla et al., (Bioorganic & Med Chem Letters. Mar. 1, 2009;19:1512-1516) (ePub Jan. 9, 2009).*
Eigenmann, (Ped Allergy Immunol. Jun. 2002;13(3):162-171. Abstract Only).*
Aaronson et al., "A road map for those who don't know JAK-STAT," Science, 2002, vol. 296, pp. 1653-1655.
Aho et al., "Expression of human pim family genes is selectively up-regulated by cytokines promoting T helper type 1, but not T helper type 2, cell differentiation," Immunology, 2005, vol. 116, pp. 82-88.
Aho et al., "Pim-1 kinase phosphorylates RUNX family transcription factors and enhances their activity," BMC Cell Biol., 2006, vol. 7, pp. 21-29.
Alexander et al., "Trial of cyclosporin in corticosteroid-dependent chronic severe asthma," Lancet, 1992, vol. 339, pp. 324-328.
Amaravadi et al., "The survival kinases Akt and Pim as potential pharmacological targets," J Clin Invest, 2005, vol. 115, pp. 2618-2624.
Amson et al., "The human protooncogene product p33 pim is expressed during fetal hematopoiesis and in diverse leukemias," Proc Natl Acad Sci USA, 1989, vol. 86, pp. 8857-8861.
Andina et al., "Proviral integration site for Moloney murine leukemia virus 1, but not phosphatidylinositol-3 kinase, is essential in the antiapoptotic signaling cascade initiated by IL-5 in eosinophils," J Allergy Clin Immunol., 2009, vol. 123, pp. 603-611.
Azzawi et al., "Identification of activated T lymphocytes and eosinophils in bronchial biopsies in stable atopic asthma," Am Rev Respir Dis, 1990, vol. 142, pp. 1407-1413.
Bachmann et al., "The serine/threonine kinase Pim-1," Int J Biochem Cell Biol, 2005, vol. 37, pp. 726-730.
Bellacosa et al., "Molecular alterations of the AKT2 oncogene in ovarian and breast carcinomas," Int J Cancer, 1995, vol. 64, pp. 280-285.
Blumchen et al., "Oral peanut immunotherapy in children with peanut anaphylaxis," J Allergy Clin Immunol., 2010, vol. 126(1), pp. 83-91.
Borgonovo et al., "Recruitment of circulating allergen-specific T lymphocytes to the lung on allergen challenge in asthma," J Allergy Clin Immunol, 1997, vol. 100, pp. 669-678.
Brault et al., "PIM serine/threonine kinases in the pathogenesis and therapy of hematologic malignancies and solid cancers," Haematologica, 2010, vol. 95, pp. 1004-1015.
Brenner et al., "Loss of Runx3 function in leukocytes is associated with spontaneously developed colitis and gastric mucosal hyperplasia," Proc Natl Acad Sci USA, 2004, vol. 101(45), pp. 1601-1621.
Busse et al., "Asthma," N. Engl J Med, 2001, vol. 344, pp. 350-362.
Busse et al., "Mechanisms of persistent airway inflammation in asthma. A role for T cells and T-cell products," Am J Respir Crit Care Med, 1995, vol. 152, pp. 388-393.
Chen et al., "Pim kinase inhibitor, SGI-1776, induces apoptosis in chronic lymphocytic leukemia cells," Blood, 2009, vol. 114, pp. 4150-4157.
Chen et al., Pim serine/threonine kinases regulate the stability of Socs-1 protein. Proc Natl Acad Sci U S A, 2002, vol. 99, pp. 2175-2180.
Cheng et al., "AKT2, a putative oncogene encoding a member of a subfamily of protein-serine/threonine kinases, is amplified in human ovarian carcinomas," Proc Natl Acad Sci U S A, 1992, vol. 89, pp. 9267-9271.
Cibull et al., "Overexpression of Pim-1 during progression of prostatic adenocarcinoma," J Clin Pathol., 2006, vol. 59, pp. 285-288.
Cohn et al., "Cutting Edge: IL-4-independent induction of airway hyperresponsiveness by Th2, but not Th1, cells," J Immunol, 1998, vol. 161, pp. 3813-3816.
Cohn et al., "Induction of airway mucus production by T helper 2 (Th2) cells: a critical role for interleukin 4 in cell recruitment but not mucus production," J Exp Med., 1997, vol. 186, pp. 1737-1747.
Coyle et al., "Virus-specific CD8+ cells can switch to interleukin 5 production and induce airway eosinophilia," J Exp Med, 1995, vol. 181, pp. 1229-1233.
Croft et al., "Generation of polarized antigen-specific CD8 effector populations: reciprocal action of interleukin (IL)-4 and IL-12 in promoting type 2 versus type 1 cytokine profiles," J Exp Med, 1994, vol. 180, pp. 1715-1728.
Cruz-Guilloty et al., "Runx3 and T-box proteins cooperate to establish the transcriptional program of effector CTLs," J Exp Med, 2009, vol. 206, pp. 51-59.
Dautry et al., "Regulation of pim and myb mRNA accumulation by interleukin 2 and interleukin 3 in murine hematopoietic cell lines," J Biol Chem, 1988, vol. 263, pp. 17615-17620.
Davis et al., "Small molecule dual antagonists of Pim 1 and 3 kinases ameliorate experimental autoimmune encephalomyelitis," 26th Congress of the European Committee for Treatment and Research in Multiple Sclerosis (ECTRIMS) & 15th Annual Conference of Rehabilitation in MS (RIMS), Oct. 14, 2010 available at www.registration.akm.ch/einsicht.php?XNABSTRACT_ID=113502&XNSPRACHE_ID=2&XNKONGRESS_=126&XNMASKEN_ID=900.
Djuretic et al., "Transcription factors T-bet and Runx3 cooperate to activate IFNg and silence IL4 in T helper type 1 cells," Nat Immunol, 2007, vol. 8, pp. 145-153.
Eigenmann et al., "Human T cell clones and cell lines specific to ovomucoid recognize different domains and consistently express IL-5," Adv Exp Med Biol, 1996, vol. 409, pp. 217.
Eigenmann, "T lymphocytes in food allergy: overview of an intricate network of circulating and organ-resident cells," Pediatr Allergy Immunol, 2002, vol. 13, pp. 162-171.
Fainaru et al., "Runx3 regulates mouse TGF-beta-mediated dendritic cell function and its absence results in airway inflammation," EMBO J., 2004, vol. 23(4), pp. 969-979.
Flaishon et al., "Cutting edge: anti-inflammatory properties of low levels of IFN-gamma," J Immunol, 2002, vol. 168, pp. 3707-3711.
Fox et al., "The Pim kinases control rapamycin-resistant T cell survival and activation," J Exp Med., 2005, vol. 201, pp. 259-266.
Gavett et al., "Depletion of murine CD4+ T lymphocytes prevents antigen-induced airway hyperreactivity and pulmonary eosinophilia," Am J Respir Cell Mol Biol., 1994, vol. 10, pp. 587-593.
Hamelmann et al., "Requirement for CD8+ T cells in the development of airway hyperresponsiveness in a marine model of airway sensitization," J Exp Med, 1996, vol. 183, pp. 1719-1729.
Heaton et al, "An immunoepidemiological approach to asthma: Identification of in-vitro T cell response patterns associated with different wheezing phenotypes in children," Lancet, 2005, vol. 365, pp. 142-149.
Hessel et al., "Development of airway hyperresponsiveness is dependent on interferon-gamma and independent of eosinophil infiltration," Amer J Resp Cell Molec Biol, 1997, vol. 16, pp. 325-334.
Hogan et al., "A novel T cell-regulated mechanism modulating allergen-induced airways hyperreactivity in BALB/c mice independently of IL-4 and IL-5," J Immunol., 1998, vol. 161, pp. 1501-1509.
Hogan et al., "Interleukin-5-producing CD4+ T cells play a pivotal role in aeroallergen-induced eosinophilia, bronchial hyperreactivity, and lung damage in mice," Am J Respir Crit Care Med, 1998, vol. 157, pp. 210-218.
Hu et al., "PIM-1-specific mAb suppresses human and mouse tumor growth by decreasing PIM-1 levels, reducing Akt phosphorylation, and activating apoptosis," J Clin Invest, 2009, vol. 119, pp. 362-375.
Isogai et al., "CD8+ alphabeta T cells can mediate late airway responses and airway eosinophilia in rats," J Allergy Clin Immunol, 2004, vol. 114, pp. 1345-1352.
Ivanov et al., "The orphan nuclear receptor RORgammat directs the differentiation program of proinflammatory IL-17+ T helper cells," Cell, 2006, vol. 126(6), pp. 1121-1133.

(56) References Cited

OTHER PUBLICATIONS

Katakami et al., "Role of pim-1 in smooth muscle cell proliferation," J Biol Chem, 2004, vol. 279, pp. 54742-54749.
Kicic et al., "Decreased fibronectin production significantly contributes to dysregulated repair of asthmatic epithelium," Am J Respir Crit Care Med., 2010, vol. 181, pp. 889-898.
Knight et al., "CD4 T cells activated in the mesenteric lymph node mediate gastrointestinal food allergy in mice," Am J Physiol Gastrointest Liver Physiol., 2007, vol. 293(6), pp. G1234-G1243.
Kohu et al., "The Runx3 transcription factor augments Th1 and down-modulates Th2 phenotypes by interacting with and attenuating GATA3," J Immunol, 2009, vol. 183, pp. 7817-7824.
Koike et al., "Identification of heterochromatin protein 1 (HP1) as a phosphorylation target by Pim-1 kinase and the effect of phosphorylation on the transcriptional repression function of HP1(1)," FEBS Lett, 2000, vol. 467, pp. 17-21.
Kolls et al., "Interleukin-17 family members and inflammation," Immunity, 2004, vol. 21, pp. 467-476.
Komine et al., "The Runx1 transcription factor inhibits the differentiation of naive CD4+ T cells into the Th2 lineage by repressing GATA3 expression," J Exp Med, 2003, vol. 198 (1), pp. 51-61.
Kondapaka et al., "Perifosine, a novel alkylphospholipid, inhibits protein kinase B activation," Mol Cancer Ther, 2003, vol. 2, pp. 1093-1103.
Kweon et al., "Systemically derived large intestinal CD4(+)Th2 cells play a central role in STAT6—mediated allergic diarrhea," J Clin Invest., 2000, vol. 106(2), pp. 199-206.
Lack et al., "Nebulized but not parenteral IFN-gamma decreases IgE production and normalizes airway function in a murine model of allergen sensitization," J Immunol, 1994, vol. 152, pp. 2546-2554.
Laoukili et al., "IL-13 alters mucociliary differentiation and ciliary beating of human respiratory epithelial cells," J Clin Invest, 2001, vol. 108, pp. 1817-1824.
Larche et al., "The role of T lymphocytes in the pathogenesis of asthma," J Allergy Clin Immunol, 2003, vol. 111, pp. 450-463; quiz 464.
Lee et al., "Runx3 inhibits IL-4 production in T cells via physical interaction with NFAT," Biochem Biophys Res Commun, 2009, vol. 381, pp. 214-217.
Lopez et al., "Recombinant human interleukin 5 is a selective activator of human eosinophil function," J Exp Med, 1988, vol. 167, pp. 219-224.
Maita et al., "PAP-1, a novel target protein of phosphorylation by pim-1 kinase," Eur J Biochem, 2000, vol. 267, pp. 5168-5178.
Masure et al., "Molecular cloning, expression and characterization of the human serine/threonine kinase Akt-3," Eur J Biochem, 1999, vol. 265, pp. 353-360.
Mikkers et al., "Mice deficient for all PIM kinases display reduced body size and impaired responses to hematopoietic growth factors," Mol Cell Biol, 2004, vol. 24, pp. 6104-6115.
Miyahara et al., "Contribution of antigen-primed CD8+ T cells to the development of airway hyperresponsiveness and inflammation is associated with IL-13," J Immunol, 2004, vol. 172, pp. 2549-2558.
Miyahara et al., "Effector CD8+ T cells mediate inflammation and airway hyper-responsiveness," Nat Med, 2004, vol. 10, pp. 865-869.
Mullarkey et al., "Methotrexate in the treatment of corticosteroid-dependent asthma. A double-blind crossover study," N Engl J Med, 1988, vol. 318, pp. 603-607.
Nawijn et al., "For better or for worse: the role of Pim oncogenes in tumorigenesis," Nat Rev Cancer, 2011, vol. 11, pp. 23-34.
Nieborowska-Skorska et al., "Complementary functions of the antiapoptotic protein A1 and serine/threonine kinase pim-1 in the BCR/ABL-mediated leukemogenesis," Blood, 2002, vol. 99, pp. 4531-4539.
Oshiba et al., "Passive transfer of immediate hypersensitivity and airway hyperresponsiveness by allergen-specific immunoglobulin (Ig) E and IgG1 in mice," J Clin Invest, 1996, vol. 97, pp. 1398-1408.
Patra et al., "PKB rescues calcineurin/NFAT-induced arrest of Rag expression and pre-T cell differentiation," J Immunol, 2006, vol. 177, pp. 4567-4576.

Perrier et al., "Allergen-specific antibody and cytokine responses, mast cell reactivity and intestinal permeability upon oral challenge of sensitized and tolerized mice," Clin Exp Allergy, 2010, vol. 40, pp. 153-162.
Rainio et al., "Cutting edge: Transcriptional activity of NFATc1 is enhanced by the Pim-1 kinase," J Immunol, 2002, vol. 168, pp. 1524-1527.
Robinson et al., "Predominant TH2-like bronchoalveolar T-lymphocyte population in atopic asthma," N. Engl J. Med., 1992, vol. 326, pp. 298-304.
Rosenberg et al., "Eosinophil trafficking in allergy and asthma," J Allergy Clin Immunol, 2007, vol. 119, pp. 1303-1310; quiz 1311-1302.
Seder et al., "CD8+ T cells can be primed in vitro to produce IL-4," J Immunol, 1992, vol. 148, pp. 1652-1656.
Shin et al., "The Effects of a Pim Kinase Inhibitor on Allergen-Induced Airway Hyperresponsiveness (AHR) and Inflammation," J. Allergy & Clin. Immunol., 2010, vol. 125(2), p. AB63.
Stahl et al., "Deregulated Akt3 activity promotes development of malignant melanoma," Cancer Res, 2004, vol. 64, pp. 7002-7010.
Stout et al., "IL-5 and granulocyte-macrophage colony-stimulating factor activate STAT3 and STAT5 and promote Pim-1 and cyclin D3 protein expression in human eosinophils," J Immunol., 2004, 173, pp. 6409-6417.
Takeda et al., "Development of eosinophilic airway inflammation and airway hyperresponsiveness in mast cell-deficient mice," J Exp Med, 1997, vol. 186, pp. 449-454.
Takeda et al., "S-carboxymethylcysteine normalises airway responsiveness in sensitised and challenged mice," Eur Respir J, 2005, vol. 26, pp. 577-585.
Taniuchi et al., "Differential requirements for Runx proteins in CD4 repression and epigenetic silencing during T lymphocyte development," Cell, 2002, vol. 111, pp. 621-633.
Temple et al., "Microarray analysis of eosinophils reveals a number of candidate survival and apoptosis genes," Am J Respir Cell Mol Biol. 2001, vol. 25, pp. 425-433.
ten Hacken et al., "Elevated serum interferon-γ in atopic asthma correlates with increased airways responsiveness and circadian peak expiratory flow variation," Eur Resp J, 1998, vol. 11, pp. 312-316.
Tesmer et al., "Th17 cells in human disease," Immunol Rev., 2008, vol. 223, pp. 87-113.
Tomkinson et al., "Temporal association between airway hyper-responsiveness and airway eosinophilia in ovalbumin-sensitized mice," Am J Respir Crit Care Med, 2001, vol. 163, pp. 721-730.
Umetsu et al., "Asthma: an epidemic of dysregulated immunity," Nat Immunol., 2002, vol. 3, pp. 715-720.
Valdman et al., "Pim-1 expression in prostatic intraepithelial neoplasia and human prostate cancer," Prostate, 2004, vol. 60, pp. 367-371.
Van Lohuizen et al., "Predisposition to lymphomagenesis in pim-1 transgenic mice, pp. cooperation with c-myc and N-myc in murine leukemia virus-induced tumors," Cell, 1989, vol. 56, pp. 673-682.
Wang et al., "Inhibition of Pim1/3 Kinase Prevents Peanut-Induced Diarrhea and Intestinal Inflammation by Enhancing Runx3 Expression and Supressing Th2 and Th17 Cell Differentiation," J. Allergy Clin. Immunol., Feb. 2011, vol. 127(2), Supplement, p. AB234.
Wang et al., "Peanut-Induced Intestinal Allergy is Mediated Through a Mast Cell-IgE-FceRI-IL-13 Pathway," J. Allergy Clin Immunol, 2010, vol. 126 (2), pp. 306-316.
Wang et al., "Pim-1 negatively regulates the activity of PTP-U2S phosphatase and influences terminal differentiation and apoptosis of monoblastoid leukemia cells," Arch Biochem Biophys, 2001, vol. 390, pp. 9-18.
Wang et al., "Pim-1: a serine/threonine kinase with a role in cell survival, proliferation, differentiation and tumorigenesis," J. Vet Sci., 2001, vol. 2, pp. 167-179.
Wills-Karp et al., "Interleukin-13: central mediator of allergic asthma," Science, 1998, vol. 282, pp. 2258-2261.
Wingett et al., "Pim-1 proto-oncogene expression in anti-CD3-mediated T cell activation is associated with protein kinase C activation and is independent of Raf-1," J Immunol., 1996, vol. 156(2), pp. 549-557.

(56) References Cited

OTHER PUBLICATIONS

Yan et al., "The PIM-2 kinase phosphorylates BAD on serine 112 and reverses BAD-induced cell death," J Biol Chem, 2003, vol. 278, pp. 45358-45367.

Yang et al., "Akt/protein kinase B signaling inhibitor-2, a selective small molecule inhibitor of Akt signaling with antitumor activity in cancer cells overexpressing Akt," Cancer Res, 2004, vol. 64, pp. 4394-4399.

Yoshida et al., "Effect of interferon-gamma on allergic airway responses in interferon-gamma-deficient mice," Amer J Resp Crit Care Med, 2002, vol. 166, pp. 451-456.

International Search Report for International Patent Application No. PCT/US2011/060227, mailed Jun. 11, 2012, 8 pages.

Written Opinion for International Patent Application No. PCT/US2011/060227, mailed Jun. 11, 2012, 12 pages.

Aujla, "Targeted therapies: Pim kinase inhibition and chemoresistance," Nat Rev Clin Oncol, 2010, vol. 7, p. 3.

Cao et al., "Interferon regulatory factor 4 regulates thymocyte differentiation by repressing Runx3 expression," European Journal of Immunology, 2010, vol. 40, Iss. 11, pp. 3198-3209.

Extended European Search Report for European Patent Application No. 13177100 dated Sep. 30, 2013, 9 pages.

\* cited by examiner

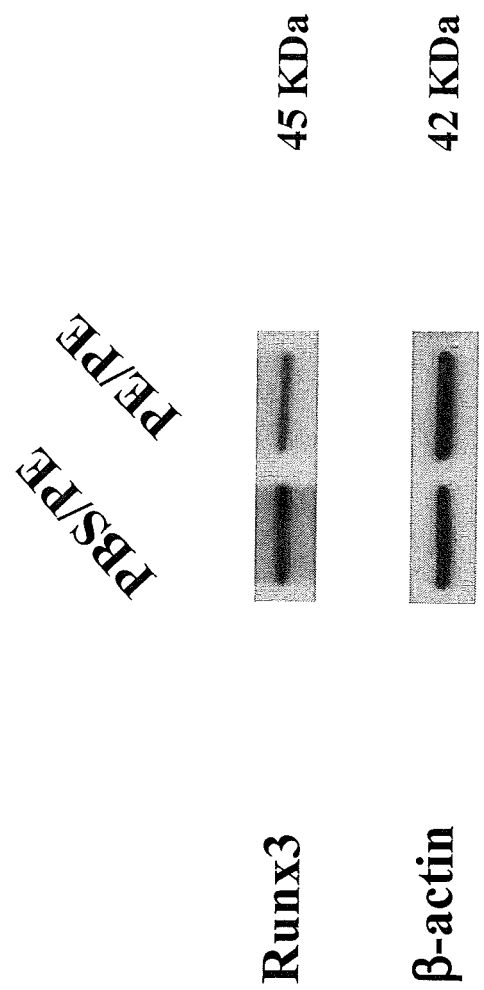

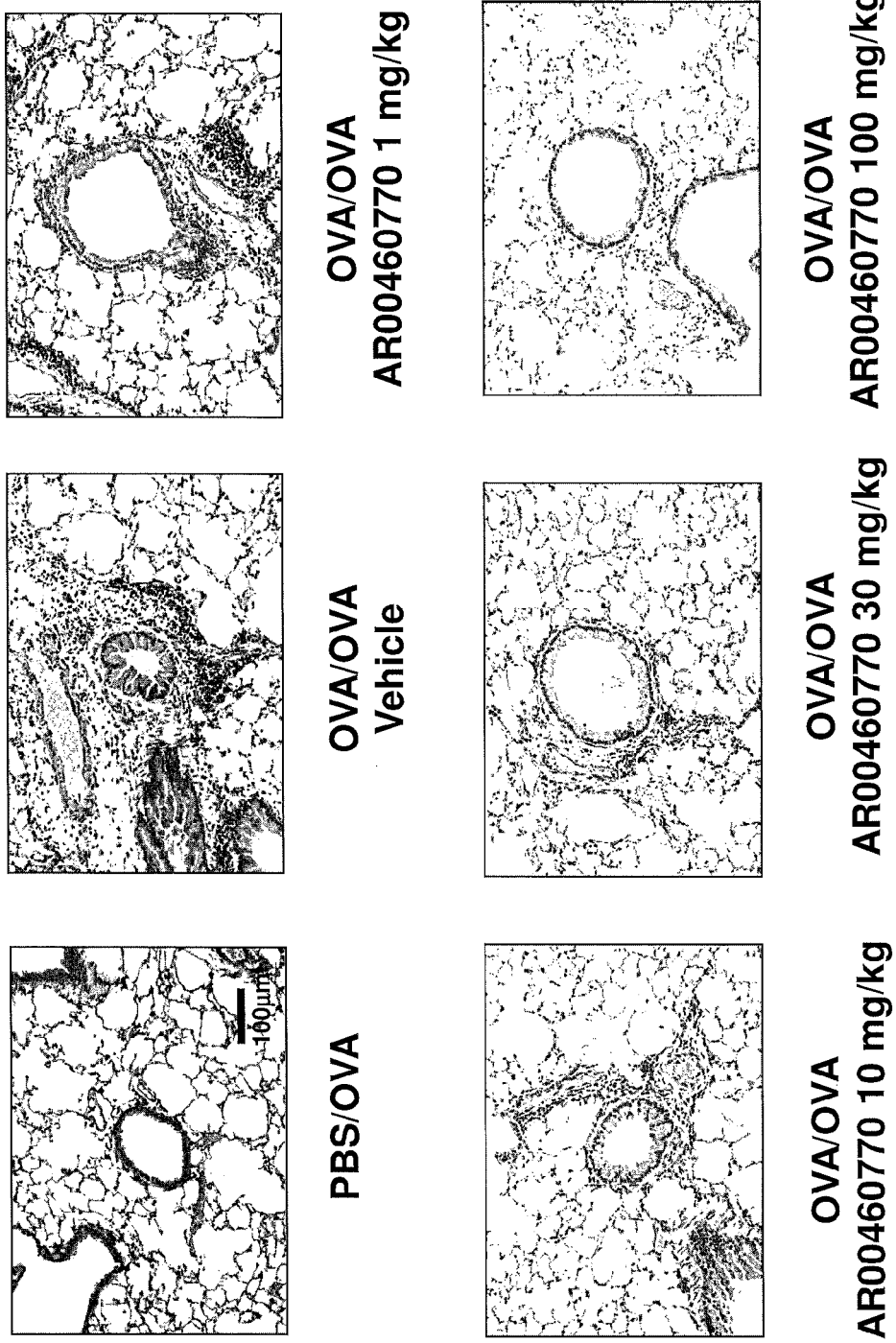
Figure 8D1

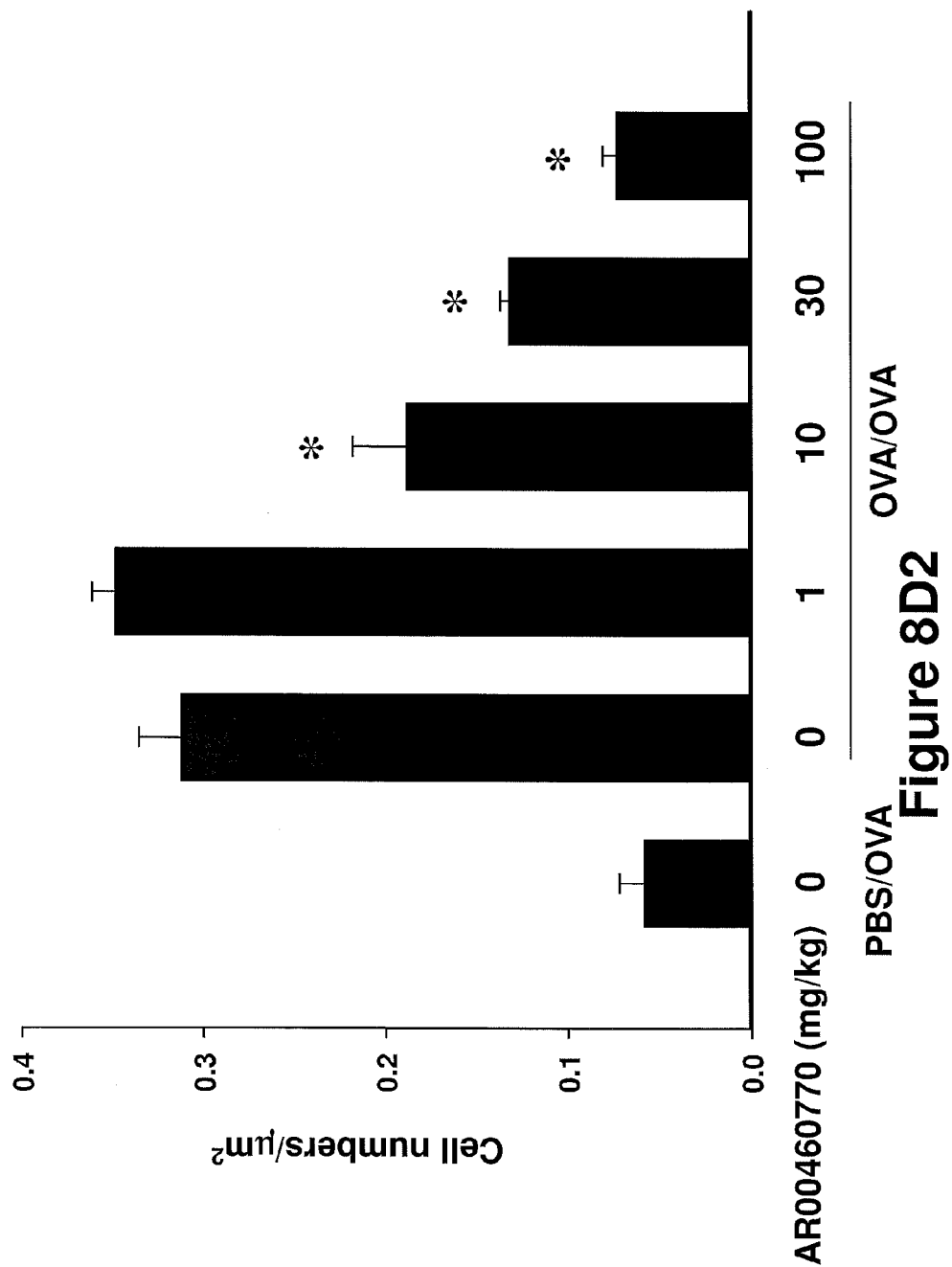
Figure 8D2

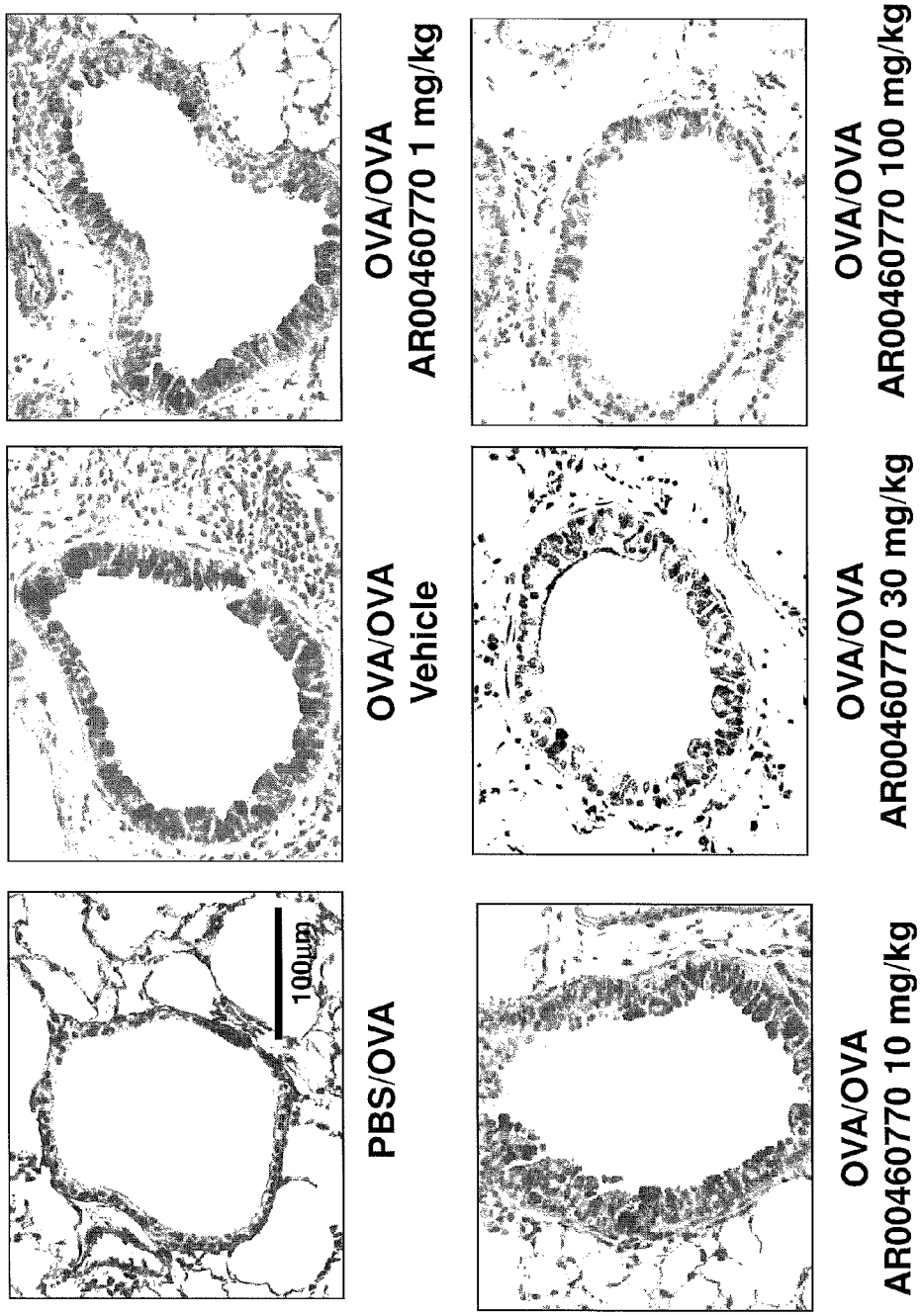
Figure 8E1

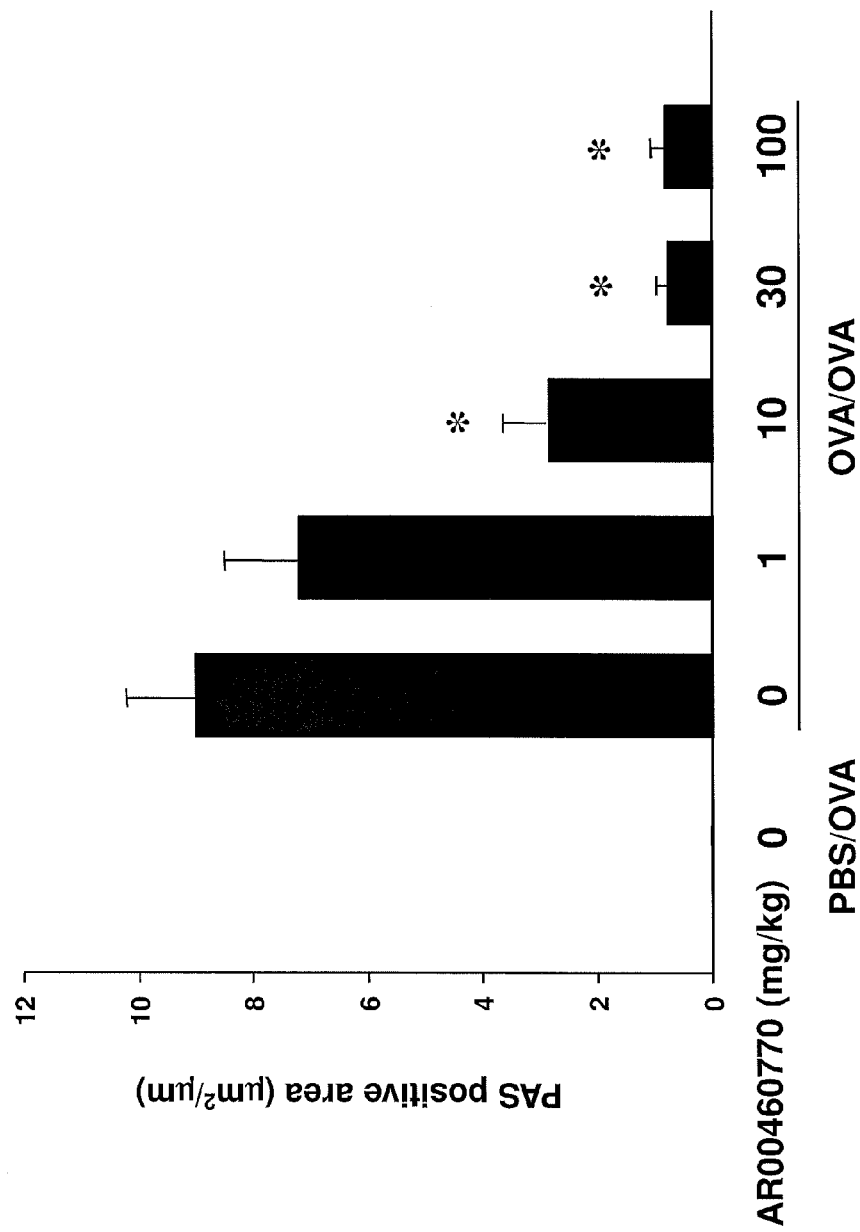
Figure 8E2

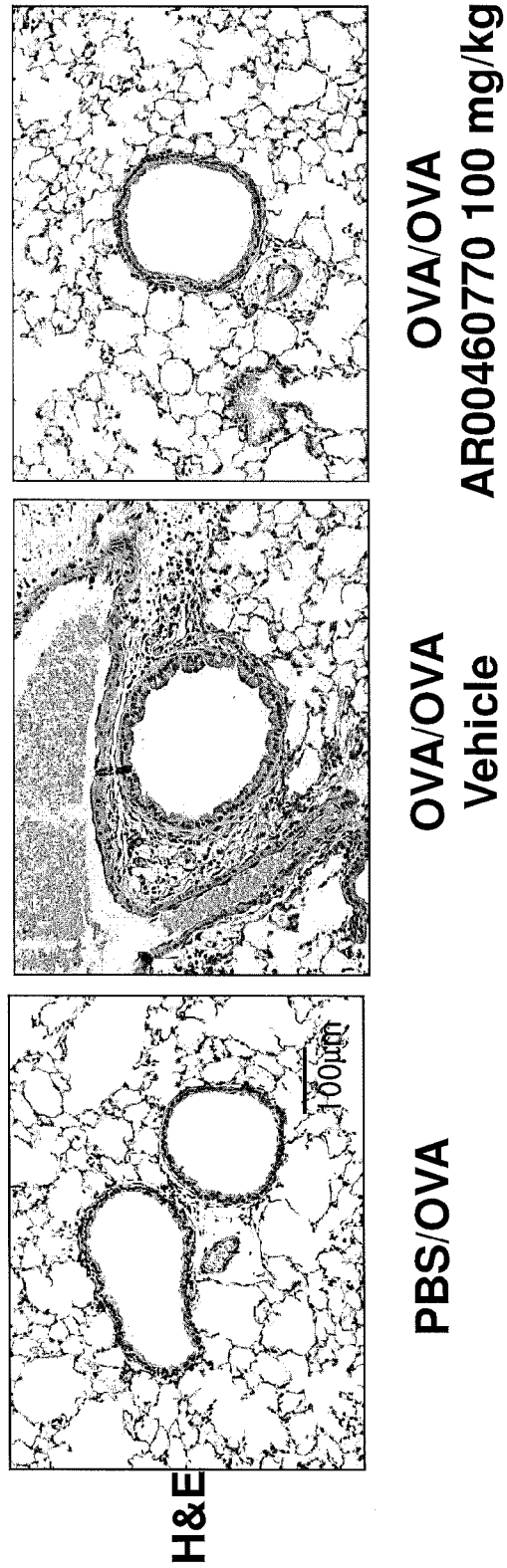
Figure 9D1

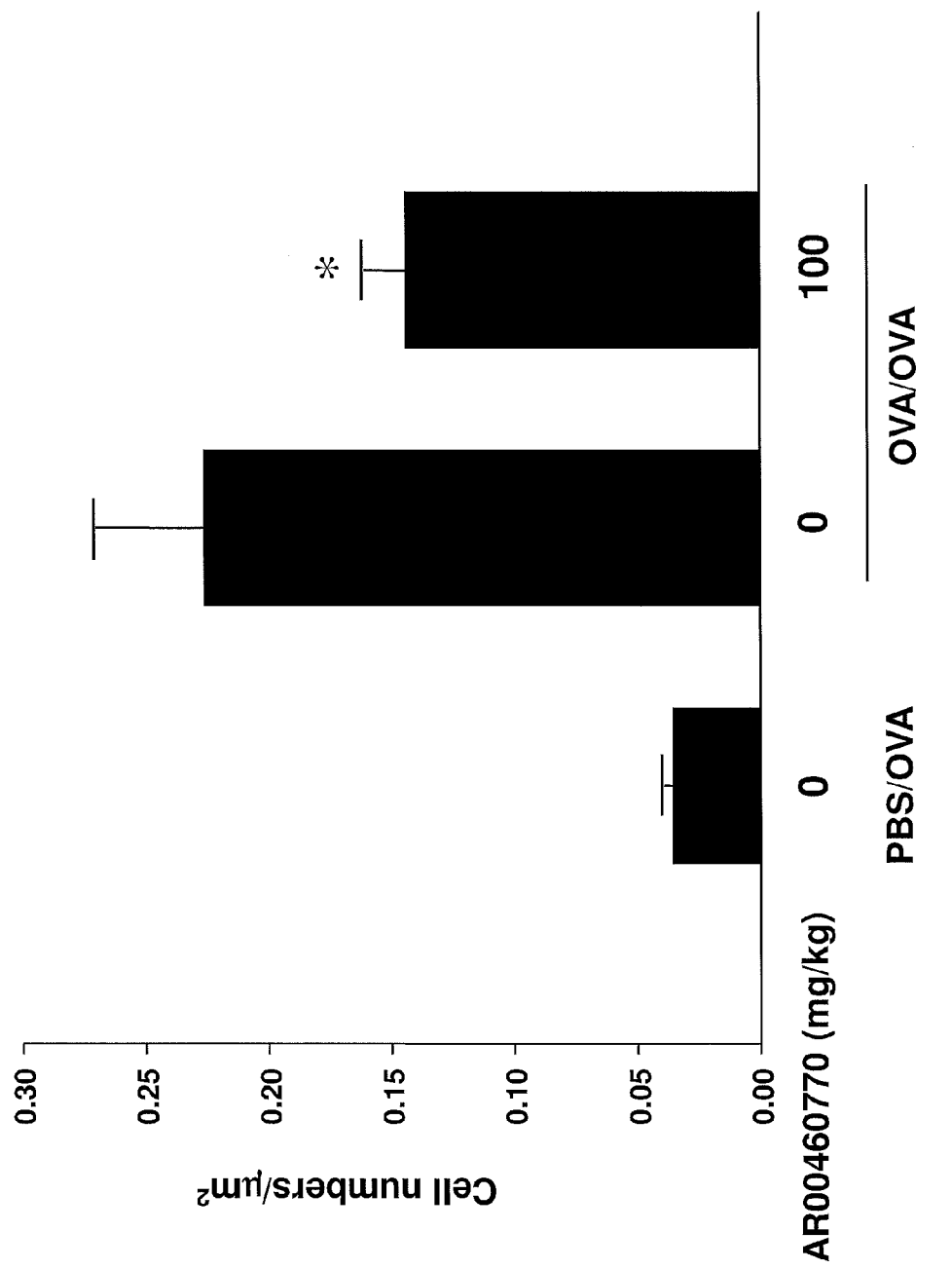
Figure 9D2

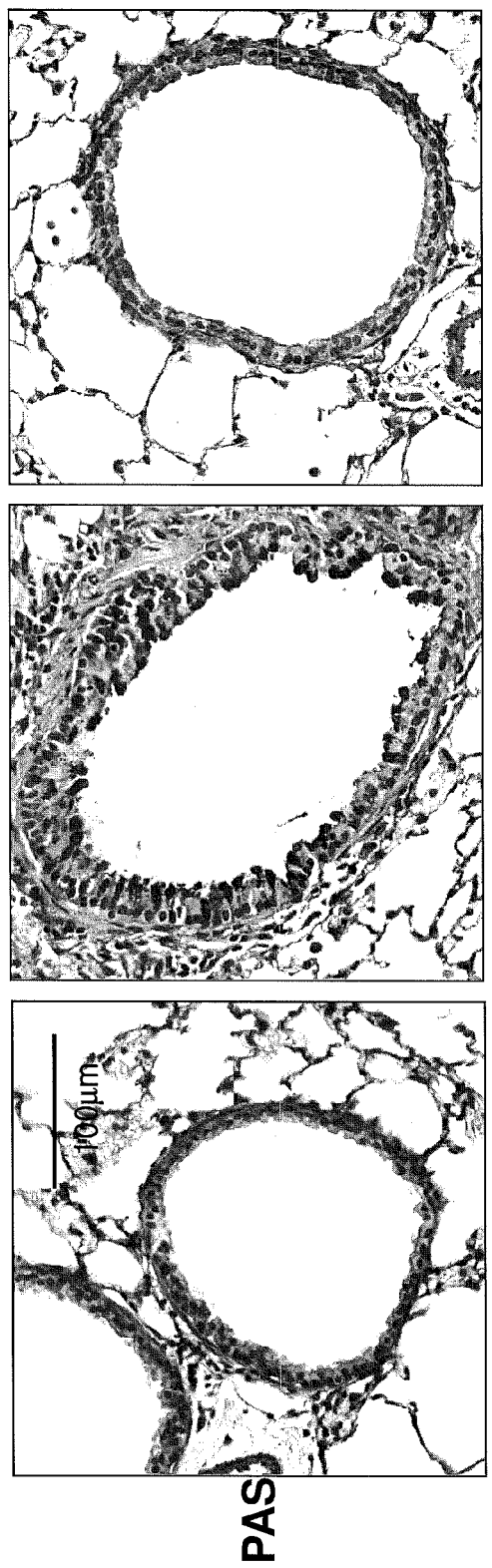
Figure 9E1

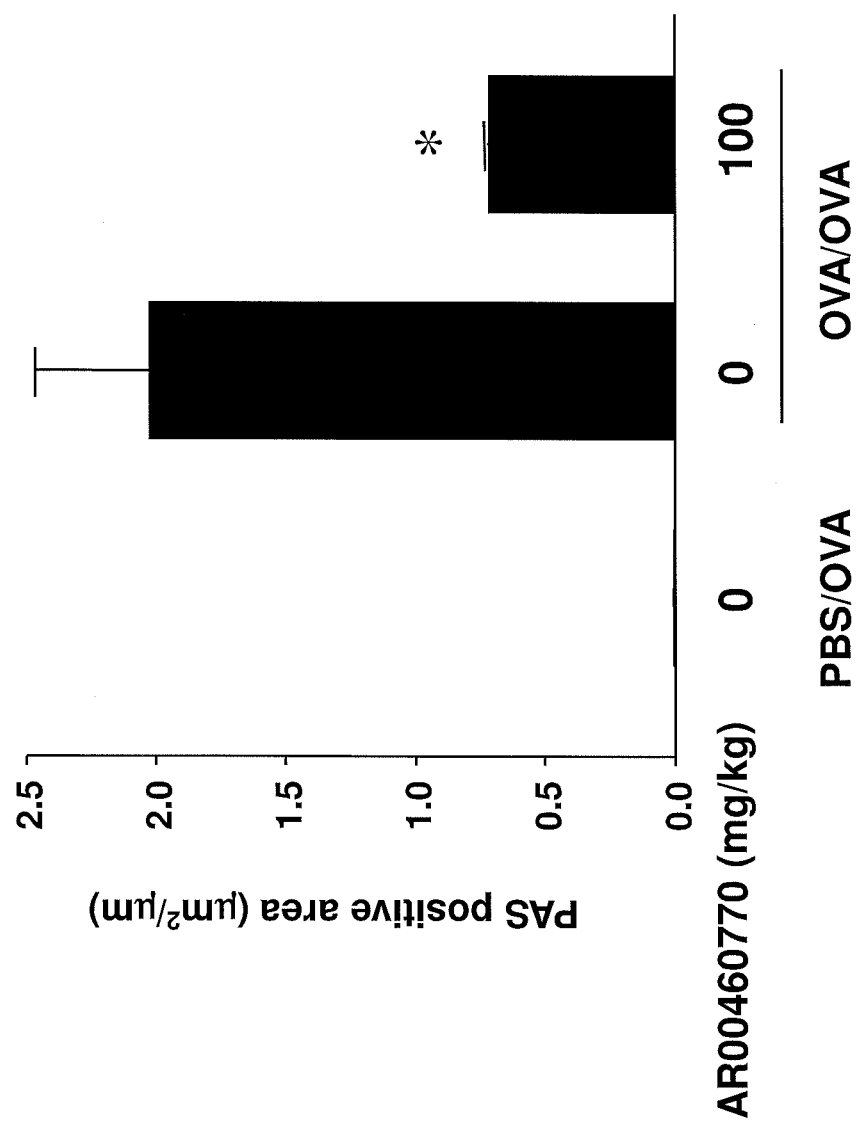
Figure 9E2

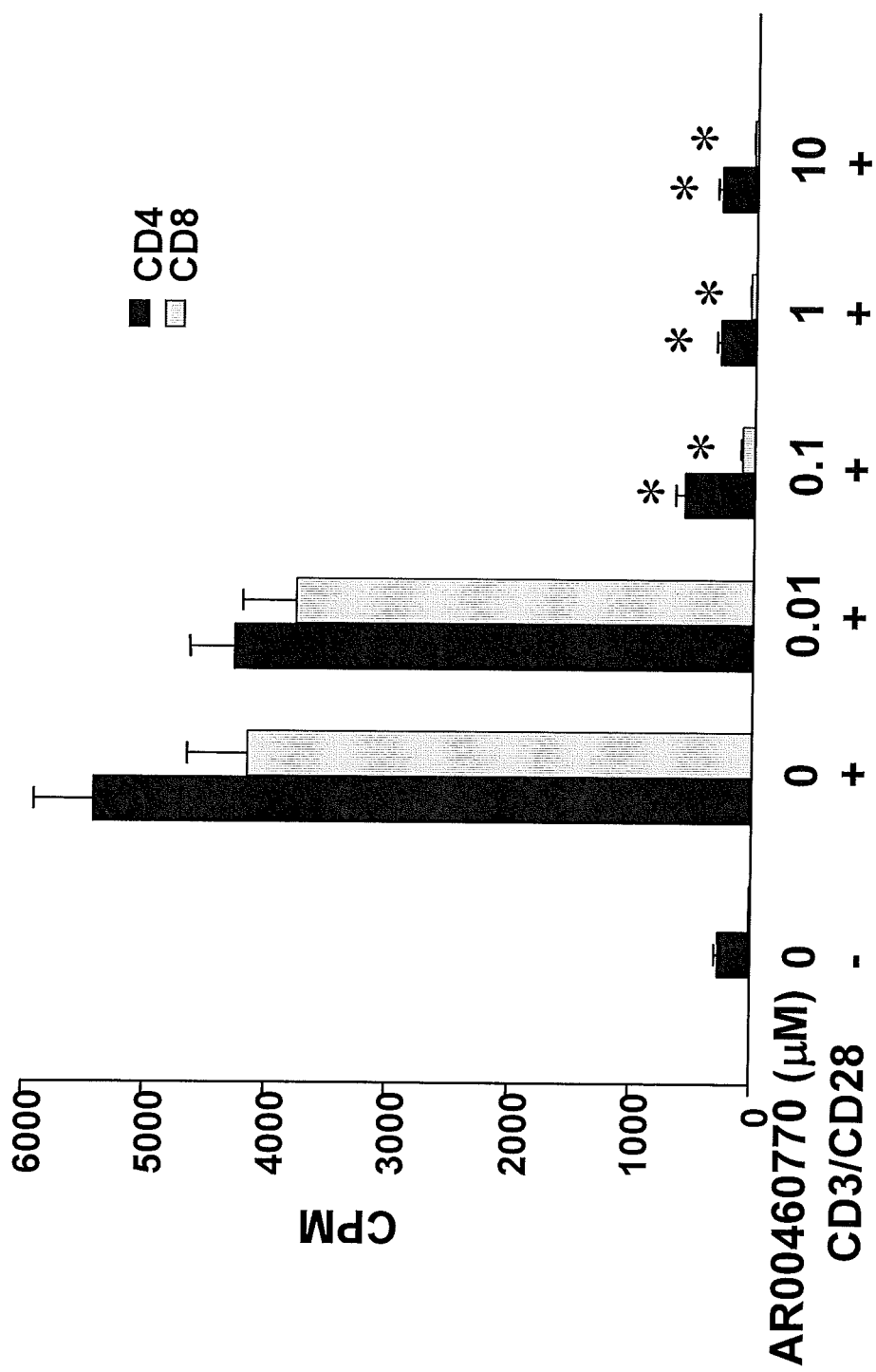

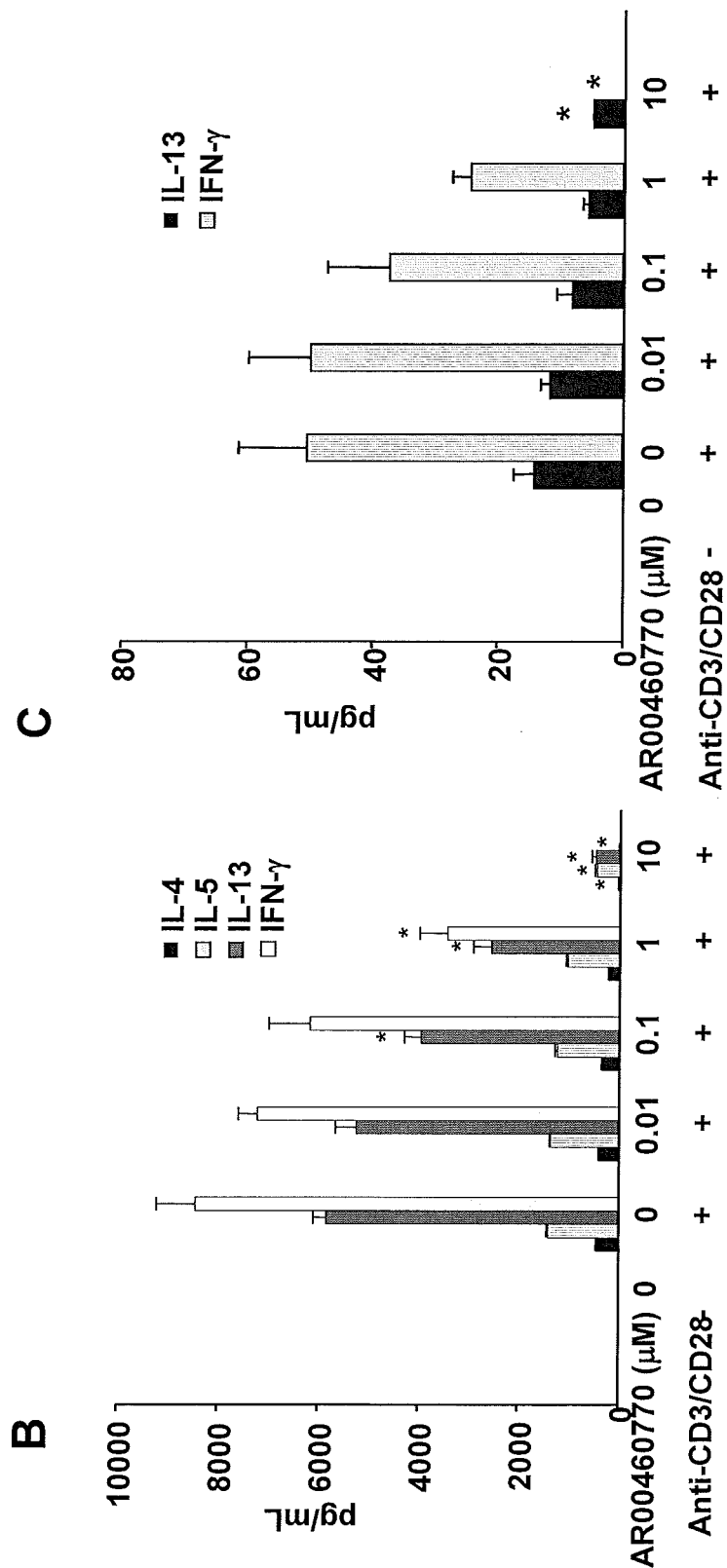

METHODS TO TREAT ALLERGIC CONDITIONS

CROSS REFERENCE TO RELATED APPLICATIONS

This application claims priority to U.S. Provisional Application No. 61/412,194 having a filing date of Nov. 10, 2010, the entire contents of which are hereby incorporated by reference in its entirety.

GOVERNMENT SUPPORT

This invention was supported in part with funding provided by NIH Grant Nos. HL-36577, HL-61005 and AI-77609 awarded by the National Institutes of Health. The government of the United States has certain rights to this invention.

FIELD OF THE INVENTION

The present invention is directed to a novel method for treating conditions related to allergic disease, such as asthma, airway hyperresponsivness (AHR) and intestinal allergy by inhibition of Pim kinase as well as by inducing expression of Runx3 (Runt-related transcription factor-3).

BACKGROUND OF THE INVENTION

Allergic conditions now affect almost 1 in 3 individuals during their lifetime and pose a major socio-economic burden on society. These conditions, including asthma, allergic rhinitis, eosinophilic esophagitis, atopic dermatitis, and intestinal allergy most often have a genetic basis. Genetic susceptibility alone cannot account for these conditions but gene-environment interactions are responsible for the induction/inception of an allergic disease and for the maintenance and progression of the disease. Understanding the mechanisms underlying these conditions is central to developing appropriate treatment strategies and even preventative interventions. Defining the pathophysiology of these atopic diseases/conditions has, on one hand been very fruitful, with identification of critical cell-cell interactions, mediators such as cytokines and chemokines, and unique signaling pathways, but direct targeting of many of these circuits has not sustained in the clinic. To a large extent this may be the result of targeting individual downstream processes and not their upstream control or convergence points. Attempts to block key mediators singly such as anti-histamines, cytokines (IL-4, IL-5, IL-13) or cells (eosinophils) have had limited success. The primary therapy for treatment of these diseases/conditions remains corticosteroids, a therapy without downstream specificity but multiple actions upstream in the pathways. Corticosteroids are not immunomodulatory but are anti-inflammatory. Moreover, when stopped, all disease manifestations return. New therapeutic approaches are needed, especially those that have the potential to modify existing disease and prevent progression.

The survival kinases are defined as cytoplasmic serine/threonine kinases that phosphorylate substrates which contribute to the control of cell proliferation, survival, differentiation, apoptosis, and tumorigenesis (Amaravadi, R., et al. 2005. J. Clin Invest 115:2618-2624). Akt is a well-studied survival kinase, in which gene amplifications have been demonstrated in several cancers (Cheng, J. Q., et al. 1992. Proc. Natl. Acad. Sci. USA 89:9267-9271; Bellacosa, A. D., et al. 1995. Int J. Cancer 64:280-285; Stahl., J. M., et al. 2004. Cancer Res. 64:7002-7010) and inhibitors assessed for treatment of malignancy (Masure, S. B., et al. 1999. Eur. J. Biochem. 265:353-360; Yang, L., et al. 2004. Cancer Res. 64:4394-4399; Kondapaka, S. B., et al. 2003. Mol. Cancer Ther. 2:1093-1103). The provirus integration site for Moloney murine leukemia virus (PIM), Pim kinase is another potent survival kinase that has been implicated in cell survival through suppression of myc-induced apoptosis (van Lohuizen, M., et al. 1989. Cell 56:673-682). There are three subtypes of Pim kinases (serine/threonine kinases) that control cell survival, proliferation, differentiation, and apoptosis (Bachmann, M., et al. 2005. Int. J. Biochem. Cell Biol. 37:726-730; Wang, Z., et al. 2001. J. Vet. Sci. 2:167-179; Amaravadi R., et al. 2005. J. Clin Invest. 115:2618-2624). Pim1 kinase and Pim2 kinase are primarily restricted to hematopoietic cells and Pim3 kinase primarily is expressed in brain, kidney, and mammary tissue (Mikkers, H., et al. 2004. Mol Cell Biol 24:6104-6115). Unlike other serine/threonine kinases, these kinases are regulated via JAK/STAT activation driven transcription of the Pim gene rather than by membrane recruitment and phosphorylation (Fox, C. J., et al. 2005. J. Exp. Med. 201:259-266). Overexpression of Pim kinase has been demonstrated in various human lymphoma, leukemic and prostatic cancers and the role of Pim-induced oncogenic transformation has been extensively studied in hematopoietic tumors (Amson, R., et al. 1989. Proc. Natl. Acad. Sci. USA 86:8857-8861; Valdman, A., et al. 2004. Prostrate 60:367-371; Cibull, T. L., et al. 2006. J. Clin. Pathol. 59:285-288; Nieborowska-Skorska, M., et al. 2002. Blood 99:4531-4539). Despite intensive studies on the role of Pim kinase in the development of tumor cells, the role of Pim kinase in immune cells has been less well studied. In human, Pim kinases are expressed in eosinophils, and play a major role in IL-5-induced eosinophil survival (Temple, R., et al. 2001. Am. J. Respir. Cell Mol. Biol. 25:425-433; Andina, N., et al 2009. J. Allergy Clin. Immunol. 123:603-611). In addition, Pim1 expression was increased in eosinophils from BAL fluid compared to blood from asthmatic patients after allergen provocation (Stout, B. A., et al. 2004. J. Immunol 173:6409-6417). In a recent study, Pim kinase was also shown to promote cell survival in T cells (Fox, C. J., et al. 2005. J. Exp Med. 201: 259-266).

Pim1 kinase is involved in cell proliferation and differentiation (Wang Z, et al. J Vet Sci. 2001; 2(3):167-179) and has been implicated in cytokine-dependent signaling in hematopoietic cells and T cells (Aho T L, et al. BMC Cell Biol. 2006; 7:21-29; Rainio E M, et al. J Immunol. 2002; 168(4): 1524-7). It has been showed that Pim1 expression is enhanced during T cell activation in a protein kinase C dependent manner (Wingett D, et al. J Immunol. 1996; 156(2):549-57). Pim1 increased T cell proliferation by enhancing activity of nuclear factor activated T-cells (NFAT) thereby increasing IL-2 production in T cells (Rainio E M, et al. J Immunol. 2002; 168(4): 1524-7).

Although it is well known that survival kinases regulate common substrates like Bad or 4EBP1 to induce cell survival and proliferation (Yan, B., et al. 2003. J. Biol. Chem. 278: 45358-45367), the downstream activities of each kinases are different. To date, the precise downstream target of Pim kinase is not known. However, c-Myc, suppressor of cytokine signaling-1 (SOCS-1), PAP-1, PTP-U2S, and heterochromatin protein 1 (HP-1) all are potential downstream targets of Pim kinase (van Lohuizen, M., et al. 1989. Cell 56:673-682; Chen, X. P., et al. 2002. Proc. Natl. Acad. Sci. USA 99:2175-2180; Maita, H., et al 2000. Eur. J. Biochem. 267:5168-5178; Koike, N., et al. 2000. FEBS Lett 467:17-21; Wang, Z., et al. 2001. Arch Biochem Biophys 390:9-18). Recently, nuclear factor of activated T-cells (NFATc1) was reported to be a potential downstream substrate of Pim kinase (Rainio, E. M.

et al. 2002. J. Immunol 168:1524-1527). As the regulation of NFAT activity has been shown to be important for normal selection of thymocytes, NFAT may play a role in the functional development of T cells (Patra, A. K. 2006. J. Immunol. 177:4567-4576) as well as in the suppression of $CD4^+$ and $CD8^+$ T cell proliferation and T cell cytokine production as a downstream substrate of Pim kinase.

$CD4^+$ T cells play a central role in controlling allergic inflammation (Buss, W. W., et al. 1995. Am J Respir Crit Care Med. 152:388-393). $CD4^+$ T cells, especially Th2 cells producing IL-4, IL-5, and IL-13, have been identified in BAL fluid and airway tissues in asthmatics (Robinson, D. S., et al. 1992. N. Engl J. Med. 326:298-304). The transfer of Th2 cells followed by airway allergen challenge in mice was sufficient to induce airway eosinophilia and AHR (Cohn, L., et al. 1997. J. Exp. Med. 186:1731-1747; Hogan, S. P., et al. 1998. J. Immunol. 161:1501-1509). Conversely, $CD8^+$ T cells, which are also key components of adaptive immunity, have drawn limited attention in the pathogenesis of asthma. However, recent studies demonstrated the increased numbers of $CD8^+$ T cells in the lung tissues of asthmatics (Azzawi, M., et al. 1990. Am. Rev. Respir. Dis. 142:1407-1413) and recent reports suggested that not only $CD4^+$ T cells but also $CD8^+$ T cells were essential to the development of AHR and allergic inflammation (Hamelmann, E., et al. 1996. J. Exp Med. 183: 1719-1729; Isogai, S., et al. 2004. J. Allergy. Clin. Immunol. 114:1345-1352; Miyahara, N., et al. 2004. J. Immunol. 172: 2549-2558; Miyahara, N., et al. 2004. Nat. Med. 10:865-869). Subsets of $CD8^+$ T cells, which produce IL-4, IL-5, and IL-13 but not IFN-γ, labeled as Tc2 cells, are known to increase AHR and airway inflammation (Croft, M., et al. 1994. J. Exp Med. 180:1715-1728; Seder, R. A., et al. 1992. J. Immunol. 148:1652-1656; Coyle, A. J., et al. 1995. J. Exp. Med. 181:1229-1233). Thus, both $CD4^+$ T cells and $CD8^+$ T cells play key roles in the pathogenesis of asthma.

Asthma is a multifactorial inflammatory disorder characterized by persistent airway inflammation and airway hyperresponsiveness (AHR) as a result of the cellular and molecular responses induced by allergen exposure, infectious pathogens, or chemical agents (Buss, W. W., et al. 2001. N. Engl. J. Med. 344:350-362; Umetsu, D. T., et al. 2002. Nat. Immunol. 3:715-720). Several clinical and experimental investigations have shown that T cells, especially Th2-type cells, play a pivotal role in the development of AHR and eosinophilic inflammation through the secretion of a variety of Th2 cytokines, including IL-4, IL-5, and IL-13 (Wills-Karp, M., et al. 1998. Science 282:2258-2261; Robinson, D. S., et al. 1992. N. Engl. J. Med. 326:298-304). These cytokines bind to the extracellular Janus kinase (JAK) receptors and subsequently induce the phosphorylation and activation of signal transducers and activators of transcription (STAT), which translocates into the nucleus, where it binds to DNA and affects basic cell functions, cellular growth, differentiation and death Aaronson, D. S., et al. 2002. Science 296:1653-1655.

Knowledge of the pathogenesis of atopic diseases/conditions was originally interpreted within the framework of a binary T helper 1 (Th1)/Th2 paradigm. This has now been broadened to incorporate other T cell subsets. Importantly, the differentiation and commitment of these populations of T cells is shaped by transcriptional circuits that center on key transcriptional regulators, the proteins that bind DNA to activate or repress gene expression. Runt-related transcription factors (Runx), are a novel family of transcription factors which are key regulators of lineage-specific gene expression, and are responsible for the development of allergic responses (Fainaru, O., et al. 2004. EMBO J. 23:969-979; Fainaru, O., et al. 2005. Proc. Natl. Acad. Sci. USA 102:10598-10603). There are three mammalian Runx genes: Runx1, Runx2, and Runx3. Runx1 is required for hematopoiesis (Okuda, T., et al. 1996. Cell 84:321-330) and Runx2 is critical regulator of osteogenesis (Ducy, P., et al. 1997. Cell 89:747-745). The Runx3 gene resides on human chromosome 1p36.1 (Levanon, D., et al. 1994. Genomics 23:425-432), which maps to a region containing susceptibility genes for asthma (Haagerup, A., et al. 2002. Allergy 57:680-686) and on mouse chromosome 4 (Calabi, F., et al. 1995. Genomics 26:607-610), which contains a susceptibility gene for atopic dermatitis (Christensen U., et al. 2009. 126:549-557). Runx3 is thought to play a critical role in regulating T-cell development, the differentiation of Th1/Th2 cells and Th1/Th2 cytokine production and the development of an allergic disease/condition. It has been reported that Pim1 kinase regulates Runx expression in vitro (Aho T L, et al. BMC Cell Biol. 2006; 7:21-29) and loss of Runx3 results in spontaneous development IBD, as well as allergic asthma (Brenner O, et al. Proc Natl Acad Sci USA. 2004; 101(45):16016-21; Fainaru O, et al. EMBO J. 2004; 23(4): 969-79). The Runx transcription factors are also key regulators of lineage-specific gene expression (Komine O, et al. J Exp Med. 2003; 198 (1): 51-61).

Peanut allergy is one of the most common food allergies characterized by acute allergic diarrhea and intestinal inflammation. During an allergic reaction, several cell types, including Th2 cells (T-helper cells), mast cells, and eosinophils, are recruited to the intestine and activated to release cytokines and chemokines, contributing to increased intestinal inflammation (Kweon M N, et al. J Clin Invest 2000; 106:199-206; Wang M, et al. J. Allergy Clin Immunol 2010, 126 (2): 306-316). $CD4^+$T cells (i.e. T cells that express CD4), especially Th2 cells, which are known to produce interleukin-4 (IL-4) and interleukin-13 (IL-13), are considered critical in the development of allergic diarrhea and intestinal inflammation (Knight A K, et al. Am J Physiol Gastrointest Liver Physiol. 2007; 293(6): G1234-43; Kweon M N, et al. J Clin Invest. 2000; 106(2): 199-206). In patients with food allergies, increased numbers of activated T cells have been correlated with elevated levels of Th2 cytokines as well as the degree of gastrointestinal (GI) inflammation and dysfunction (Eigenmann P A. Pediatr Allergy Immunol 2002; 13:162-71; Eigenmann P A, et al. Adv Exp Med Biol 1996; 409:217). It has been shown that after treatment with oral peanut immunotherapy, levels of peanut-specific Th2-cytokine (IL-4 and IL-5) production by peripheral blood mononuclear cells (PBMCs) was significantly decreased in children with peanut anaphylaxis (Blumchen K, et al. J Allergy Clin Immunol. 2010; 126(1):83-91).

More evidence in humans and mice has shown that Th17 cells, a novel subset of IL-17-producing $CD4^+$T cells, play an important role in the pathogenesis of immune-mediated diseases, including asthma and inflammatory bowel disease (IBD) (Tesmer L A, et al. Immunol Rev. 2008, 223:87-113; Kolls J K and Linden A. Immunity. 2004, 21:467-476). Th17 cells exist and are found constitutively in the small intestine of naive mice housed under conventional conditions (Ivanov I I, et al. Cell. 2006; 126(6): 1121-33). Increased levels of IL-17A (a member of the IL-17 family) have been found in the small intestine of peanut allergy mouse models as well as in the small intestine or in the peripheral blood of food allergy patients (Wang M, et al. J. Allergy Clin Immunol 2010, 126 (2): 306-316). The level of IL-17A is associated with the severity of diarrhea and intestinal inflammation. These data suggested that $CD4^+$T cells that produce Th2 and Th17 cytokines play an important role in food allergy. However, the signal pathway involved in Th2-, Th17-cells responding to allergic food reactions has not been well defined.

SUMMARY OF INVENTION

The present invention provides for a method to treat an allergic condition in a subject having or at risk of having an allergic condition, comprising administering a composition that inhibits Pim1 kinase. In one aspect, administration of the Pim1 kinase inhibitor induces expression of Runx3. In another aspect, administration of the Pim1 kinase inhibitor reduces CD4+ and CD8+ proliferation. In yet another aspect, administration of the Pim1 kinase inhibitor suppresses Th2 differentiation. In still another aspect, administration of the Pim1 kinase inhibitor suppresses Th17 differentiation.

In another embodiment, the present invention is directed toward a method to treat an allergic condition in a subject having or at risk of having an allergic condition, comprising administering a composition that induces expression of Runx3. In one aspect the composition interacts with a regulator of Runx3 expression. In another aspect, the regulator of Runx3 expression is selected from a Pim kinase, CxCL12, core binding factor-beta, transducin-like enhancer protein 1, IL-7, Stat 5, ETS-1, interferon regulatory factor 4 (IRF-4) or other regulators of Runx3. In still another aspect, the composition inhibits the activity of a compound selected from IRF-4 or Pim kinase. In yet another aspect the composition comprises an IRF-4 inhibitor. In a preferred embodiment, the composition comprises a Pim kinase inhibitor selected from a Pim1 kinase inhibitor, a Pim2 kinase inhibitor or a Pim3 kinase inhibitor.

In still another embodiment, the present invention is directed toward a method to treat an allergic condition in a subject who has or is at risk of having an allergic condition, comprising administering to the subject a composition that inhibits Pim1 kinase, wherein the allergic condition does not comprise a pulmonary condition. In another aspect the allergic condition is selected from a food allergy, eosinophilic esophagitis, chronic urticaria, atopic dermatitis, occupational allergy, allergic conjunctivitis, airborne allergic sensitivies, stinging insect allergy, inflammatory bowel disease, ulcerative colitis, Crohn's disease or drug allergies. In one aspect, the food allergy is a peanut allergy. In one aspect, the Pim1 kinase inhibitor induces expression of Runx3. In another aspect, the administration of the Pim1 kinase inhibitor reduces CD4+ and CD8+ proliferation. In yet another aspect, administration of the Pim1 kinase inhibitor suppresses Th2 differentiation. In still another aspect, administration of the Pim1 kinase inhibitor suppresses Th17 differentiation.

In yet another embodiment, the present invention is directed toward a method to treat an allergic condition in a subject who has or is at risk of having an allergic condition, comprising administering to the subject a composition that induces expression of Runx3, wherein the composition does not comprise a Pim kinase inhibitor. In one aspect the composition interacts with a regulator of Runx3 expression. In another aspect, the regulator of Runx3 expression is selected from CxCL12, core binding factor-beta, transducin-like enhancer protein 1, IL-7, Stat 5, ETS-1, and IRF-4. In still another aspect, the composition inhibits the activity of IRF-4. In yet another aspect the composition comprises an IRF-4 inhibitor.

In another aspect of the present invention, the composition activates the activity of a compound selected from CxCL12, core binding factor-beta, transducin-like enhancer protein 1, interleukin-7 (IL-7), Stat 5, or ETS-1. In another aspect, this activator is selected from G proteins, phosphatidylinositol-3 kinase (PI3K), JAK kinases, Rho GTPases, or focal adhesion-associated proteins.

In other embodiments of the present invention, the allergic condition is selected from allergic rhinitis, asthma, airway hyperresponsiveness, a food allergy, eosinophilic esophagitis, chronic urticaria, atopic dermatitis, occupational allergy, allergic conjunctivitis, hay fever, airborne allergic sensitivities, stinging insect allergy, hypersensitivity pneumonitis, eosinophilic lung diseases, inflammatory bowel disease, ulcerative colitis, Crohn's disease or drug allergies. In a preferred embodiment, the allergic disease is asthma. In still another aspect, the allergic disease is rhinitis. In another preferred embodiment, the allergic disease is a food allergy. In still another preferred embodiment, the allergic disease is a peanut allergy.

In another embodiment of the present invention, the methods further provide that the subject has been sensitized to an allergen and has been exposed to, or is at risk of being exposed to, the allergen. In one aspect, the allergen is selected from a food, a plant, a gas, a pathogen, a metal, a glue or a drug.

In another embodiment of the present invention, the composition comprises a compound selected from a small molecule inhibitor, an antibody, a chemical entity, a nucleotide, a peptide or a protein. In a preferred embodiment, the composition comprises a small molecule inhibitor. In one aspect, the small molecule inhibitor is a Pim kinase inhibitor selected from a Pim1 kinase inhibitor, a Pim2 kinase inhibitor or a Pim3 kinase inhibitor. In a preferred embodiment, the Pim kinase inhibitor is a Pim1 kinase inhibitor. In still another aspect the Pim1 kinase inhibitor is selected from AR460770 (also referred to as AARY-770 and AR00460770), AR440, SimI4A, staurosporine, bisindolymaleimide or other Pim1 kinase inhibitors.

In still another aspect of the present invention, the composition is administered by a delivery method selected from aerosol delivery, parenteral delivery or oral delivery.

All patents and publications referenced herein are incorporated by reference in their entireties.

BRIEF DESCRIPTION OF THE DRAWINGS

FIG. 1A is a protocol for induction of PE-induced intestinal allergy. FIG. 1B is a western blot analysis of Pim1 kinase expression in the jejunum from sensitized and challenged mice and control mice. FIG. 1C shows the relative mRNA expression levels of Pim family members determined by quantitative RT-PCR. FIG. 1D shows a representative immunohistochemical staining for Pim1 and Pim3 kinases in intestinal tissue from PE/PE and control PBS/PE mice. FIG. 1E shows the quantitation of mucosal Pim1 and Pim3 kinase-expressing cells in the jejunum. Results were obtained from 3 independent experiments, and each experiment included 4 mice per group (n=12). *P<0.01 between PE/PE and PBS/PE groups. PBS/PE, sham sensitized but PE challenged; PE/PE, PE sensitized and challenged.

FIGS. 2A-2C shows the expression of Runx3 in the mouse small intestine. FIG. 1A shows the relative expression of Runx3, Runx1, and Cbfβ mRNA levels in the jejunum of sensitized and challenged mice determined by quantitative RT-PCR. FIG. 2B is a western blot analysis of Runx3 protein levels in the jejunum of sensitized and challenged mice and control mice. FIG. 2C shows the quantitation of mucosal Runx3-expressing cell numbers in the jejunum of PBS/PE and PE/PE mice. Results are representative of 3 independent experiments, and each experiment included 4 mice per group.

*P<0.05, **P<0.01, #P<0.001 between PE/PE and PBS/PE groups. PBS/PE, nonsensitized but challenged with PE group; PE/PE, sensitized and challenged with PE group.

Figure 3A:
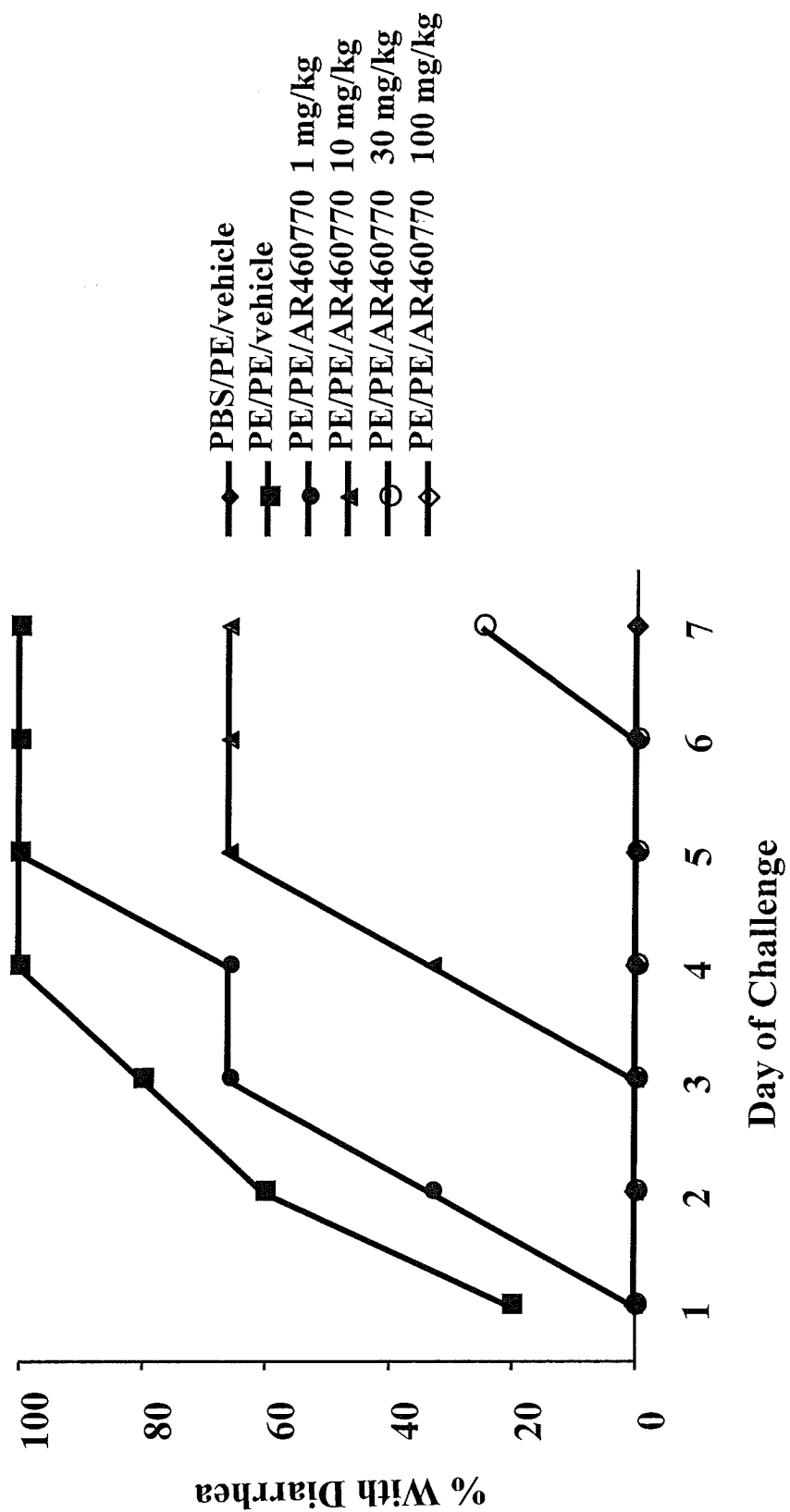
Figure 3B:
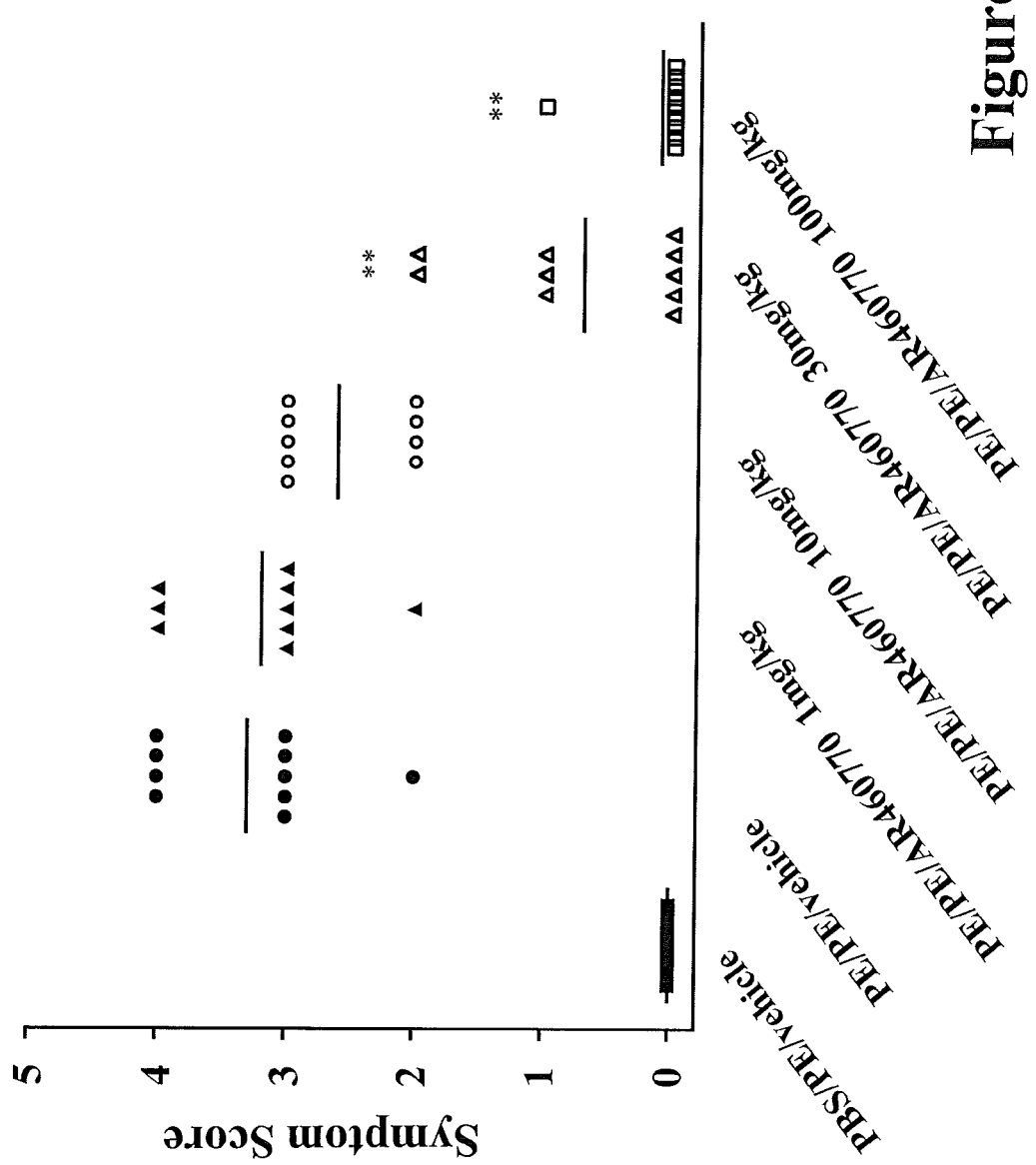
Figure 3C:
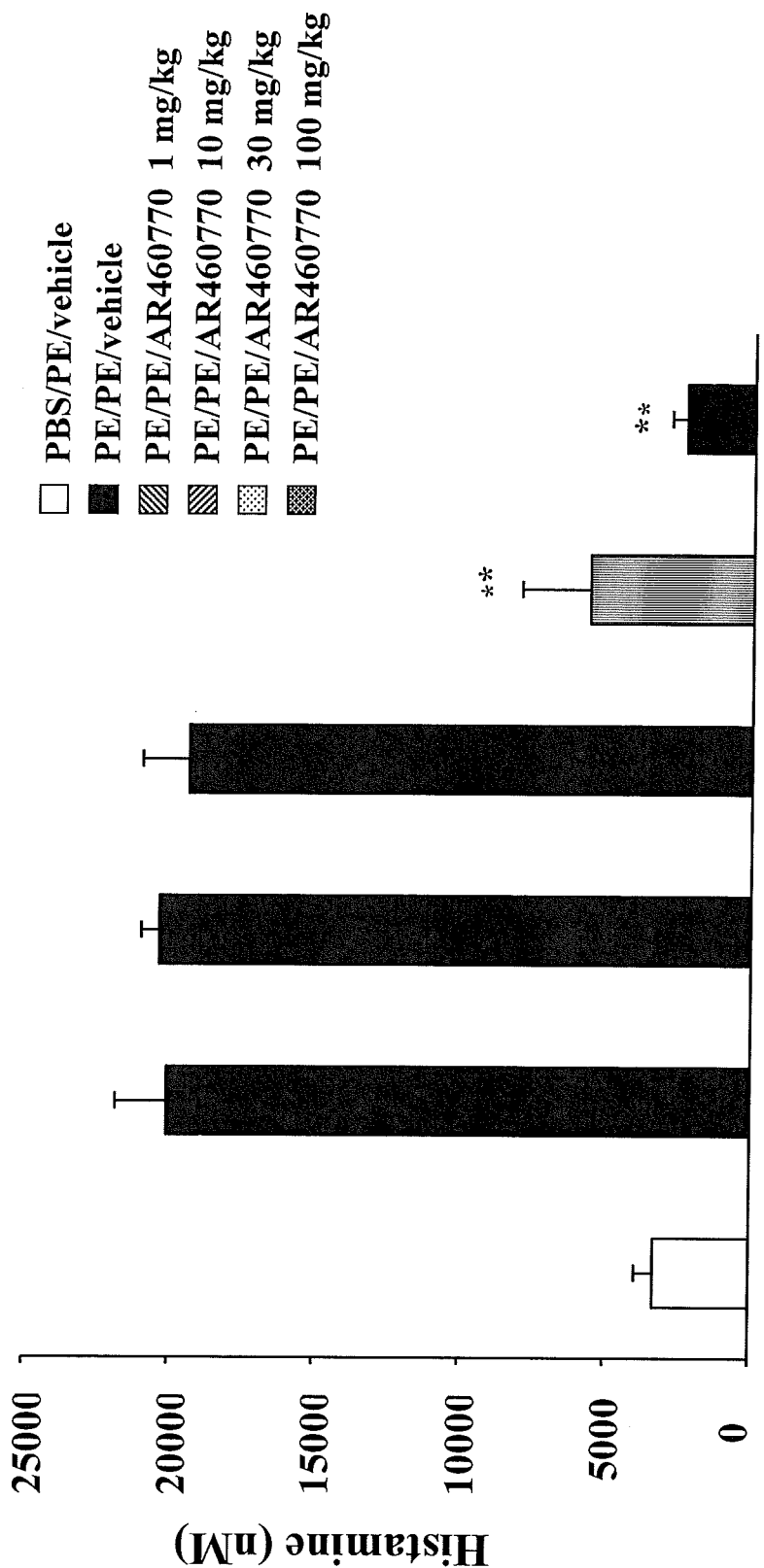
Figure 3D:
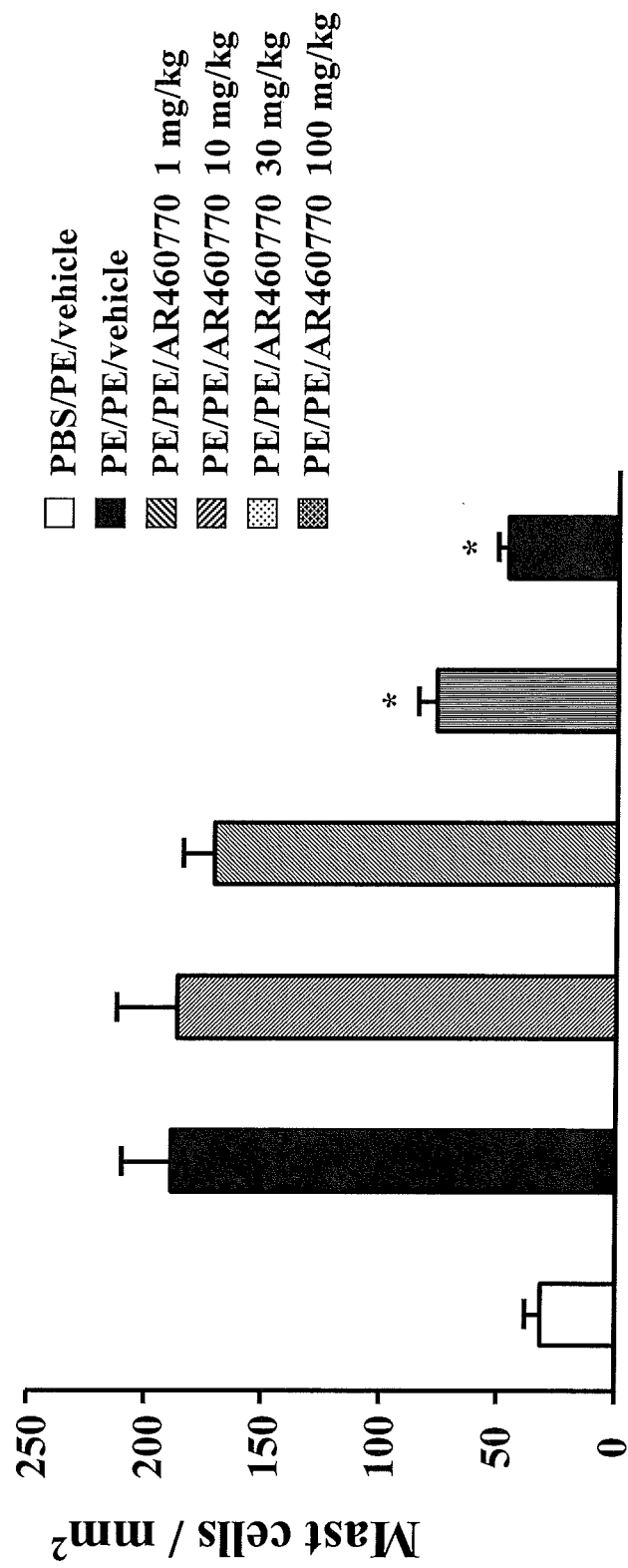
Figure 3E:
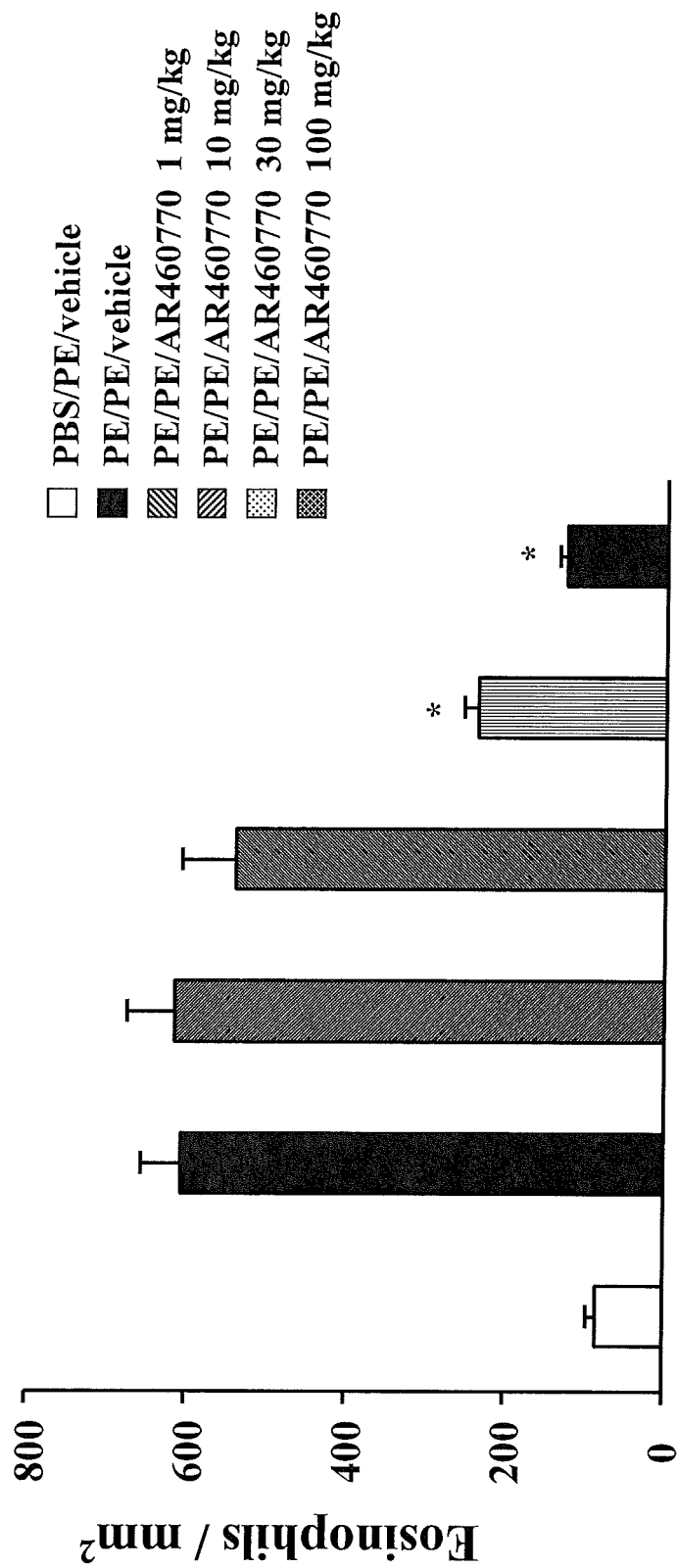
Figure 3F:
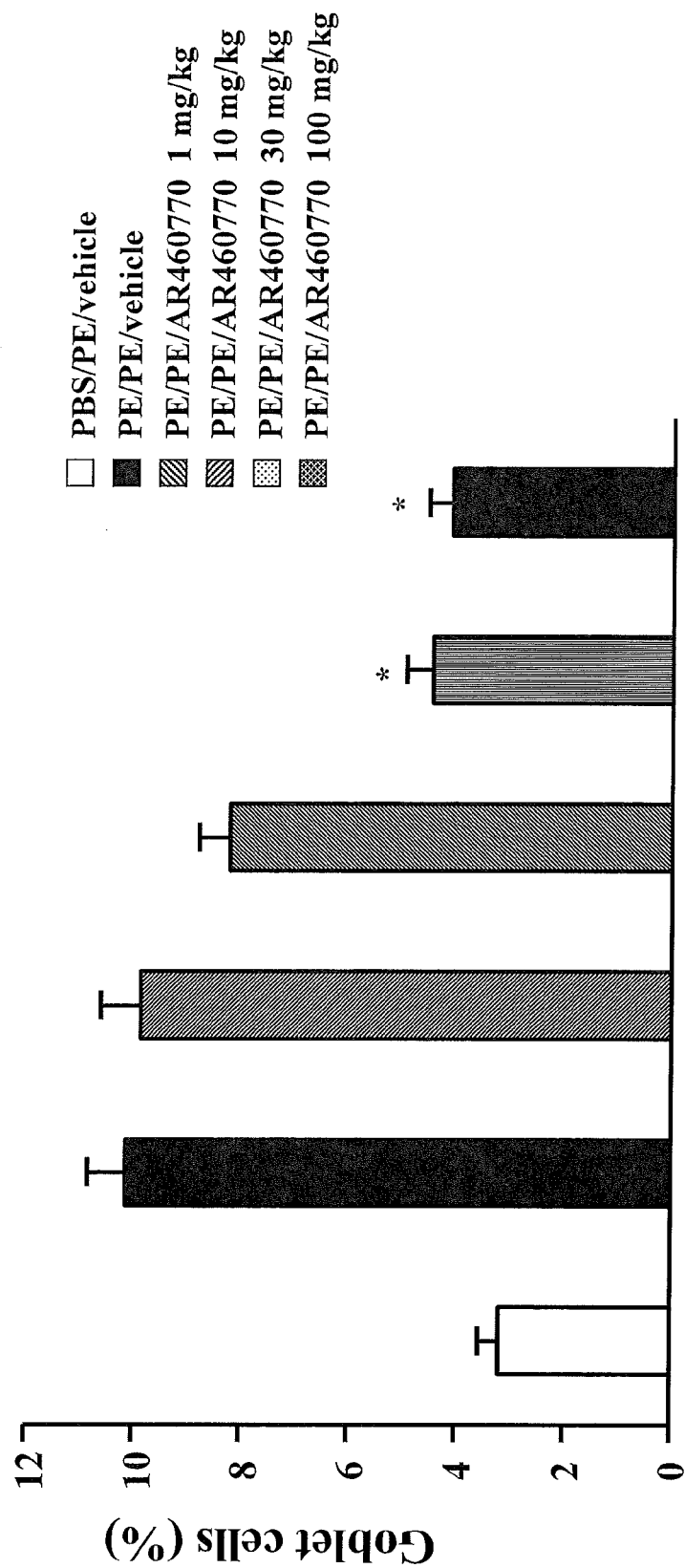
Figure 3G:
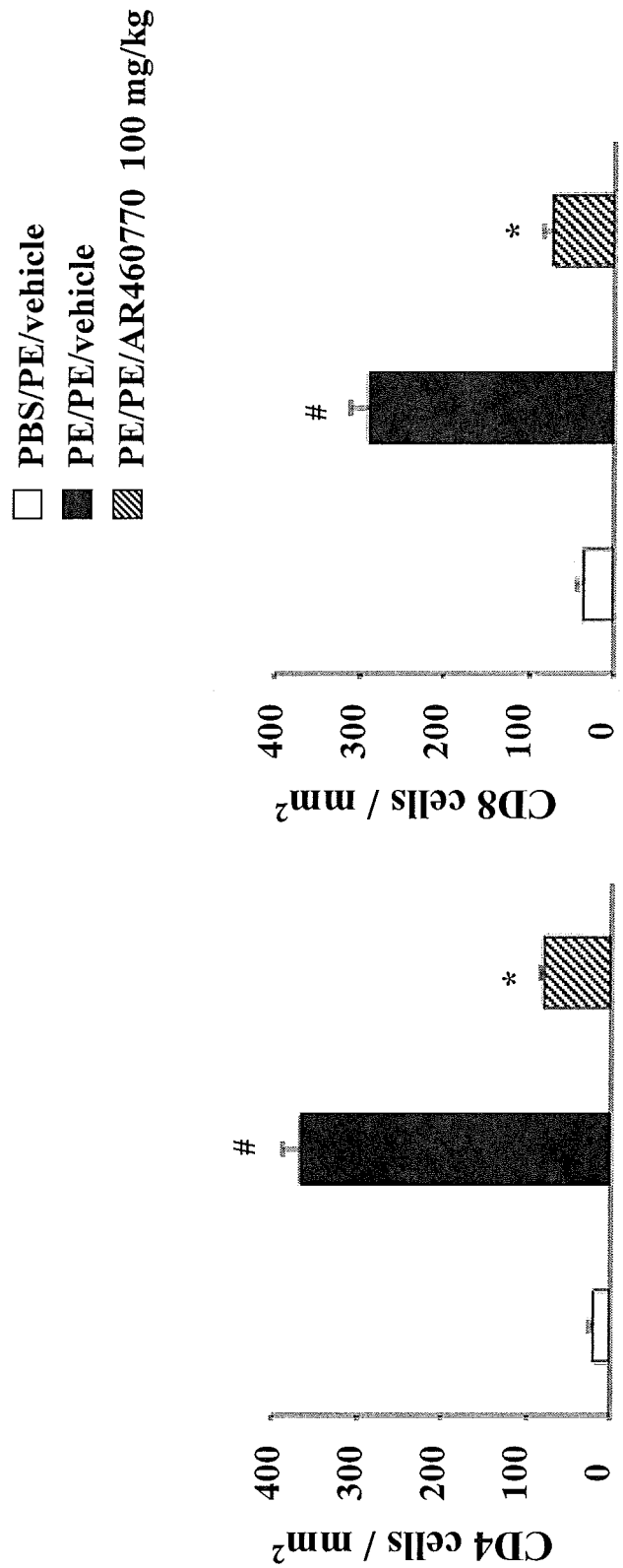

FIGS. 3A-3G shows inhibition of Pim1 kinase reduces intestinal responses. FIG. 3A shows the kinetics of development of diarrhea assessed 30 minutes after the last challenge in mice treated with or without AR460770. FIG. 3B shows the symptom scores as assessed 30 minutes after oral challenge. FIG. 3C shows the plasma levels of histamine as assessed within 30 minutes after the last oral challenge. FIG. 3D shows the quantitation of mucosal mast cell numbers in the jejunum using chloroacetate esterase staining. FIG. 3E shows the quantitation of mucosal eosinophil numbers in the jejunum using immunohistochemistry and anti-MBP antibody. FIG. 3F shows the quantitation of mucosal goblet cells numbers in the jejunal epithelium by PAS staining 24 hrs after the last challenge. For mast cells and eosinophils, results are expressed as the number of chloroacetate esterase- or anti-major basic protein-stained cells per square millimeter of lamina propria, respectively. For goblet cells, the number of $PAS^+$ cells was divided by the total number of epithelial cells in the villi. FIG. 3G shows the quantitative analysis of numbers of CD4 and CD8 T cells in jejunal tissue. Results are obtained from 3 independent experiments, and each experiment included 4 mice per group. #P<0.01 between PBS/PE/vehicle and PE/PE/vehicle groups. *P<0.01, **P<0.001 comparing vehicle-treated with AR460770-treated sensitized and challenged mice.

Figure 4A:
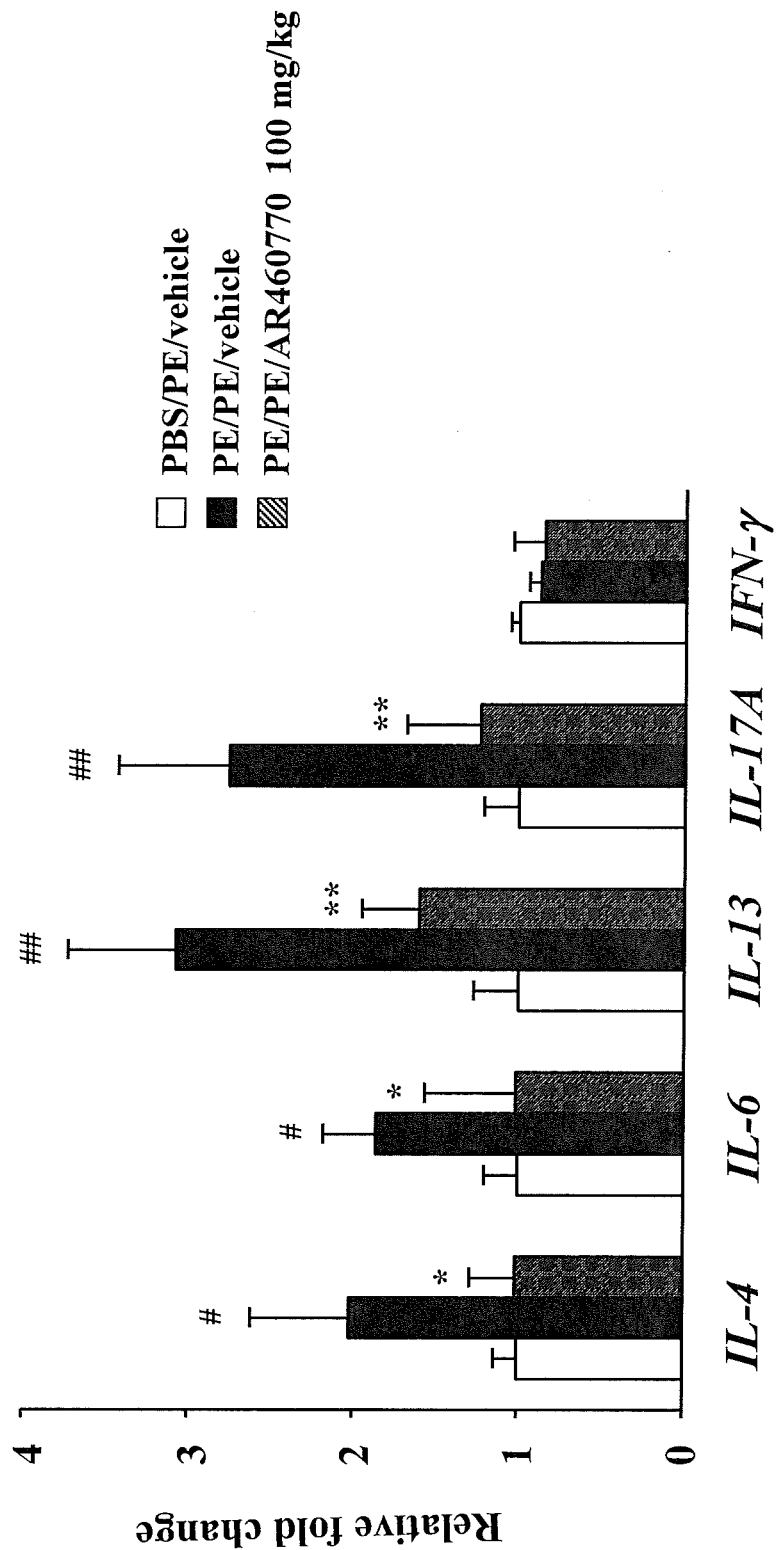
Figure 4B:
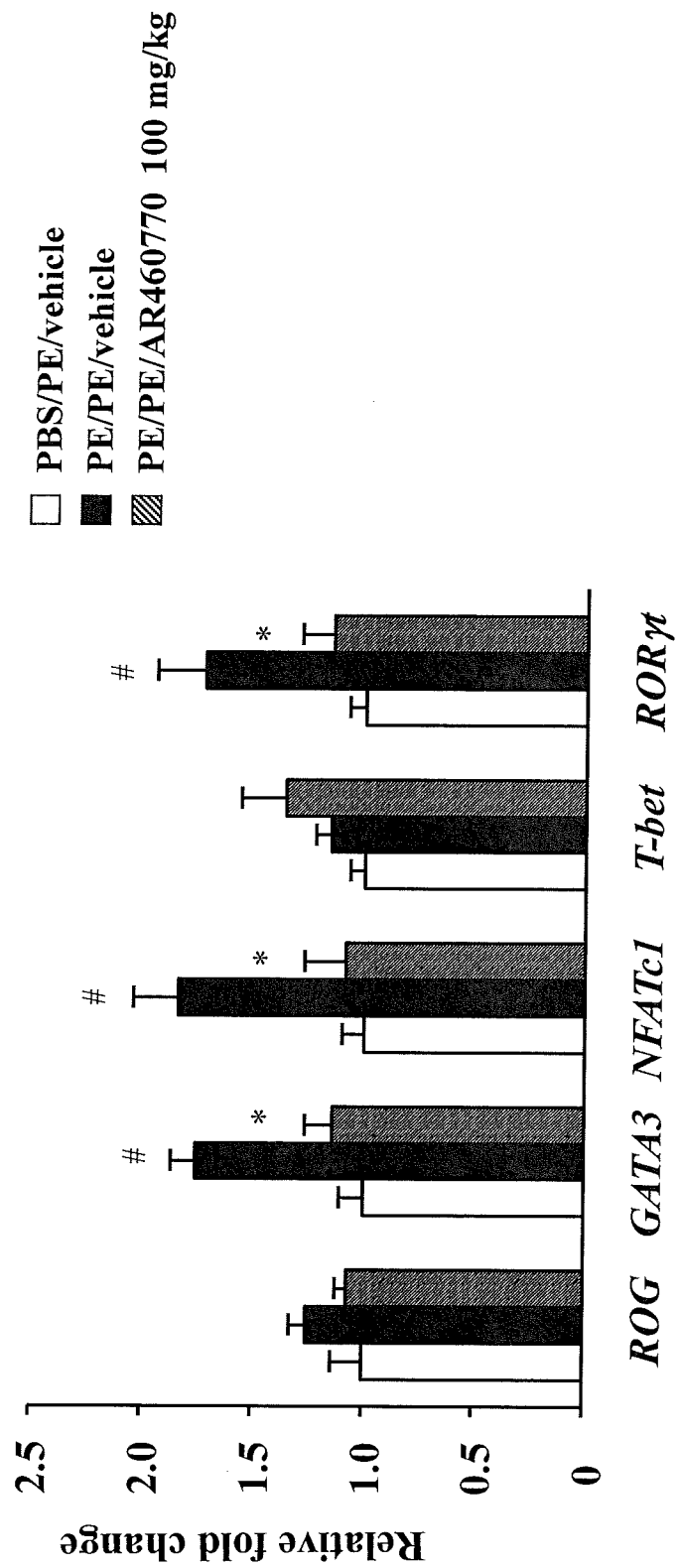
Figure 4C:
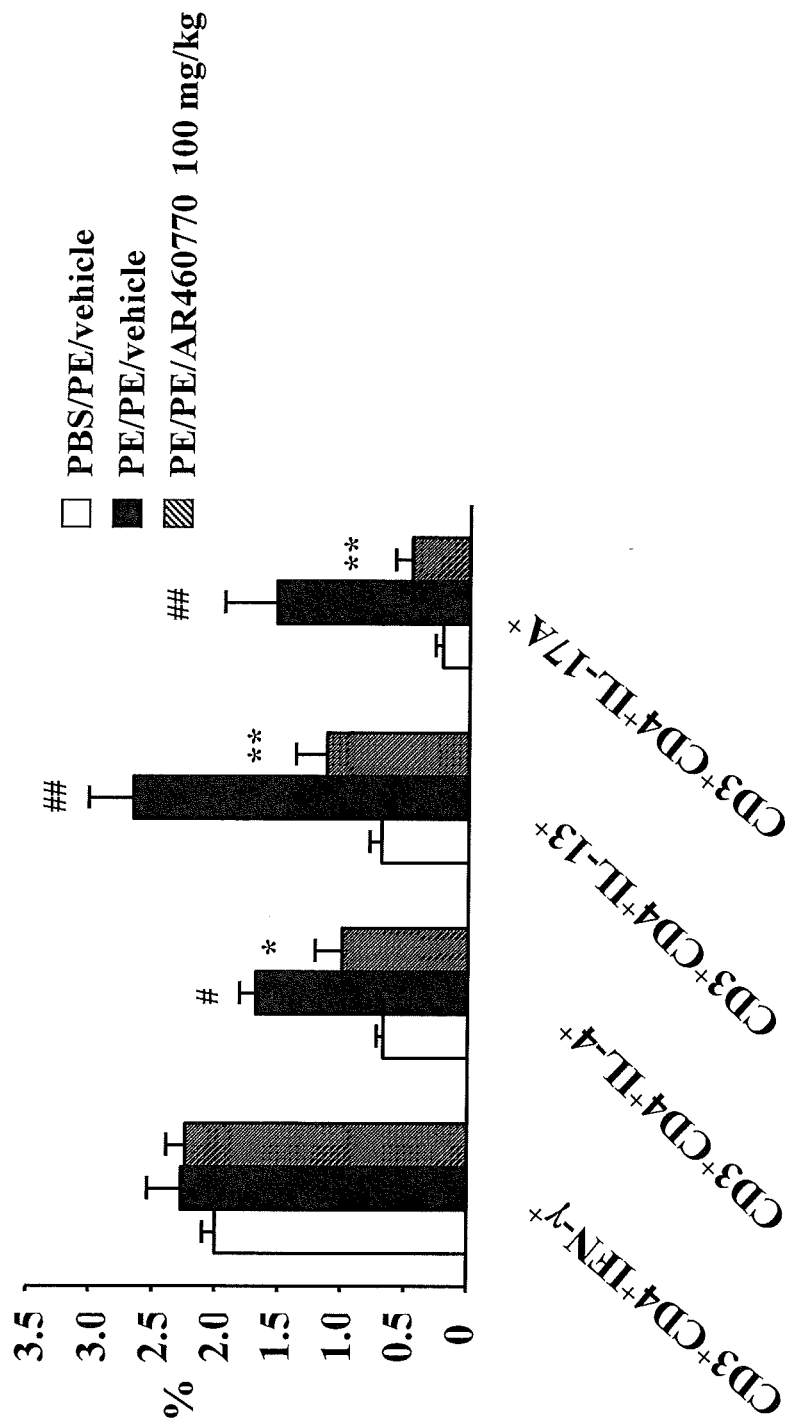

FIGS. 4A-4C shows the effect of inhibition of Pim1 kinase on cytokines and transcription factor expression. FIG. 4A shows the quantitative RT-PCR analysis of Th1, Th2, and Th17 cytokine mRNA expression in the jejunum of PBS/PE/vehicle mice and PE/PE mice treated with AR460770 or vehicle. FIG. 4B shows the key transcription factors for Th1, Th2, and Th17 cytokine expression levels in the jejunum of PBS/PE/vehicle mice and PE/PE mice treated with AR460770 or vehicle. Relative mRNA expression levels of T-bet, ROG, GATA3, NFATc1, and RORγt in the jejunum determined by quantitative RT-PCR. FIG. 4C shows the percentage of IFN-$\gamma^+$CD3$^+$CD4$^+$, IL-4$^+$CD3$^+$CD4$^+$, IL-13$^+$CD3$^+$CD4$^+$ and IL-17A$^+$CD3$^+$CD4$^+$ cells in the MLN of PBS/PE/vehicle mice and PE/PE mice treated with the inhibitor or vehicle. The data shown are representative of 3 independent experiments. #P<0.05; ##P<0.01 between PBS/PE/vehicle and PE/PE/vehicle groups (n=12). *P<0.05; **P<0.01 between PE/PE mice treated with AR460770 (100 mg/kg) and vehicle.

Figure 5A:
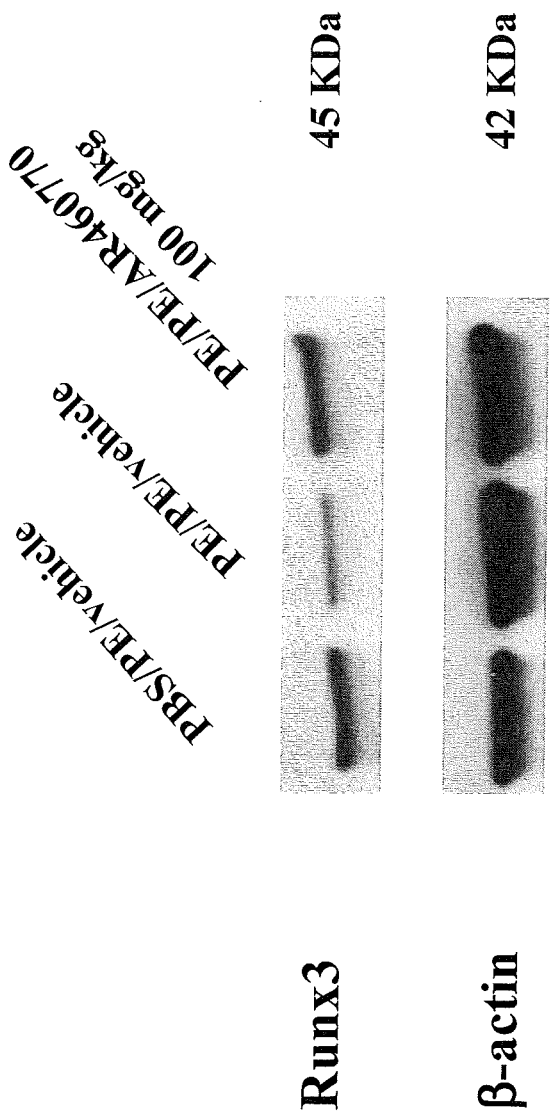
Figure 5B:
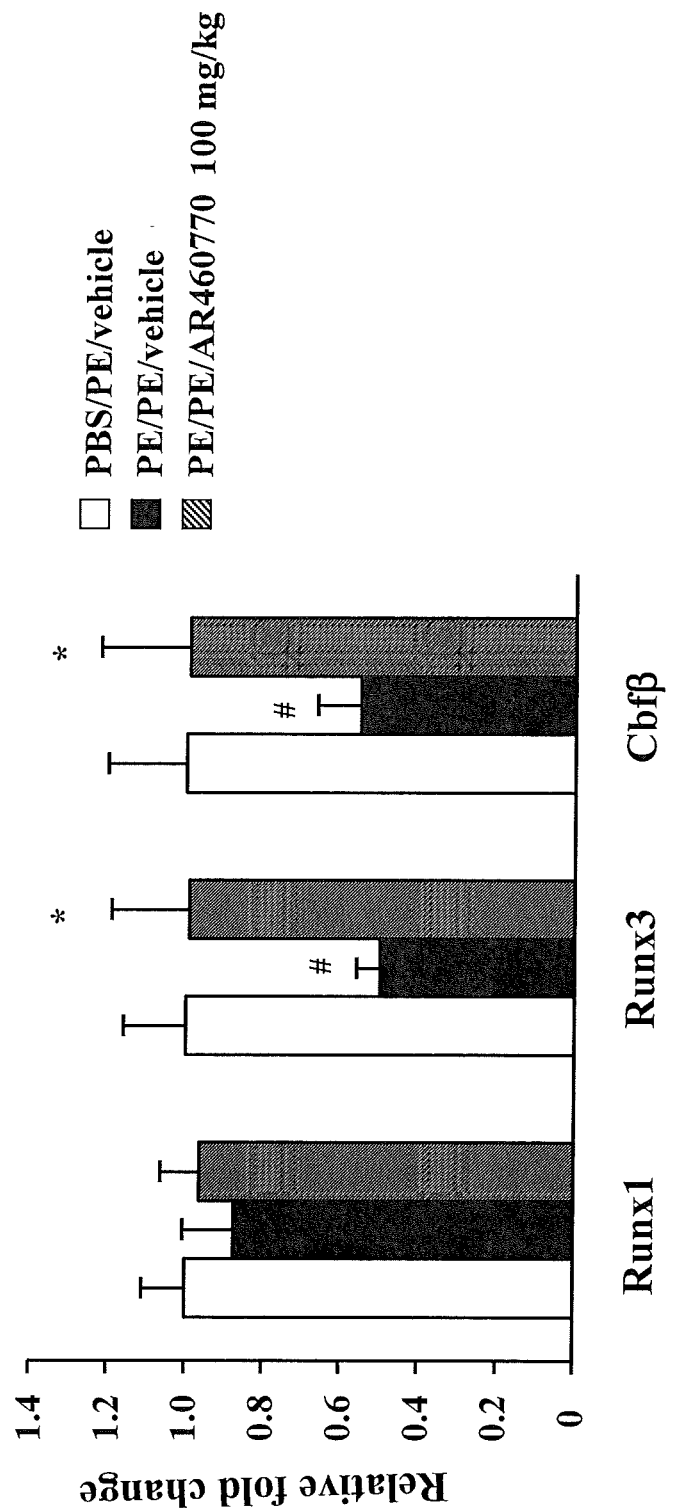
Figure 5C:
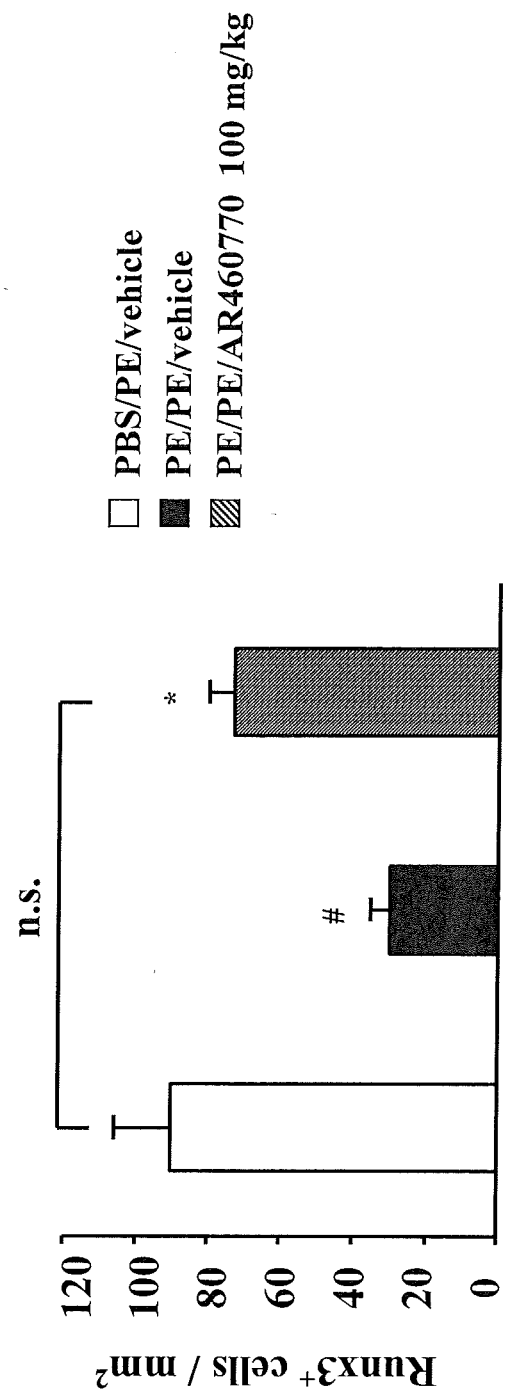
Figure 5D:
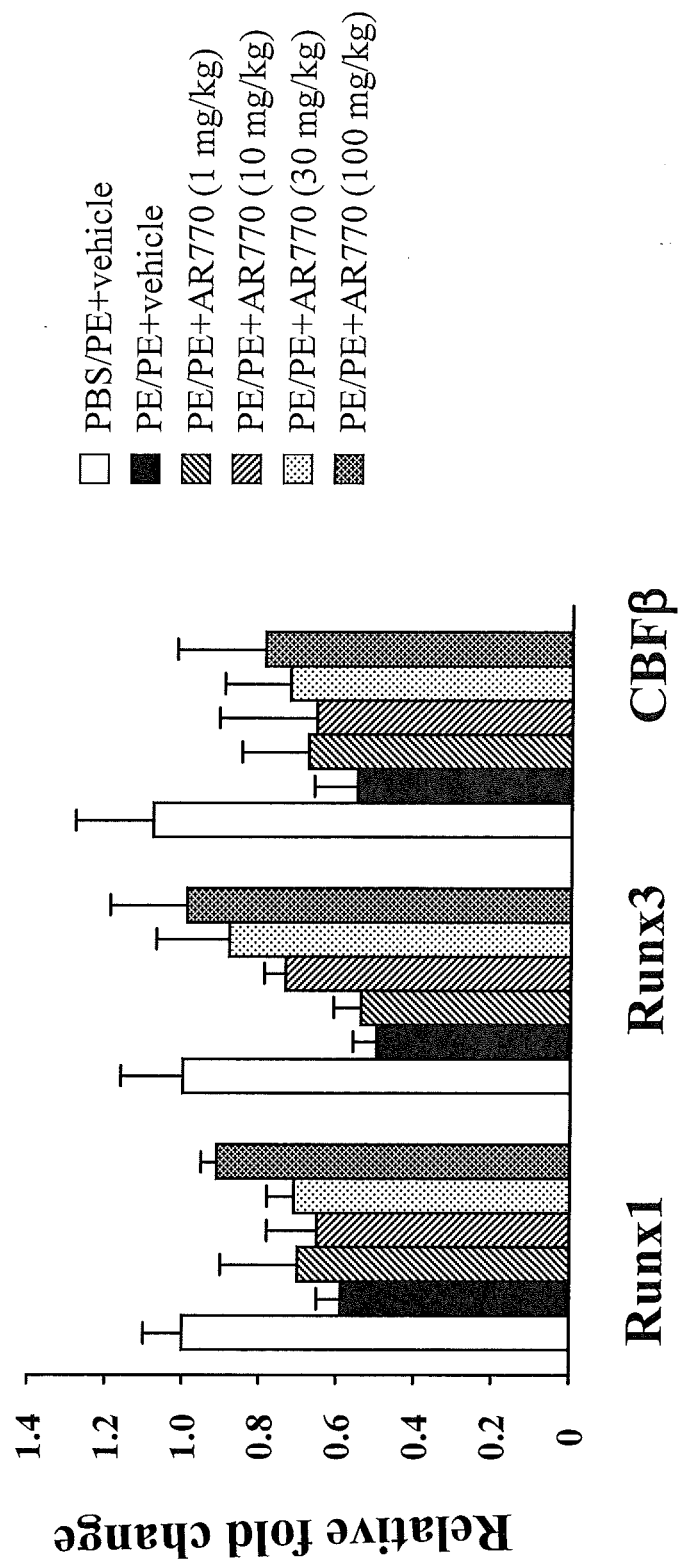

FIGS. 5A-5D show Pim1 kinase regulates Runx3 transcription factor expression in intestine. FIG. 5A shows Runx3 protein is upregulated by Pim1 kinase inhibitor treatment in the jejunum of PE/PE mice. Representative Western blots show Runx3 in jejunal extracts from PBS/PE/vehicle mice and PE/PE mice treated with or without AR460770 analyzed for the expression of Runx3, β-actin was used as a loading control. A representative of 3 independent experiments is shown. FIG. 5B shows the quantitative RT-PCR analysis of the induction of Runx mRNA expression in the jejunum of PBS/PE/vehicle mice and PE/PE mice treated with or without AR460770. FIG. 5C shows the quantitation of mucosal Runx3-positive cell numbers in the jejunum. Results are expressed as the number of Runx3-stained cells per square millimeter of lamina propria. Results are from 3 independent experiments with 4 mice per group. #P<0.01 between PBS/PE/vehicle and PE/PE/vehicle groups. *P<0.01 between PE/PE mice treated with AR460770 and control vehicle. FIG. 5D: Runx1, Runx3 and Cbf β (core binding factor beta; a transcriptional co-activator that is known to enhance DNA-binding of Runx proteins) mRNA expression was detected in the intestine of mice. Non-sensitized peanut challenged mice are indicated by "PBS/PE". Sensitized-peanut challenged mice are indicated by "PE/PE" and peanut challenged mice treated with the Pim1 kinase inhibitor is indicated as "PE/PE+ AR770": 1 mg/kg, 10 mg/kg, 30 mg/kg or 100 mg/kg.

Figure 6A:
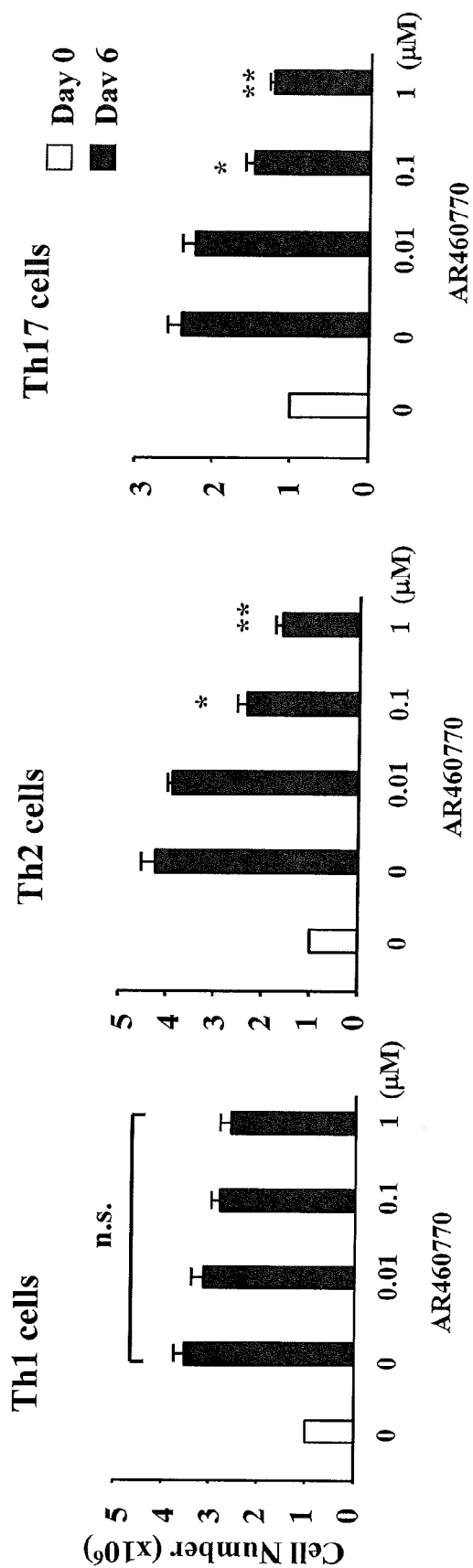
Figure 6B:
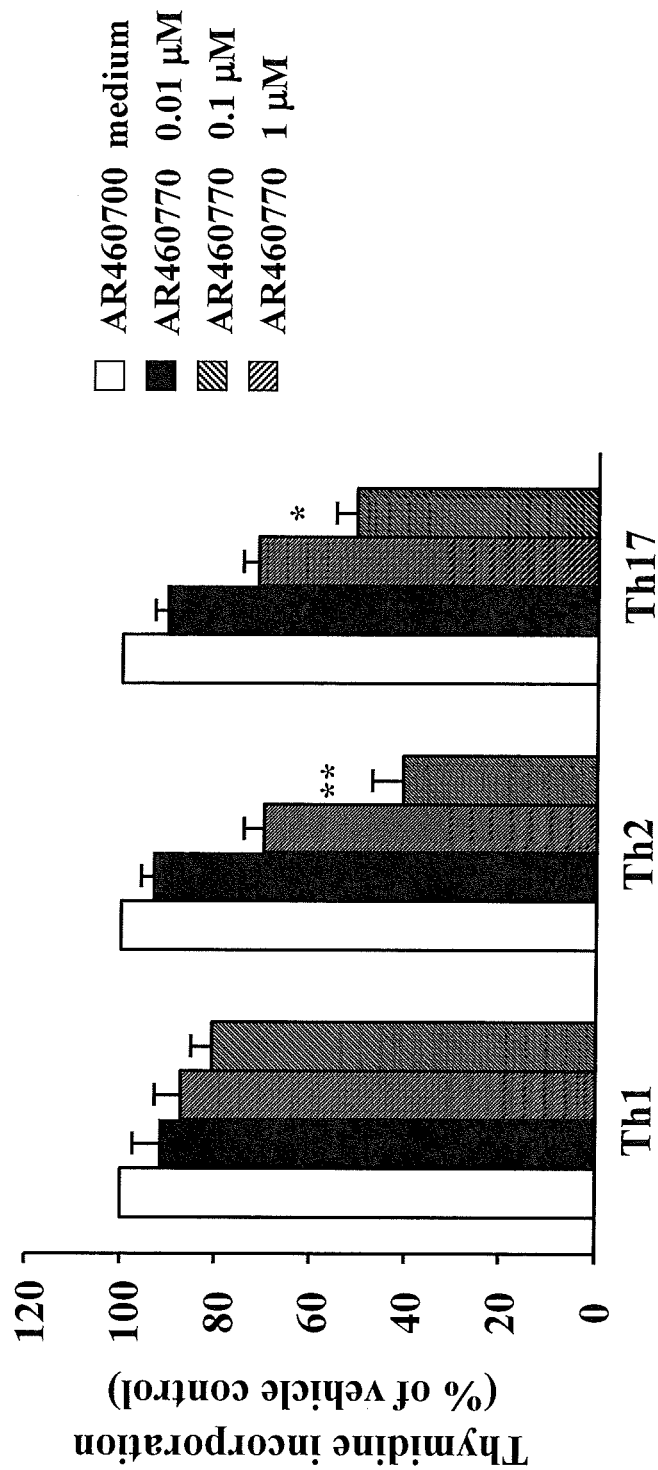
Figure 6C:
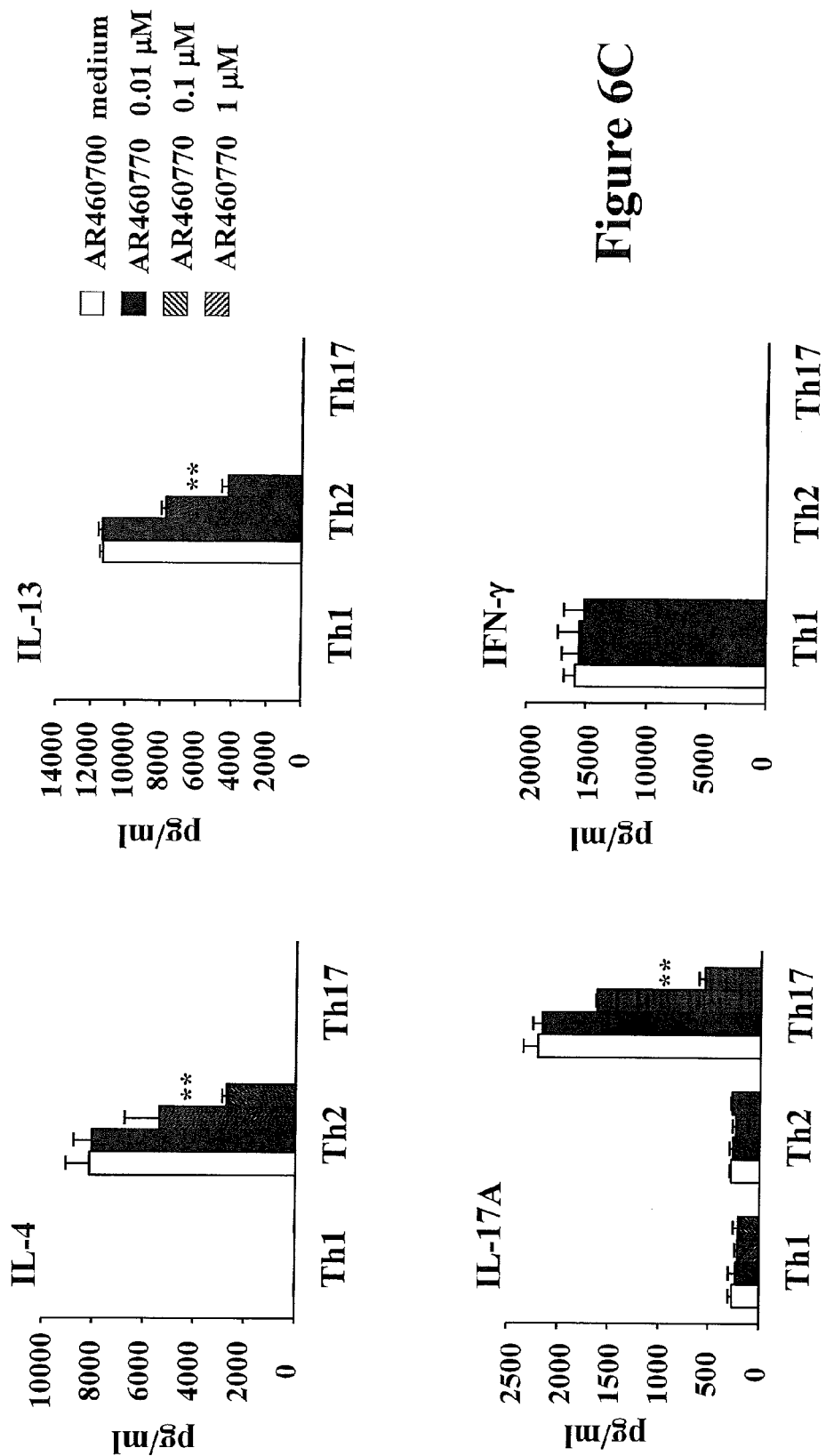
Figure 6D:
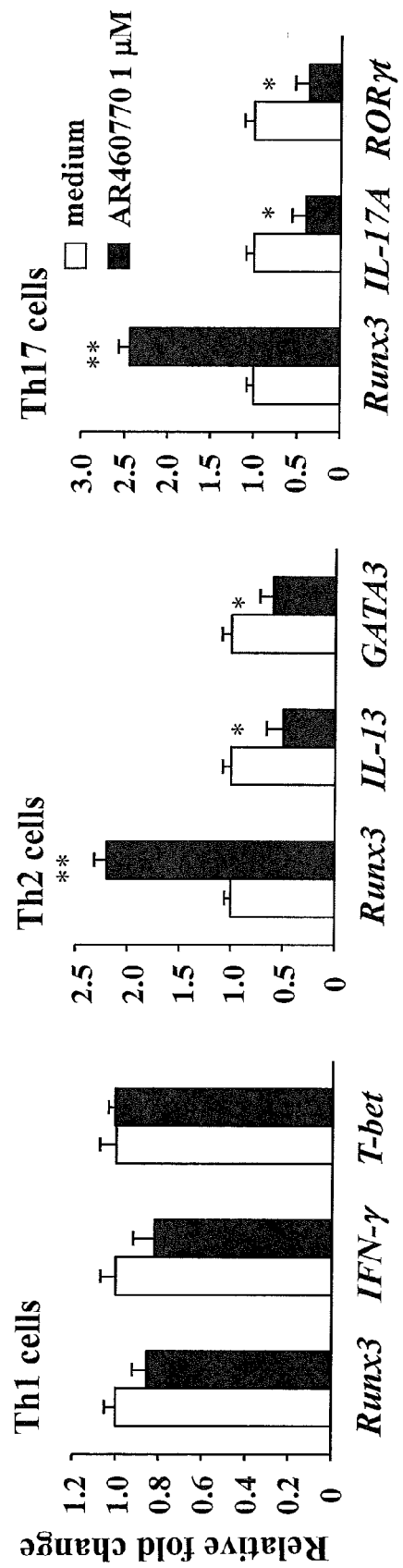
Figure 6E:
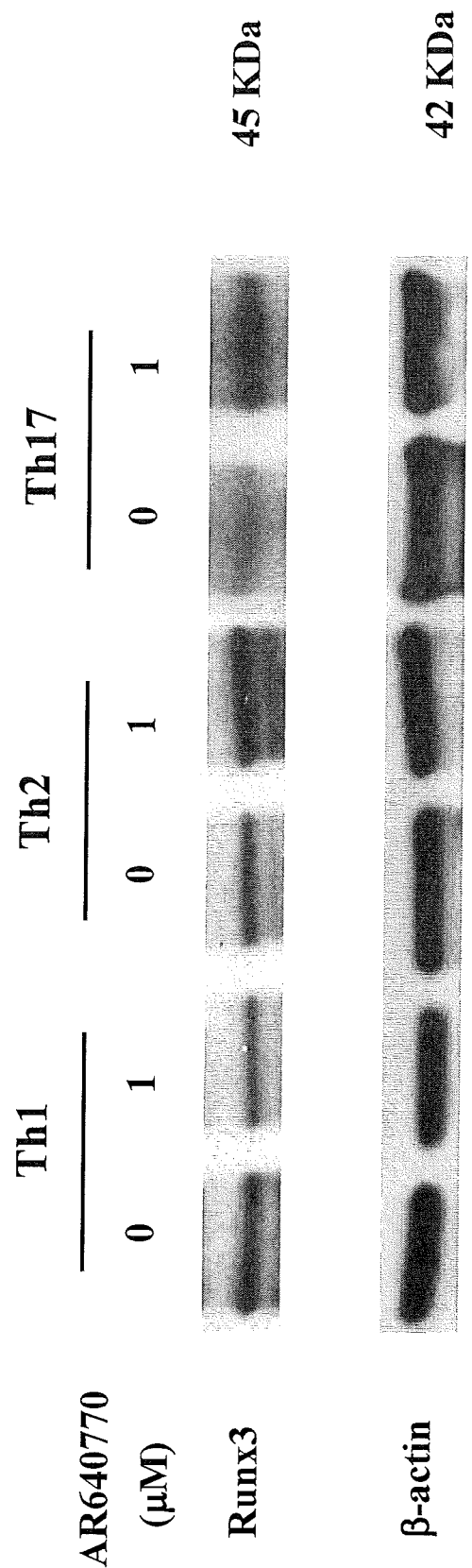

FIGS. 6A-6E show Pim1 kinase inhibitor modulates Runx3 expression and suppresses the differentiation of naive CD4 T cells into the Th2 and Th17 lineage in vitro. FIG. 6A shows the cell proliferation reported as number of cells. FIG. 6B shows the cell proliferation as measured by $^3$H-thymidine incorporation (cpm) and expressed as a % of the vehicle-treated group. FIG. 6C shows the levels of cytokine production in the supernatants of cultured CD4 T cells. CD4 T cells were cultured under Th1, Th2, and Th17 polarizing conditions in the presence or absence of the inhibitor for 6 days after which the cells were stimulated with anti-CD3 and anti-CD28 for 24 hrs and supernatants were collected and assayed for cytokines by ELISA. FIG. 6 D shows Pim1 kinase regulates Runx3 and cell-specific transcription factor mRNA expression in naive CD4 T cells differentiated in vitro into Th2 or Th17 cells as shown by quantitative RT-PCR. FIG. 6E shows a western blot analysis of Runx3 protein levels in the polarized Th1, Th2, and Th17 cells. The cells were cultured as previously described in FIG. 6C and on day 6 cells were lysed and processed for Western blot analysis with anti-Runx3. β-actin was used as a loading control. A representative Western blot from one of 3 similar experiments is shown. For other panels, results are from 3 independent experiments, 4 mice/group (n=12). *P<0.05; **P<0.01 comparing vehicle-treated and AR460770 treated-cells. NS: nonsignificant comparing vehicle-treated and AR460770 treated-cells.

Figure 7A:
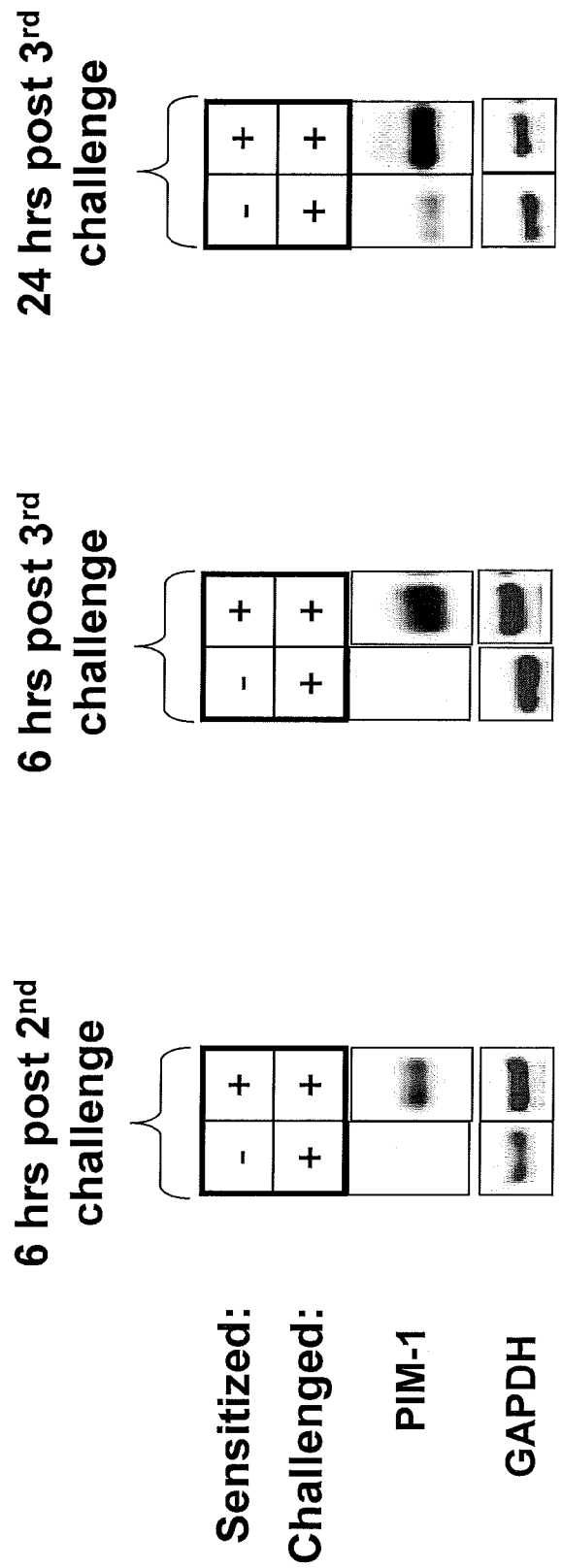
Figure 7B:
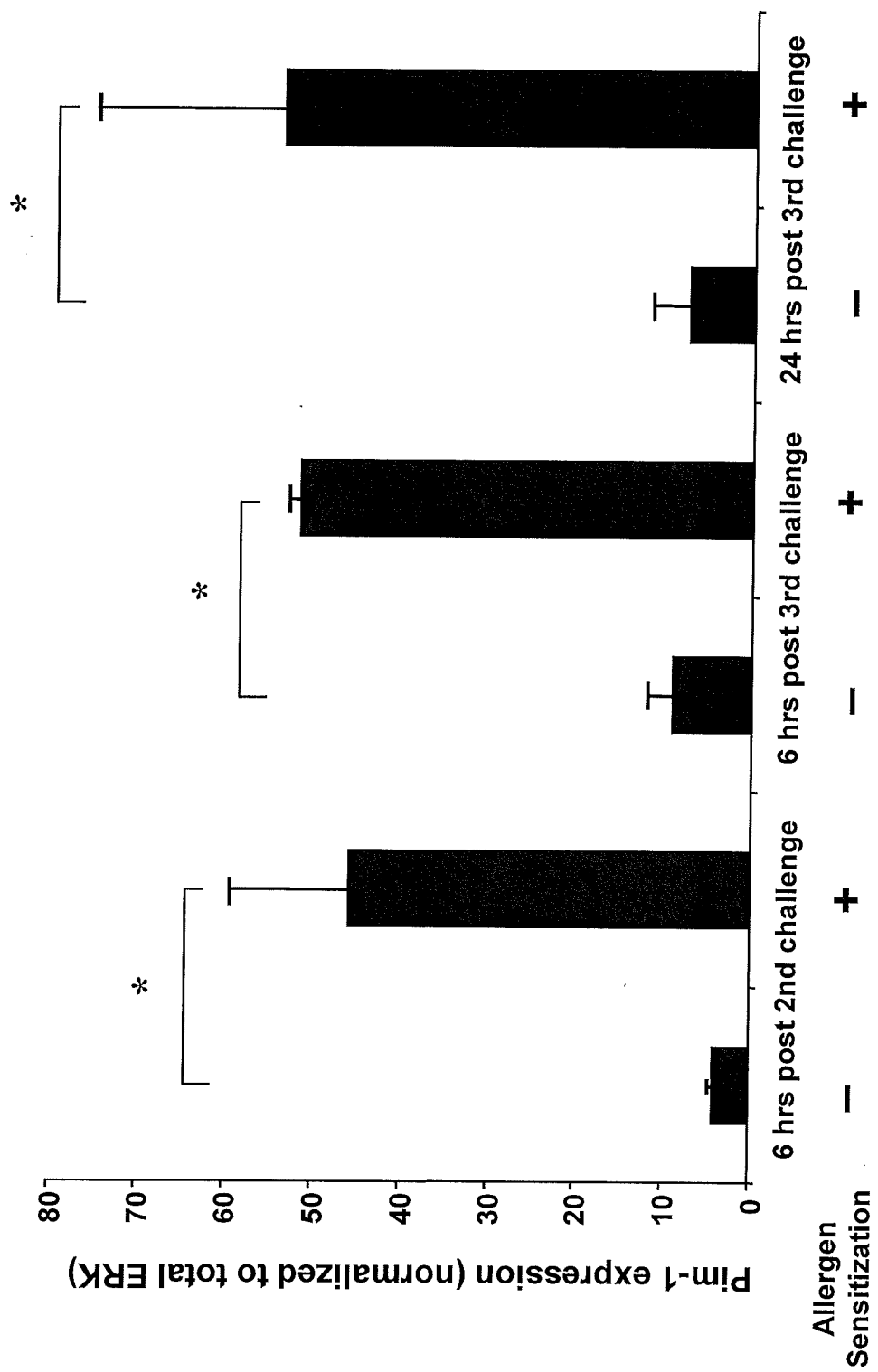

FIGS. 7A-7B show the expression levels of Pim1 kinase in lungs following OVA sensitization and challenge. Pim1 kinase levels were determined by Western blot in lungs of mice which were sensitized and challenged with OVA or received sham sensitization and OVA challenge. Expression levels were examined at three time points: 6 hrs after the second OVA challenge, 6 hrs after the third OVA challenge, and 24 hrs after third OVA challenge. Experiments were repeated at least 3 times. GAPDH was used as a loading control (FIG. 7A) and the average optical densitometry was expressed by standardizing to total ERK (FIG. 7B).

Figure 8A:
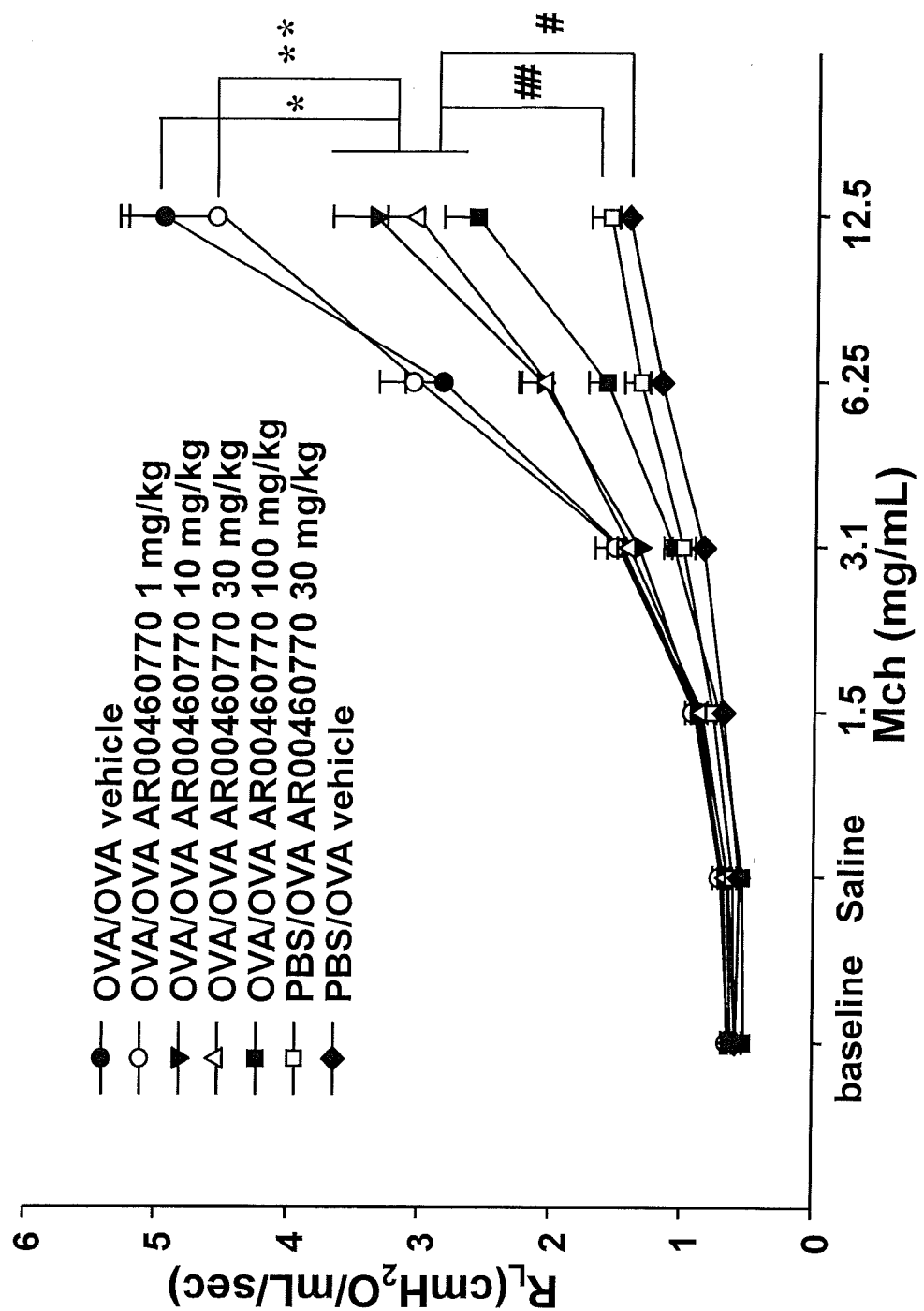

FIGS. 8A-8E show the effect of Pim1 kinase inhibition on airway responses following primary allergen challenge. The effects of a Pim1 kinase inhibitor were determined in the primary allergen challenge model. (FIG. 8A) Changes in pulmonary resistance (RL) in response to increasing doses of methacholine (MCh), (FIG. 8B) Cell composition in BAL fluid. Macro; macrophages, Lympho; lymphocytes, Eos; eosinophils, Neu; neutrophils. (FIG. 8C) BAL fluid cytokine levels. (FIG. 8D1) Lung tissue histology following staining with hematoxylin and eosin (H&E) followed by quantitative analysis (FIG. 8D2). (FIG. 8E1) periodic acid-Schiff (PAS) followed by quantitative analysis (FIG. 8E2). Quantitative analysis of inflammatory and $PAS^+$ cells in lung tissue was performed as described in Materials and Methods. Mice were sham sensitized followed by OVA challenge (PBS/OVA) or sensitized and challenged with OVA (OVA/OVA). Pim1 inhibitor, AR00460770, was administered at doses of 1, 10, 30, or 100 mg/kg. Control groups received vehicle. (n=8). *p<0.05; compared to OVA/OVA vehicle. #p<0.05; compared to PBS/OVA vehicle. **p<0.05; compared to OVA/OVA AR00460770 1 mg/kg. ##p<0.05; compared to PBS/OVA AR00460770 30 mg/kg.

FIGS. 9A-9E show the effect of Pim1 kinase inhibition on airway responses in the secondary allergen challenge model.

Figure 9A:
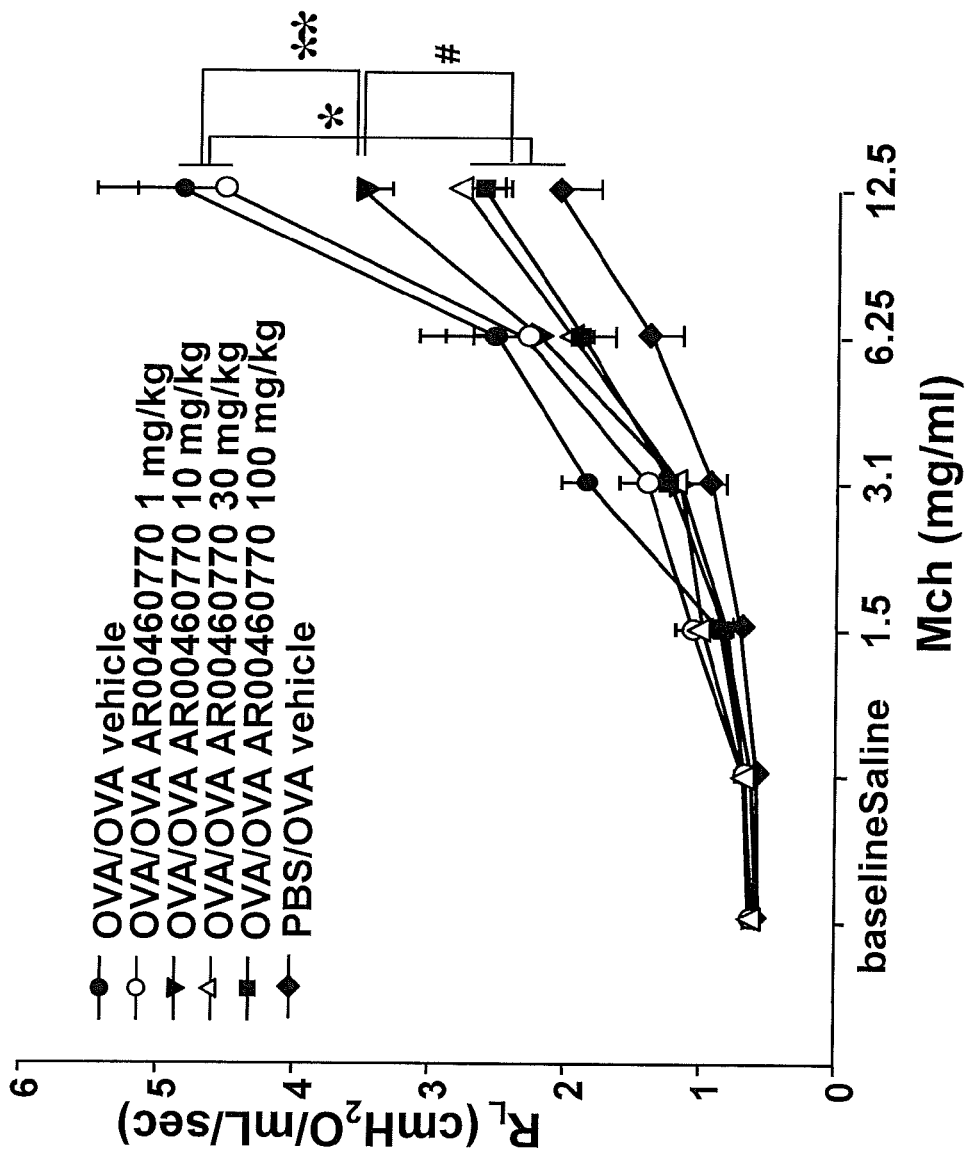

The effects of Pim1 kinase inhibition were determined in the secondary allergen challenge model. (FIG. 9A) Changes in pulmonary resistance (RL) in response to increased dose of methacholine (MCh), (FIG. 9B) Cell composition in BAL fluid, (FIG. 9C) BAL fluid cytokine levels, (FIG. 9D1) lung tissue histology following staining with hematoxylin and eosin (H&E)) followed by quantitative analysis (FIG. 9D2). (FIG. 9E1) periodic acid-Schiff (PAS) followed by quantitative analysis (FIG. 9E2). Quantitative analysis of inflammatory and goblet cells was as described in Materials and Methods. Mice were sham sensitized followed by OVA challenge (PBS/OVA) or sensitized and challenged with OVA (OVA/OVA). Pim1 inhibitor was administered at doses of 1, 10, 30, or 100 mg/kg. Control groups received vehicle. (n=8). *$p<0.05$; compared to OVA/OVA vehicle or OVA/OVA AR00460770 1 mg/kg. #$p<0.05$ compared to OVA/OVA AR00460770 10 mg/kg. **$p<0.05$ compared to OVA/OVA vehicle or OVA/OVA AR00460770 1 mg/kg.

Figure 10:
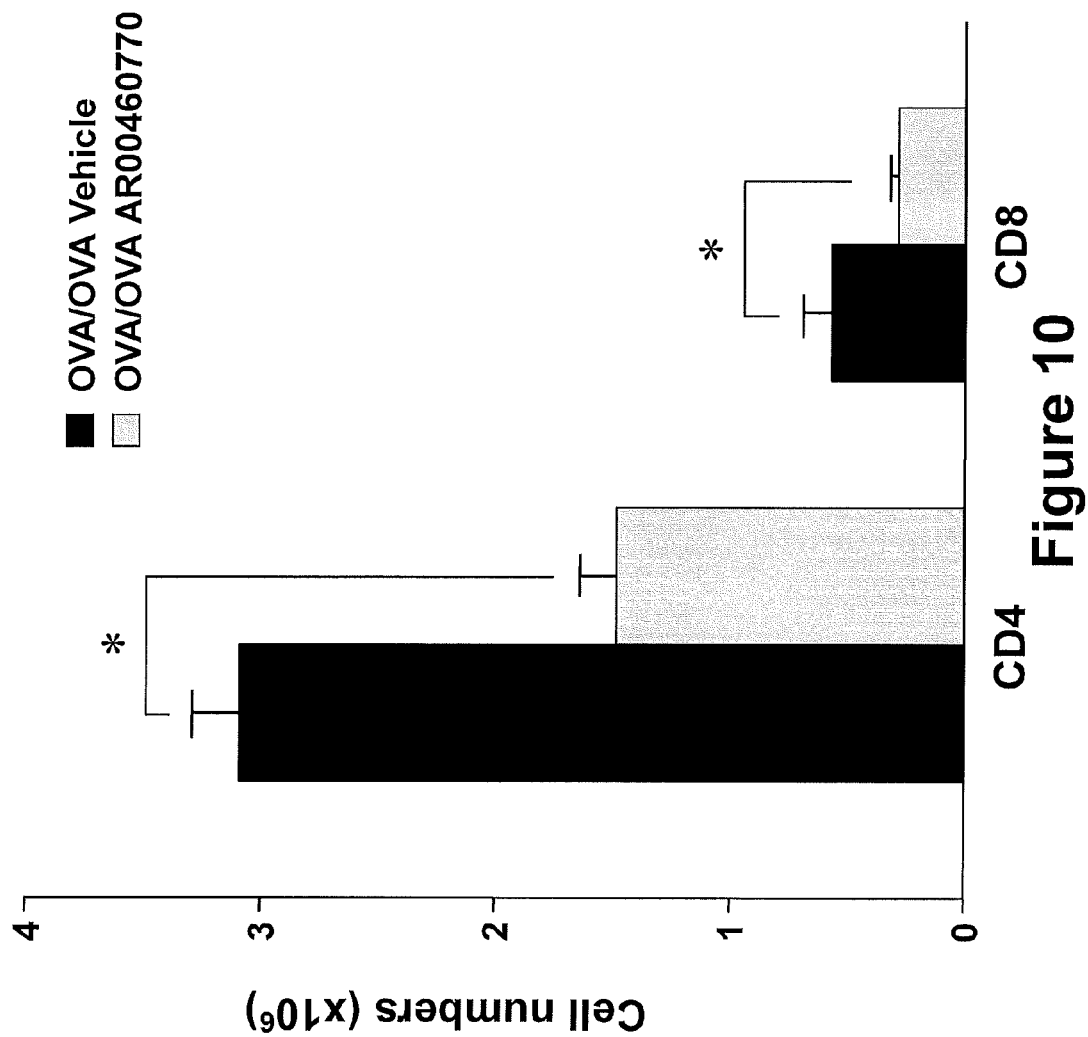

FIG. 10 shows the effects of Pim kinase inhibition on numbers of $CD4^+$ and $CD8^+$ T cells. In OVA sensitized and challenged mice, the numbers of $CD4^+$ T cells (CD4) and $CD8^+$ T cells (CD8) in the lungs of mice treated with a Pim1 kinase inhibitor (OVA/OVA AR00460770) or vehicle (OVA/OVA vehicle) were determined. MNCs isolated from lungs were stained with anti-CD3, anti-CD4, and anti-CD8 for flow cytometry analysis as described in Materials and Methods. The data shown were representative of 3 independent experiments. *$p<0.05$ compared to vehicle.

FIGS. 11A-11C show the effect of Pim1 kinase inhibition on cell proliferative responses and cytokine production from $CD4^+$ and $CD8^+$ T cells. Purified spleen $CD4^+$ and $CD8^+$ T cells were preincubated with the Pim1 kinase inhibitor followed by anti-CD3 and anti-CD28 stimulation. FIG. 11A shows the cell proliferation assays carried out 24 hrs after anti-CD3/anti-CD28 stimulation and calculated from the uptake of tritium-labeled thymidine. (n=8). FIG. 11B shows the quantitation of cytokine levels in supernates from anti-CD3/anti-CD28 stimulated $CD4^+$ and in FIG. 11C $CD8^+$ T cells. CPM; count per minutes. *$p<0.05$; compared to vehicle-treated cells.

DETAILED DESCRIPTION OF THE INVENTION

The present invention generally relates to methods of treating an allergic condition in a subject who has or who is at risk of having the allergic condition. In a preferred embodiment, the method comprises administering a composition that inhibits Pim1 kinase. In still another preferred embodiment, the method comprises administering a composition that induces Runx3 expression.

The inventors have identified a critical role of Pim1 kinase in the development of allergic conditions. In particular, inhibition of Pim1 kinase effectively reduces the development of a full spectrum of allergen-induced responses, including lung inflammatory responses and intestinal inflammatory response at least in part through limiting the expansion and activities of effector $CD4^+$ and $CD8^+$ T cells. As such, inhibition of Pim1 kinase expression and/or activity represents a novel therapeutic target in the treatment of various allergic conditions.

The inventors have also identified a critical role of Runx3 in the development of allergic conditions. In particular, loss of Runx3 results in the development of atopy. In addition, the inventors have determined that Runx3 mRNA and protein levels are decreased following allergen sensitization and challenge. In turn, Runx3 mRNA and protein levels are increased when tolerance to an inciting allergen is induced and is associated with decreased mast cell, eosinophil, and goblet cell accumulation in the tissues as well as decreases in Th2 cytokine production, thus providing that Runx3 plays an important role in regulating the development of allergy.

More particularly, the inventors have shown that Pim1 kinase is essential to the development of peanut-induced intestinal allergy. Inhibition of Pim1 kinase prevented peanut-induced diarrhea and intestinal inflammation in vivo as well as impairing Th2 or Th17 cell differentiation in vitro by enhancing Runx3 expression and repressing nuclear factor of activated T-cells cytoplasmic 1 (NFATc1) expression (the transcriptional activity of NFATc1 is enhanced by Pim1 kinase (Wang, M., et al. 2010. J. Allergy Clin. Immunol. 126:306-316).

In addition the inventors have determined that following administration of a Pim1 kinase inhibitor to sensitized and challenged mice, all of the clinical manifestations of the disease/condition and the accumulation of mast cells, and eosinophils in the tissues were prevented. In particular, the decreases in Runx3 expression were also prevented. Therefore, the data identify the transcription factor Runx3 as an upstream convergence point involved in the regulation of atopy development and is responsible for the protection against disease through induction of tolerance. Targeting the regulation of Runx3 expression represents a novel approach for the prevention of allergic conditions and inhibition of Pim1 kinase expression and/or activity is a means for achieving repression of allergic responses through induction (i.e. upregulation) or sustaining expression of Runx3.

As described in the examples below, together with results which demonstrate the reduction of both Th2 and Th1 cytokines in BAL fluid and the reduction of both $CD4^+$ and $CD8^+$ T cells following Pim inhibitor treatment, concerns that the suppressive effects of Pim kinase inhibition on allergen-induced airway responses were due to its toxic effects on immune cells were considered. However, as the cell numbers and viability were not altered in in vitro cultures of $CD4^+$ and $CD8^+$ T cells with up to 10 μM of the inhibitor, the effects on airway responses were not likely induced by drug-mediated cell toxicity. Furthermore, Pim inhibitor treatment in sham-sensitized but OVA-challenged mice did not alter airway responsiveness to MCh, further indicating that the Pim inhibitor did not exhibit toxic effects on lung resident cells, including airway smooth muscle.

In addition, the inventors have determined that Pim1 kinase inhibition alters the activities of the $CD4^+$ and $CD8^+$ T effector cells in airways, and determined that the numbers of $CD4^+$ and $CD8^+$ T cells in the lungs are dramatically decreased in Pim inhibitor-treated, sensitized and challenged mice. Further, in in vitro experiments Pim inhibitor treatment demonstrates suppressive effects on the cell proliferation of $CD4^+$ and $CD8^+$ T cells in response to stimulation with anti-CD3 and anti-CD28. These results show that the of inhibition of Pim1 kinase limits responses through interference with the expansion of critical effector cells, $CD4^+$ and $CD8^+$ T cells in the airways, and possibly eosinophils.

According to the present invention, allergic conditions, include but are not limited to pulmonary conditions such as allergic rhinitis, asthma, airway hyperresponsiveness, and hay fever as well as other allergic conditions including but not limited to a food allergy, eosinophilic esophagitis, chronic urticaria, atopic dermatitis, occupational allergy, allergic conjunctivitis, airborne allergic sensitivities, stinging insect allergy, hypersensitivity pneumonitis, eosinophilic lung diseases, inflammatory bowel disease, ulcerative colitis, Crohn's disease and drug allergies. More specifically, symptoms of the allergies, including but not limited to diarrhea and intestinal inflammation as well as asthma and airway hyperresponsiveness, is apparently or obviously, directly or indirectly triggered by an allergen to which a subject has previously been sensitized. Sensitization to an allergen refers to being previously exposed one or more times to an allergen such that an immune response is developed against the allergen. Responses associated with an allergic reaction (e.g., histamine release, edema, vasodilatation, bronchial constriction, airway inflammation, airway hyperresponsiveness, asthma, allergic rhinitis (hay fever), nasal congestion, sneezing, running nose, skin rash, diarrhea including acute allergic diarrhea and intestinal inflammation), typically do not occur when a naive subject is exposed to the allergen for the first time, but once a cellular and humoral immune response is produced against the allergen, the subject is "sensitized" to the allergen. Allergic reactions then occur when the sensitized individual is re-exposed to the same allergen (e.g., an allergen challenge). Once a subject is sensitized to an allergen, the allergic reactions can become worse with each subsequent exposure to the allergen, because each re-exposure not only produces allergic symptoms, but further increases the level of antibody produced against the allergen and the level of T cell response against the allergen.

According to the present invention, inflammation is characterized by the release of inflammatory mediators (e.g., cytokines or chemokines) which recruit cells involved in inflammation to a tissue. A condition or disease associated with allergic inflammation is a condition or disease in which the elicitation of one type of immune response (e.g., a Th2-type immune response) against a sensitizing agent, such as an allergen, can result in the release of inflammatory mediators that recruit cells involved in inflammation in a subject, the presence of which can lead to tissue damage and sometimes death. A Th2-type immune response is characterized in part by the release of cytokines which include IL-4, IL-5, IL-13 and IL-17. The present invention is particularly useful for treating allergen-induced food allergies (such as peanut allegories) and airway hyperresponsiveness and airway inflammation, including, allergen-induced asthma and rhinitis.

Accordingly, various embodiments of the present invention include treating a patient that has been sensitized to an allergen and has been or is at risk of becoming exposed to the allergen. Such allergens can be related to a food, a plant, a gas, a pathogen, a metal, a glue or a drug. Examples of food allergens include but are not limited to groundnuts such as peanuts; nuts from trees including Brazilian nuts, hazelnuts, almonds, walnuts; fruit, milk, eggs, fish, shellfish, wheat, or gluten. Examples of plant allergens include but are not limited to pollen, trees, grass, weeds, ragweed, poison Oak or poison ivy. Examples of gas allergens include but are not limited to environmental tobacco smoke, and carbon monoxide. Examples of pathogen allergens include but are not limited to mold, viruses or bacteria. Examples of metal allergens include but are not limited to lead, nickel, chromate, or cobalt. Examples of drug allergens include but are not limited to penicillin, sulfur, or aspirin. Additional allergens include but are not limited to latex, dust mites, pet dander (skin flakes), droppings from cockroaches, rodents and other pests or insects.

According to the present invention, "airway hyperresponsiveness" or "AHR" refers to an abnormality of the airways that allows them to narrow too easily and/or too much in response to a stimulus capable of inducing airflow limitation. AHR can be a functional alteration of the respiratory system resulting from inflammation in the airways or airway remodeling (e.g., such as by collagen deposition). Airflow limitation refers to narrowing of airways that can be irreversible or reversible. Airflow limitation or airway hyperresponsiveness can be caused by collagen deposition, bronchospasm, airway smooth muscle hypertrophy, airway smooth muscle contraction, mucous secretion, cellular deposits, epithelial destruction, alteration to epithelial permeability, alterations to smooth muscle function or sensitivity, abnormalities of the lung parenchyma and infiltrative diseases in and around the airways. Many of these causative factors can be associated with inflammation. AHR can be triggered in a patient with a condition associated with the above causative factors by exposure to a provoking agent or stimulus. Such stimuli include, but are not limited to, an allergen.

According to the present invention, treatment of a subject having an allergic condition can commence as soon as it is recognized (i.e., immediately) by the subject or by a clinician that the subject has been exposed or is about to be exposed to an allergen. Treating the subject can comprise administering a composition including but not limited to a small molecule inhibitor, an antibody, a chemical entity, a nucleotide, a peptide or a protein that inhibits Pim kinase. Inhibiting Pim kinase includes both direct inhibition of the kinase as well as inhibition of the expression of the kinase. Inhibition of a Pim kinase can be by any mechanism, including, without limitations, decreasing activity of the Pim kinase, increasing inhibition of Pim kinase, degradation of Pim kinase, a reduction or elimination of expression of Pim kinase. For example, the action of Pim kinase can be decreased by blocking or reducing the production of Pim kinase, "knocking out" the gene encoding Pim kinase, reducing Pim kinase activity, or inhibiting the activity of Pim kinase. Additionally, binding to Pim kinase to prevent its wild-type enzymatic activity, including competitive and noncompetitive inhibition, inhibiting transcription, and regulating expression can also inhibit Pim kinase. Small molecule inhibitors include but are not limited to a Pim1 kinase inhibitor, a Pim2 kinase inhibitor, and a Pim3 kinase inhibitor. Various Pim1 kinase inhibitors include but are not limited to AR460770 (also referred to as AR00460770, ARRY770 and AR770; ARRAY Biopharma), AR440 (ARRAY Biopharma), SimI4A, staurosporine, bisindolylmaleimide or triazolopyridine Pim kinase inhibitor compounds (as described for example in U.S. Patent Publication Nos. US2011/014485 and US2011/0144100). In one embodiment an antibody prevents or inhibits expression and/or activity of a Pim kinase. In one aspect, the antibody prevents or inhibits expression and/or activity of Pim1 kinase.

In accordance with the present invention, acceptable protocols to administer the composition including the route of administration and the effective amount of the composition to be administered to a subject can be determined by those skilled in the art. The composition of the present invention can be administered in vivo or ex vivo. Suitable in vivo routes of administration can include, but are not limited to, aerosol, oral, nasal, inhaled, topical, intratracheal, transdermal, rectal, or parenteral routes. Preferred parenteral routes can include, but are not limited to, subcutaneous, intradermal, intravenous, intramuscular, or intraperitoneal routes.

According to the present invention, Pim1 kinase inhibitors are able to induce expression of Runx3. These inhibitors also reduce expression of $CD4^+$ and $CD8^+$ T cell proliferation and have the ability to suppress Th2 differentiation and/or Th17 differentiation. The administration of a Pim1 kinase inhibitor prevents the development of AHR, airway inflammation and BAL cytokine production in subjects (for example mice) sensitized and challenged to allergen and attenuates the consequences of secondary challenges in previously sensitized and challenged subjects. These suppressive effects are manifested on both CD4+ and CD8+ T cells.

In one embodiment, the method of treating an allergic condition can comprise administering a composition comprising a compound that interacts with a regulator of Runx3 expression (mRNA or protein expression). Examples of a regulator include but are not limited to a Pim kinase. Other examples include transcriptional factors and regulators such as CxCL12 (chemokine (C—X—C motif) ligand 12), core binding factor-beta (CBFbeta, also known as polyomavirus enhancer binding protein 2 beta and is known to form a heterodimer with Runx1), transducin-like enhancer protein 1 (TLE1, a transcriptional co-repressor that is known to bind Runx1 and Runx3), interleukin-7 (IL-7), signal transducer and activator of transcription 5A (Stat 5), ETS-1, interferon regulatory factor 4 (IRF-4; known to be important in the regulation of interferons in response to infection by viruses and is also lymphocyte specific and negatively regulates Toll-like receptor (TLR) signaling that is central to the activation of innate and adaptive immune responses) or demethylating agents. In a preferred embodiment, the composition inhibits the activity of a compound such as Pim kinase and IRF4. Pim kinases include but are not limited to Pim1 kinase, Pim2 kinase, Pim3 kinase or a combination. In a preferred embodiment, the Pim kinase is Pim1 kinase. In another aspect, the compound is an antibody including but not limited to anti-CxCL12, anti-CBFbeta, anti-TLE1, anti-IL-7, anti-Stat 5, anti-ETS-1 or anti-IRF-4.

In another embodiment, the regulator that is capable of inducing Runx3 expression of the present invention may be a Pim kinase inhibitor. The Pim kinase inhibitor includes but is not limited to Pim1 kinase inhibitor, Pim2 kinase inhibitor or Pim3 kinase inhibitor. In a preferred embodiment, the Pim kinase inhibitor is a Pim1 kinase inhibitor. Examples of Pim kinase inhibitors include but are not limited to AR460770 (also referred to as AR00460770, ARRY 770 and AR770; ARRAY Biopharma), AR440 (ARRAY Biopharma), SimI4A, staurosporine, bisindolylmaleimide or triazolopyridine Pim kinase inhibitor compounds.

In still another embodiment of the present invention, the composition comprises an regulator that is an activator that increases expression of Runx3. The activators include but are not limited to G proteins, phosphatidylinositol-3 kinase (PI3K), JAK kinases, Rho GTPases or focal adhesion-associated proteins.

According to the methods of the present invention, an effective amount of a composition to administer to a subject comprises an amount that is capable of inhibiting expression and/or activity of Pim1 kinase and/or inducing Runx3 expression (mRNA and/or protein) without being toxic to the subject. An amount that is toxic to a subject comprises any amount that causes damage to the structure or function of a subject (i.e., poisonous).

In addition, according to the present invention, the composition can comprise a pharmaceutically acceptable excipient. According to the present invention, the composition, may be administered with a pharmaceutically acceptable carrier, which includes pharmaceutically acceptable excipients and/or delivery vehicles, for delivering the agent to a subject (e.g., a liposome delivery vehicle). As used herein, a pharmaceutically acceptable carrier refers to any substance suitable for delivering a therapeutic composition useful in the method of the present invention to a suitable in vivo or ex vivo site. Preferred pharmaceutically acceptable carriers are capable of maintaining the composition of the present invention in a form that, upon arrival of the composition to a target cell, the composition is capable of entering the cell and inhibiting Pim1 kinase and/or inducing Runx3 expression (mRNA and/or protein) in the cell. Suitable excipients of the present invention include excipients or formularies that transport or help transport, but do not specifically target a nucleic acid molecule to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

According to the methods of the present invention, the subject can be any animal subject, and particularly, in any vertebrate mammal, including, but not limited to, primates, rodents, livestock or domestic pets. Preferred mammals for the methods of the present invention include humans.

Another embodiment of the present invention, the present invention is directed toward a method to treat an allergic condition in a subject who has or is at risk of having an allergic disease, comprising administering to the subject a composition that inhibits Pim1 kinase, wherein the allergic condition is not a pulmonary condition. In one aspect, the allergic condition can be a food allergy, eosinophilic esophagitis, chronic urticaria, atopic dermatitis, occupational allergy, allergic conjunctivitis, airborne allergic sensitivities, stinging insect allergy, inflammatory bowel disease, ulcerative colitis, Crohn's disease or drug allergies. In another aspect, the food allergy is a peanut allergy. In yet another aspect, the subject has been sensitized to an allergen and has been exposed to, or is at risk of being exposed to, the allergen. In one aspect, the allergen is selected from a food, a plant, a gas, a pathogen, a metal, a glue or a drug. In another aspect, the composition comprises a compound selected from a small molecule inhibitor, an antibody, a chemical entity, a nucleotide, a peptide or a protein. In one aspect, the small molecule inhibitor can be a Pim kinase inhibitor selected from a Pim1 kinase inhibitor, a Pim2 kinase inhibitor and a Pim3 kinase inhibitor. In a preferred aspect, the Pim kinase inhibitor is a Pim1 kinase inhibitor. In still another aspect the Pim1 kinase inhibitor is selected from AA460770, AR440, SimI4A, staurosporine, bisindolylmaleimide or triazolopyridine Pim kinase inhibitor compounds. In one aspect, the Pim1 kinase inhibitor induces expression of Runx3. In another aspect, the Pim1 kinase inhibitor reduces CD4+ and CD8+ proliferation. In yet another aspect, the Pim1 kinase inhibitor suppresses Th2 differentiation. In still another aspect, the Pim1 kinase inhibitor suppresses Th17 differentiation.

In yet another embodiment, the present invention is directed toward a method to treat an allergic condition in a subject who has or is at risk of having an allergic disease, comprising administering to the subject a composition that induces expression of Runx3, wherein the composition does not comprise a Pim kinase inhibitor. In one aspect the composition interacts with a regulator of Runx3 expression. In another aspect, the regulator of Runx3 expression is selected from CxCL12, core binding factor-beta, transducin-like enhancer protein 1, IL-7, Stat 5, ETS-1, and IRF-4. In still another aspect, the composition inhibits the activity of IRF-4. In yet another aspect the composition comprises an IRF-4 inhibitor. In another aspect, the allergic condition can be allergic rhinitis, asthma, airway hyperresponsiveness, a food allergy, eosinophilic esophagitis, chronic urticaria, atopic dermatitis, occupational allergy, allergic conjunctivitis, hay fever, airborne allergic sensitivities, stinging insect allergy, hypersensitivity pneumonitis, eosinophilic lung diseases, inflammatory bowel disease, ulcerative colitis, Crohn's disease and drug allergies. In another aspect, the subject has been sensitized to an allergen and has been exposed to, or is at risk of being exposed to, the allergen. In one aspect, the allergen is selected from a food, a plant, a gas, a pathogen, a metal, a glue or a drug.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Materials and Methods for Examples 1-7 Described Below

Mice: Five- to 6-week-old female wild-type (WT) BALB/cByJ mice were purchased from the Jackson Laboratory (Bar Harbor, Me.).

Preparation of peanut protein: Crude peanut extract (PE) was prepared from defatted raw flours (Golden Peanut Company, Alpharetta, Ga.) as previously described (Wang, M., et al. 2010. J. Allergy Clin. Immunol. 126:306-316).

Figure 1A:
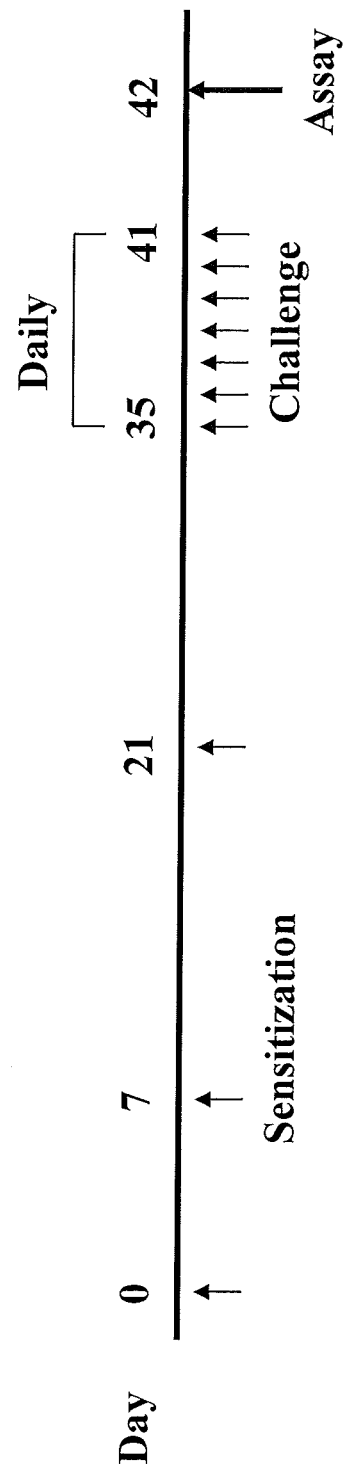
FIGS. 1A-1E shows data that Pim1 kinase is expressed in the mouse small intestine.

Sensitization and intragastric challenge: The experimental protocol for sensitization and challenge to peanut as described (Wang, M., et al. 2010. J. Allergy Clin. Immunol. 126:306-316) (FIG. 1A).

Assessment of hypersensitivity reactions: Anaphylactic symptoms were evaluated 30 minutes after the oral challenge, as reported (Li, X. M., et al. 2000. J. Allergy Clin. Immunol. 106:150-158). Scoring of symptoms was performed in a blinded manner by an independent observer.

Histology: The jejunum was fixed in 10% formalin, embedded in paraffin, and cut into 5-μm sections for immunohistochemical analysis.

Cytokines levels in tissue and cell culture: The preparation of intestine homogenates and analyses were performed as described (Wang, M., et al. 2010. J. Allergy Clin. Immunol. 126:306-316).

Measurement of peanut-specific antibody: Serum peanut-specific IgE, IgG1, and IgG2a levels were measured by ELISA, as described (Li, X. M., et al. 2000. J. Allergy Clin. Immunol. 106:150-158).

Histamine levels in plasma: Levels of histamine in plasma were measured using an enzyme immunoassay histamine kit (Beckman Coulter, Fullerton, Calif.), as described by the manufacturer. The concentration of histamine was calculated from a standard curve provided by the manufacturer.

T-cell differentiation and treatment with the Pim1 kinase inhibitor in vitro: Differentiation of Th1, Th2, or Th17 cells were performed as described (Komine, O., et al. 2003. J. Exp. Med. 198:51-61; Ashino, S., et al. 2010. Intl Immunol. 22:503-513).

Western blot analysis: Proteins were prepared from jejunal tissue and cultured cells were lysed as described (Wang, M., et al. 2010. J. Allergy Clin. Immunol. 126:306-316; Ohnishi, H., et al. 2008. J. Allergy Clin Immunol. 121:864-871).

Quantitative real-time PCR: RNA was extracted from jejunal tissue homogenates or from CD4 T cells cultured in vitro using Trizol (Invitrogen) according to the manufacturer's protocol. cDNA was generated using the iScript cDNA synthesis kit (Bio-Rad Laboratories, Hercules, Calif.). Quantitative real-time PCR was performed on the ABI Prism 7300 sequence detection system (Applied Biosystems, Foster City, Calif.). Primers and probes for murine IL4, IL6, IL13, IL17A, IFNg, Pim1, Pim2, Pim3, Runx1, Runx3, CBFβ, T-bet, ROG (repressor of Gata3), GATA3, NFATc1, RORγt, and GAPDH were purchased as Taqman Gene Expression Assays from Applied Biosystems. Fold change was calculated using the Delta Delta cycle threshold ($\Delta\Delta C_T$) method.

Intracellular cytokine staining and flow cytometry: Cells from MLN or differentiated CD4 T cells were labeled with anti-CD3 and anti-CD4 antibodies (eBiosciences). For intracellular staining, MLN cells or differentiated CD4 T cells were stimulated with 5 ng/ml PMA and 500 ng/ml ionomycin (Sigma-Aldrich) for 6 hrs in the presence of 10 mg/ml brefeldin A (Sigma-Aldrich). Following staining for cell surface markers, cells were fixed with 4% paraformaldehyde in PBS, permeabilized with 0.1% saponin, and stained for intracytoplasmic IL-4, IL-13, IL-17A, and IFN-γ using antibodies from BD Biosciences. Stained cells were analyzed on FACSCalibur (BD Biosciences) using CellQuest software (BD Biosciences).

Cell proliferation: Th1-, Th2-, or Th17-polarized CD4 T cells were incubated with anti-CD3 and anti-CD28 (eBioscience) at 37° C. for 24 hrs. To monitor the degree of cell proliferation, $^3$H-thymidine (PerkinElmer, Boston, Mass.) was added to the cultures for another 6 hrs prior to harvesting the cells and incorporation was measured in a liquid scintillation counter (Packard Bioscience Company, Meriden, Conn.).

Cell viability and apoptosis: Cell viability was determined using trypan blue exclusion assay. Cell apoptosis was detected by flow cytometry using surface staining with 7AAD and annexin V (BD Biosciences).

Statistical analysis: ANOVA was used to determine the levels of difference between all groups. Comparisons for all pairs utilized the Tukey Kramer highest significance difference test. P values for significance were set at 0.05. All results were expressed as the mean±SEM.

Example 1

This example shows that Pim1 kinase is upregulated in the small intestine of peanut sensitized and challenged mice.

Figure 1B:
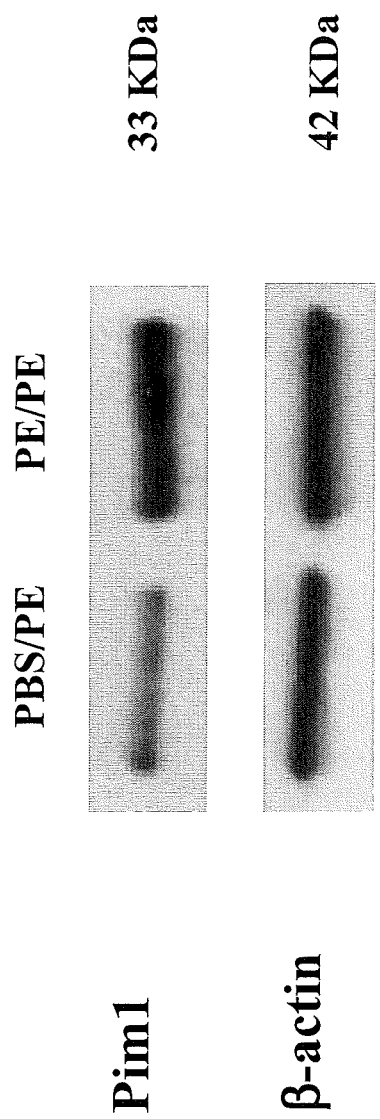
Figure 1C:
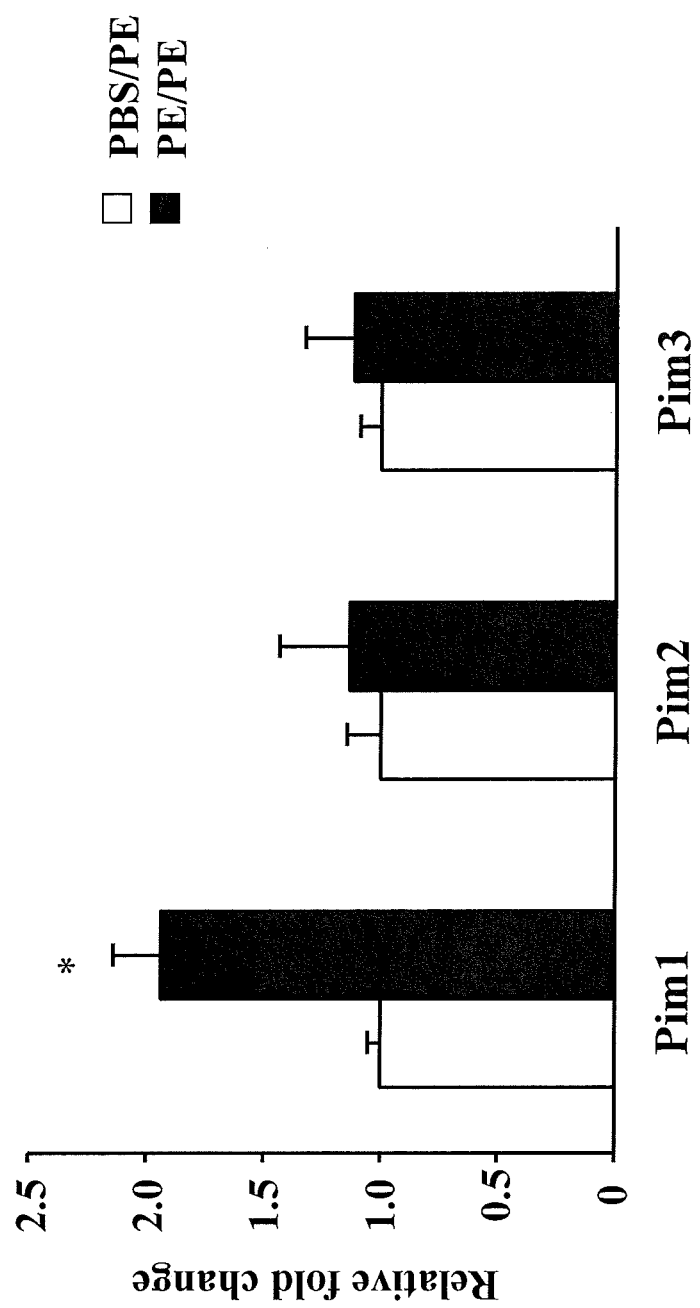
Figure 1D:
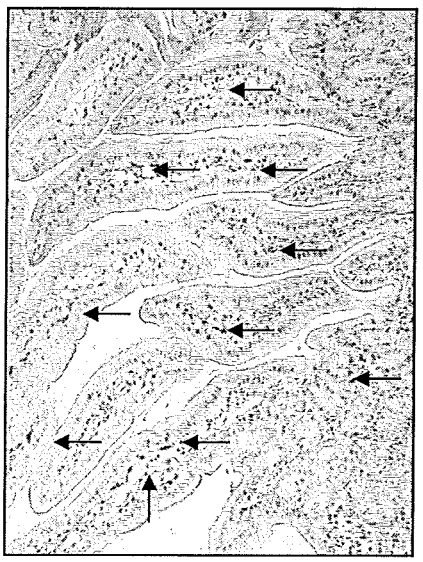
Figure 1D:
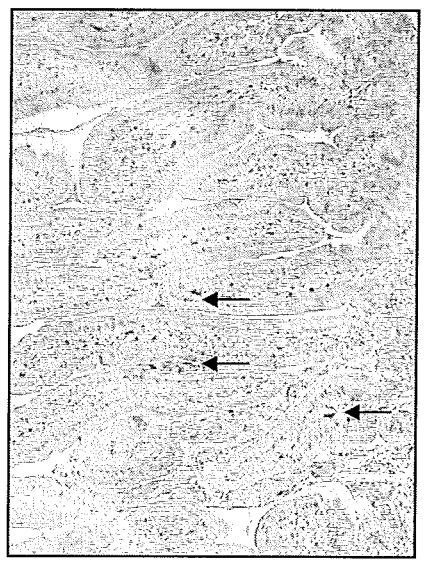
Figure 1D:
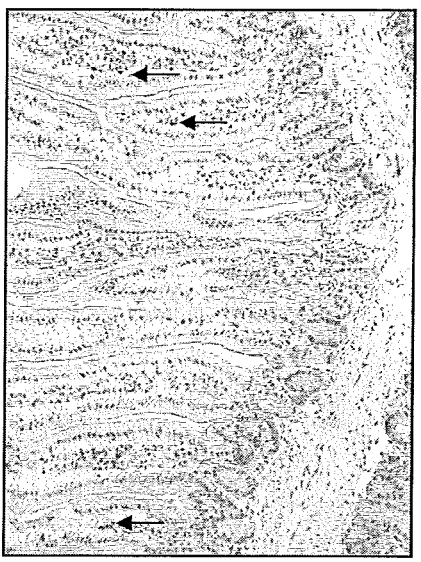
Figure 1D:
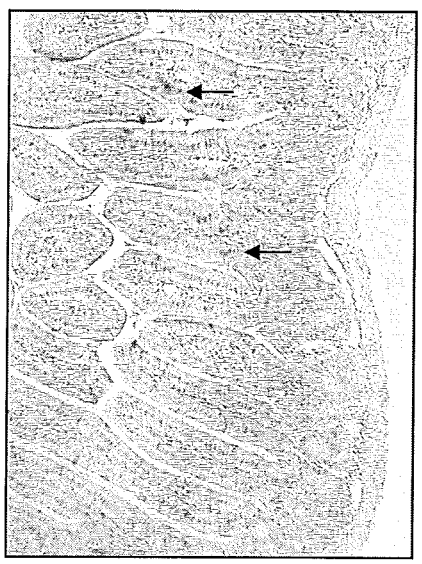
Figure 1E:
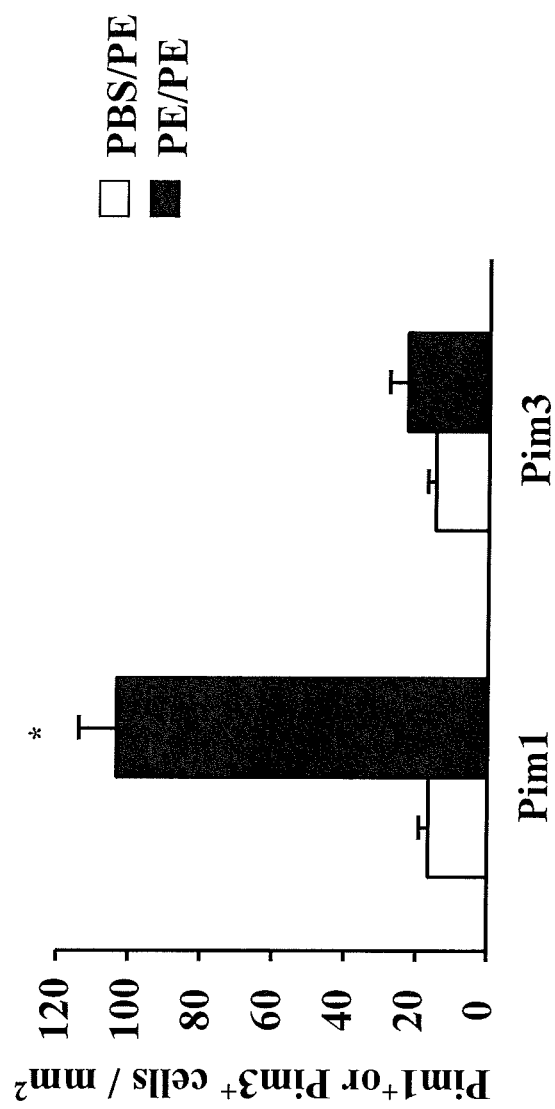

Pim1 kinase protein expression was increased in the jejunum of PE sensitized and challenged mice (FIG. 1B). Pim1 kinase mRNA levels were 2-fold higher in the jejunum of PE sensitized and challenged mice (FIG. 1C); Pim2 and Pim3 mRNA levels were not altered following sensitization and challenge. Pim1 was expressed predominantly in the lamina propria of jejunal tissues of sensitized and challenged mice and the numbers of positive cells were increased by approximately 5-fold in PE sensitized and challenged mice (FIGS. 1D, 1E). The numbers of Pim3-positive cells were lower with little alteration following PE sensitization and challenge.

Example 2

This example shows that Runx3 is downregulated in the small intestine of peanut sensitized and challenged mice.

Figure 2A:
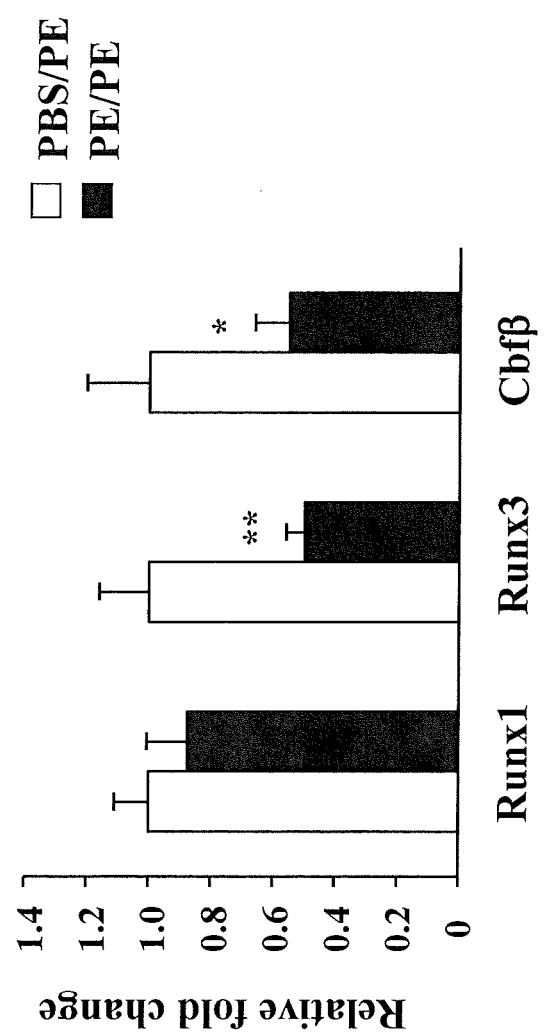
Figure 2C:
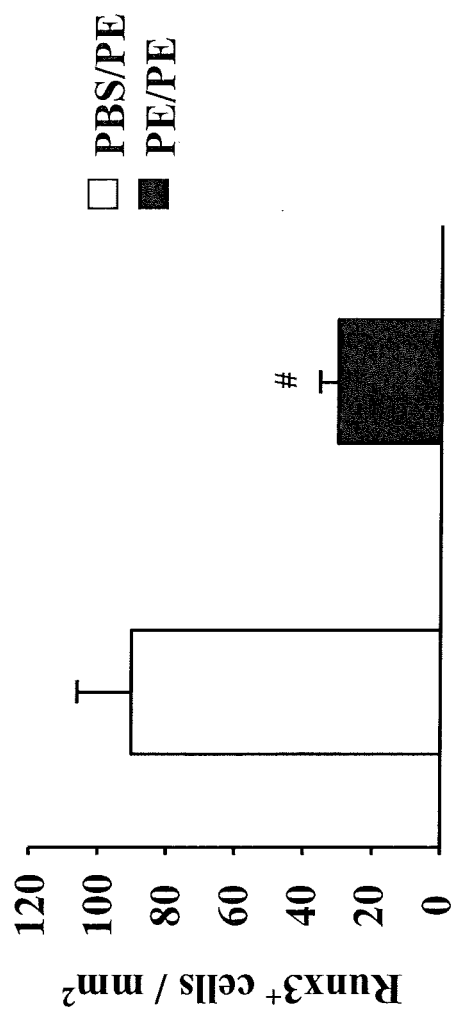

Runx3 associates with Pim1 and catalytically active Pim1 kinase regulates the transcriptional activity of Runx3 (Aho, T. L., et al. 2006. BMC Cell Biol. 7:21-29). Runx3 and Runx/ core binding factor β (Cbfβ) mRNA levels were decreased in the small intestine of PE sensitized and challenged mice. The levels of Runx3 and Cbfβ mRNA but not Runx1 were approximately 2-fold lower in the jejunum of PE sensitized and challenged mice compared to control mice (FIG. 2A). In parallel, Runx3 protein expression was also decreased in the jejunum of PE sensitized and challenged mice (FIG. 2B). Immunohistochemical analysis of jejunal tissues revealed that Runx3 protein was mainly expressed in the lamina propria and levels of expression were decreased by 3-fold in PE sensitized and challenged mice (FIG. 2C).

Example 3

This example demonstrates inhibition of Pim1 kinase can attenuate PE-induced intestinal responses in vivo.

Based on the data showing increased levels of Pim1 mRNA and protein in the jejunum after peanut sensitization and challenge in wild-type (WT) mice, it was thought that Pim1 plays an essential role in the development of intestinal allergy. Whether inhibition of Pim1 kinase alters the severity of PE-induced intestinal allergy using the small molecule inhibitor, AR460770 was determined. Sensitized mice were given the inhibitor twice daily by mouth during the 7 days of PE challenge. AR460770 administration resulted in a dose-dependent inhibitory effect on peanut-induced intestinal allergy induction; 30-100 mg/kg AR460770 prevented development of diarrhea and symptoms in PE sensitized and challenged mice (FIGS. 3A, 3B).

As mast cells were shown to be involved in the response to PE sensitization and challenge (Wang, M., et al. 2010. J. Allergy Clin. Immunol. 126:306-316), mast cell degranulation by quantitating plasma levels of histamine within 30 minutes of the last challenge were monitored. Levels of histamine in AR460770 (30 and 100 mg/kg)-treated mice were significantly decreased following sensitization and challenge (FIG. 3C).

When administered after sensitization and during challenge, the inhibitor had no effect on peanut-specific antibody production as shown by unaltered levels of serum peanut-specific IgE, IgG1, and IgG2a.

AR460770 inhibited mast cell and eosinophil accumulation and goblet cell metaplasia in the small intestinal tissues in a dose-dependent manner. PE sensitized and challenged mice treated with AR460770 at a dose of 30-100 mg/kg demonstrated markedly reduced numbers of mast cells, eosinophils, and PAS+ goblet cells in the mucosa of the small intestine. The small intestine lamina propria in the sham sensitized group contained few CD4 and CD8 T cells. These numbers were significantly increased in the untreated PE sensitized and challenged group and reduced to baseline levels in the treated (100 mg/kg) group (FIG. 3G).

Collectively, these results show that Pim1 kinase activation plays an essential role in enhancing allergic diarrhea, intestinal inflammation, and goblet cell metaplasia.

Example 4

This example shows that Pim1 kinase can regulate IL-13 and IL-17 production.

In addition to Th2 cells, Th17 cells have been implicated in allergic disease (Tesmer, L. A., et al. 2008. Immunol. Rev 223:87-113; Kolls J. K., et al. 2004. Immunity 21:467-476; Lajoie, S., et al. 2010. Nat Immunol. 11:928-935). The effect of Pim1 kinase inhibition in vivo on Th2 and Th17 cytokine levels were examined. After 7 days of PE challenges, intestinal tissue from sensitized mice demonstrated significant increases in IL4, IL6, IL13, and IL17A but not IFNG mRNA expression (FIG. 4A). After treatment with AR460770, mRNA expression levels for these cytokines returned to control levels. The levels of the key transcription factors regulating differentiation were also assessed. The expression levels of GATA3, NFATc1, and RORγt mRNA were also significantly increased in PE sensitized and challenged mice while IFNG, T-bet, and ROG mRNA levels were not altered (FIG. 4B). Following treatment with the inhibitor, these increased levels also returned to control levels.

To assess the impact of Pim1 kinase inhibition on T lymphocyte cytokine production, MLN CD4 T cells were isolated from mice treated with the inhibitor or vehicle and stimulated them with anti-CD3/anti-CD28. PE sensitization and challenge resulted in significant increases in the numbers of IL-4-, IL-13- and IL-17A-producing CD4 T cells (FIG. 4C). Mice treated with the inhibitor exhibited a 2-4-fold decrease in the numbers of these CD4 cytokine-producing cells. The percentages of $CD4^+IFN-\gamma^+$ cells were not altered by sensitization and challenge or treatment with the inhibitor.

Example 5

This example demonstrates that Pim1 can regulate Runx3 transcription factor expression.

In view of reports that Runx3 plays a critical role in the T cell response to antigen (Collins, A., et al. 2009. Nat. Rev. Immunol. 9:106-115) and has been linked to Pim1 kinase activation (Aho, T. L., et al. 2006. BMC Cell Biol. 7:21-29), inhibition of Pim1 kinase affecting Runx3 expression was determined. Protein was extracted from jejunal tissues and western blot analysis showed a decrease in levels of Runx3 in PE sensitized and challenged mice (FIG. 5A). In mice treated with AR460770, the levels of Runx3 were restored to baseline levels. In parallel, levels of Runx3 and Cbfβ mRNA were also decreased in the PE sensitized and challenged mouse tissue and these levels were restored to control values following treatment with the inhibitor (FIGS. 5B and 5D). Runx3 protein expression was decreased in the jejunum of PE sensitized and challenged mice but was similarly restored after treatment with the inhibitor (FIG. 5C). Taken together, these data indicated that PE sensitization and challenge resulted in Pim1 activation and Runx3 inhibition and the latter could be reversed by inhibition of Pim1.

In addition, Pim1 mRNA and protein levels were increased in the jejunum following peanut sensitization and challenge whereas the levels of Runx3 mRNA and protein were significantly decreased. Administration of the Pim1 kinase inhibitor (AR770) reduced the incidence of diarrhea in a dose-dependent manner. In parallel, mast cell and eosinophil accumulation and goblet cell metaplasia in the small intestinal tissues were markedly decreased. Mesenteric lymph node and small intestine Th2 and Th17 cytokine production were also significantly decreased. In contrast, mice treated with the Pim1 kinase inhibitor (AR770) had increased levels of Runx3 mRNA and protein in the small intestine. In vitro, the Pim1 kinase inhibitor repressed Th2 and Th17 but not Th1 cell differentiation and proliferation in a dose-dependent manner and enhanced Runx3 expression in Th2 cell differentiation.

Example 6

This example demonstrates the effects of Pim1 kinase inhibition on Th1, Th2 and Th17 cell differentiation and Runx3 expression in vitro.

Considering the effects of AR460770 on Runx3 and Th2/Th17 cytokine production in vivo, the effect of Pim1 kinase inhibition on Runx3 expression and T cell differentiation and function in vitro was determined. Isolated naive $CD4^+$ $CD45RB^+$ T cells were cultured under Th1, Th2, and Th17 polarizing conditions in the presence or absence of the inhibitor for 6 days and then stimulated with the combination of anti-CD3/anti-CD28. The Pim1 kinase inhibitor suppressed Th2 and Th17 cell expansion in a dose-dependent manner; 0.1-1 µM AR460770 inhibited cell number increases (FIG. 6A) and Th2 and Th17 cell proliferation assessed by $^3$H-thymidine incorporation (FIG. 6B); Th1 cell expansion was not significantly affected. In parallel, the levels of Th2 and Th17 cytokines in the polarized T cell cultures (IL-4, IL-13, and IL-17A, respectively) were decreased in the presence of 1 µM AR460770 (FIG. 6C); levels of IFN-γ were not affected by the inhibitor. These effects were not due to altered cell viability.

In the polarized T cell cultures the effects of AR460770 on the expression of Runx3 and lineage-specific transcription factors was determined by quantitative RT-PCR. In polarized Th2 cultures treated with the inhibitor, Runx3 mRNA expression was upregulated compared to vehicle treatment (FIG. 6D). Runx3 protein levels were also increased in polarized Th2 cells (FIG. 6E). Similar results were seen in Th17 polarized cells. In parallel, levels of IL13 and GATA3, and IL17A and RORγt mRNA expression were also decreased in Th2 and Th17 cells, respectively (FIG. 6D). No effects were detected in Th1 cells. These data demonstrated that inhibition of Pim1 kinase impacts Th2 and Th17 but not Th1 differentiation and promoted expression of Runx3. Thus, Pim1 kinase functions as a positive regulator for Th2 and Th17 differentiation and expansion and as a negative regulator of Runx3 expression.

Example 7

This example demonstrates a Pim1 kinase inhibitor and treatment in vivo.

To determine the role of Pim1 kinase in the development of allergen-induced AHR and airway inflammation, a small molecule Pim1 kinase inhibitor, AR460770 (ARRAY Biopharma, Boulder, Colo.) was used. The inhibitor was tested at 10 mM against 230 kinases in enzymatic assays (Millipore Kinase Profiler, Millipore, Billerica, Mass.) and shown to be selective for the three PIM isoforms (Table 1). Cellular $IC_{50}$ for Pim kinase inhibition were determined by assessing Ser112 phosphorylation of transiently infected Bad in HEK 293 cells engineered to express Pim1, Pim2 or Pim3 (Fainaru, O., et al. 2005. Proc. Natl. Acad. Sci. USA 102:10598-10603) (Table 2). Sensitized mice were administered the inhibitor twice daily by mouth (1-100 mg/kg) or vehicle (50 mM citric buffer, pH 4.0) during the 7 days of PE challenge. To determine the concentration of AR460770 achieved at the doses used, a satellite group of mice were dosed in a similar fashion and on day 30 plasma was collected 2 hrs after the last dose (peak level). Compound levels were determined to be 17, 124, 180, and 1100 nM at doses of 1, 10, 30, and 100 mg/kg, respectively (data not shown). Based on the cellular activity of AR460770 (Table 2), Pim1 inhibition should be attained at all but the 1-10 mg/kg dose, inhibition of Pim3 would be achieved only at the 100 mg/kg dose and there should be no inhibition of Pim2 at any dose tested.

TABLE 1

Characterization of PIM inhibitor AR00460770

| Kinase | | Enzyme $IC_{50}$ (nm) |
|---|---|---|
| Pim-1 | Proto-oncogene serine/threonine-protein kinase | 0.300 |
| Pim-2 | | 71 |
| Pim-3 | | 4 |
| PASK | proline-alanine-rich STE20-related kinase | 62 |
| TNK2 | tyrosine kinase, non-receptor2 | 3000 |
| CAMK2γ | $Ca^{2+}$/calmodulin-dependent protein kinase II gamma | 6000 |
| Flt3 | fms-like tyrosine kinase receptor-3 | >10000 |
| PDGFR | Platelet-derived growth factor receptors | >10000 |
| MARK1 | MAP/microtubule affinity-regulating kinase 1 | >10000 |
| CAMK2β | $Ca^{2+}$/calmodulin-dependent protein kinase II beta | >10000 |
| AMPK | 5'AMP-activated protein kinase | >10000 |
| RSK | ribosomal s6 kinase | >10000 |

AR00460770 was tested at 10 µM against 230 kinases in enzymatic assays (Millipore KinaseProfiler). It was determined to be selective for the 3 PIM isoforms.

TABLE 2

Cellular IC50s for PIM Inhibition

| | PIM1 | PIM2 | PIM3 |
|---|---|---|---|
| AR00460770 | 93 | 9200 | 340 |

Cellular $IC_{50}$s for PIM inhibition were determined for AR00460770 by assessing Ser112 phosphorylation of transiently transfected BAD in HEK cell lines engineered to express PIM1, PIM2 or PIM3. Cellular $IC_{50}$s in nM are shown.

Materials and Methods for Examples 8-12 Below

Animals: Female BALB/c mice, 8-12 weeks of age and free of pathogens were purchased from The Harlan Laboratory (Indianapolis, Ind.). The animals were maintained on an OVA-free diet. Experiments were conducted under a protocol approved by the Institutional Animal Care and Use Committee of National Jewish Health. Sensitization and challenge with allergen: The experimental protocol for sensitization and primary and secondary challenge to allergen utilized described procedures (Takeda, K., et al. 2005. Eur. Respir. J. 26:577-585). Briefly, in the primary allergen challenge protocol, mice were sensitized by intraperitoneal (ip) injection of 20 µg of OVA (Fisher Scientific, Pittsburgh, Pa.) emulsified in 2.0 mg alum (AlumImuject: Pierce, Rockford, Ill.) on days 1 and 14 followed by aerosolized OVA challenge (1% in saline for 20 minutes) on days 28, 29, and 30. The control mice were sensitized with PBS followed by OVA challenge in the same way. In the secondary allergen challenge protocol, mice were sensitized with 10 µg of OVA with alum on days 1 and 7 followed by 0.2% OVA challenge on days 14 to 16 (primary allergen challenge). Fourteen days after the last primary allergen challenge, mice were challenged again with 1% OVA for 20 minutes (secondary allergen challenge). A group of mice were sensitized with PBS followed by primary and secondary challenge with OVA. In all groups, assays were carried out 48 hrs after the last allergen challenge.

Pim kinase inhibitor treatment: To determine the role of Pim1 kinase in the development of allergen-induced AHR and airway inflammation, the Pim1 kinase inhibitor, AR00460770 (ARRAY Biopharma, Boulder, Colo.). To characterize AR00460770 in vitro, the cellular half maximal inhibitory concentration ($IC_{50}$) and kinase selectivity assays were determined. Cellular $IC_{50}$ of AR00460770 was analyzed by Ser112 phosphorylation of transiently transfected BAD in HEK-293 cell lines engineered to express human Pim1 and Pim2 (Millipore, Billerica, Mass.) and rat Pim3 (Array BioPharma, Boulder, Colo.) in conjunction with a DNA vector construct directing the expression of the Pim kinase substrate GST-BAD (pEBG-mBAD). Cells were treated with serial dilutions of AR00460770 for 1.5 hrs and then labeled with an antibody specific for phospho-BAD (Ser112) and an antibody against GST (Cell Signaling Technology, Danvers, Mass.) as a normalization control. Immunoreactivity was detected using IR fluorophore-conjugated secondary antibodies and quantified on the imager (Aerius, LI-COR, Lincoln, Nebr.). The kinase selectivity of AR00460770 was evaluated using the KinaseProfiler service (Millipore) (Lopez-Ramos, M., et al. 2010. FASEB J. 24:3171-3185; Yan Bin, et al. 2003. J. Biol. Chem. 278:45358-45367; Fox, C. J., et al. 2003. Genes Dev. 17:1841-1854). The properties and specificity of the inhibitor are described in Tables 1 and 2.

Western blot analysis: Lung tissues were homogenized, lysates cleared of debris and resuspended in an equal volume of 2× Lamelli buffer. Lysates were loaded onto a 4-10% gradient reducing gel, subjected to electrophoresis, and transferred to nitrocellulose membranes. The membranes were blotted with goat anti-Pim1 (Santa Cruz, Santa Cruz, Calif.) and rabbit anti-GAPDH (R&D Systems, Minneapolis, Minn.), anti-goat IgG (Invitrogen, Carlsbad, Calif.) and anti-rabbit IgG (Rockland, Gilbertson, Pa.). Images were captured and quantitatively analyzed using the Odyssey infrared imager (Li-cor, Lincoln, Nebr.). Assessment of airway function: Airway responsiveness was assessed as previously described by measuring changes in airway resistance in response to increasing doses of inhaled methacholine (MCh, Sigma-Aldrich, St. Louis, Mo.) in anesthetized and ventilated mice (Takeda, K., et al. 1997. J. Exp. Med. 186:449-454). The values of peak airway responses to inhaled MCh were recorded.

Bronchoalveolar lavage (BAL) and lung histology: Lungs were lavaged with 1 ml of Hanks balanced salt solution through the trachea immediately after assessment of AHR. Numbers of total leukocyte were counted with a hemocytometer and cell differentiation was performed on the cytospin slides prepared with Wright-Giemsa stain. The numbers of inflammatory and mucus-containing cells were quantitated as described (Tomkinson, A., et al. 2001. Am J. Respir. Crit. Care Med. 163:721-730).

Measurement of cytokines: Cytokine levels in the BAL fluid and cell culture supernatants were measured by ELISA as described (Tomkinson, A., et al. 2001. Am J. Respir. Crit. Care Med. 163:721-730).

Isolation of lung mononuclear cells (MNCs) and flow cytometry: Lung MNCs were isolated as described previously using collagenase digestion and cell composition identified as described (Oshiba, A., et al. 1996. J. Clin Invest. 97:1398-1408).

$CD4^+$ and $CD8^+$ T cell purification and cell proliferation assay: Purification of $CD4^+$ and $CD8^+$ T cells was conducted as described (Miyahara, N., et al. 2004. J. Immunol. 172: 2549-2558). Purity of $CD4^+$ and $CD8^+$ T cell populations exceeded 95% as assessed by flow cytometry.

In cell proliferation assays, an anti-mouse CD3e mAb (5 µg/mL; R&D Systems, Minneapolis, Minn.) was immobilized on 96-well flat-bottom plates overnight at 4° C. Purified $CD4^+$ and $CD8^+$ T cells incubated with inhibitor or PBS as vehicle, ($2\times10^5$ cells/well) and anti-CD28 mAb (5 µg/mL, R&D Systems) were added to the anti-CD3-precoated plates and incubated at 37° C. for 24 hrs. After 24 hrs, 1 µCi tritium-labeled thymidine per well (PerkinElmer, Boston, Mass.) was added to 96-well plates for 6 hrs and harvested with distilled water followed by counting in a microplate scintillation and luminescence counter (Packard, Meriden, Conn.). Cell viability of $CD4^+$ and $CD8^+$ T cells was assessed 24 hrs after incubation with 10 µM of inhibitor by a vital stain with trypan blue and determined using an automated cell counter (Countess, Invitrogen, Carlsbad, Calif.).

Statistical analysis: Results were expressed as the mean±SEM. The t test was used to determine differences between the two groups. For comparisons between multiple groups, the Tukey-Kramer test was used. Nonparametric analysis using the Mann-Whitney U test or Kruskal-Wallis test was also used to confirm that the statistical differences remained significant even if the underlying distribution was uncertain. Differences were regarded as statistically significant when the p-value was lower than 0.05.

Example 8

This example demonstrates that lung Pim1 kinase levels can be increased after sensitization and challenge with allergen.

To determine the importance of Pim1 kinase following allergen challenge, protein expression levels of Pim1 kinase in lung tissue after OVA challenge of sensitized mice was determined. Pim1 expression levels in OVA sensitized mice were markedly increased following OVA challenge compared with levels seen in non-sensitized, challenged only mice. This upregulation was detected in OVA sensitized mice 6 hrs after the second OVA challenge, and remained high up to 24 hrs after the third OVA challenge (FIGS. 7A and 7B).

Example 9

This example shows Pim1 kinase inhibitor treatment can prevent development of AHR and airway inflammation following primary allergen challenge.

Figure 8B:
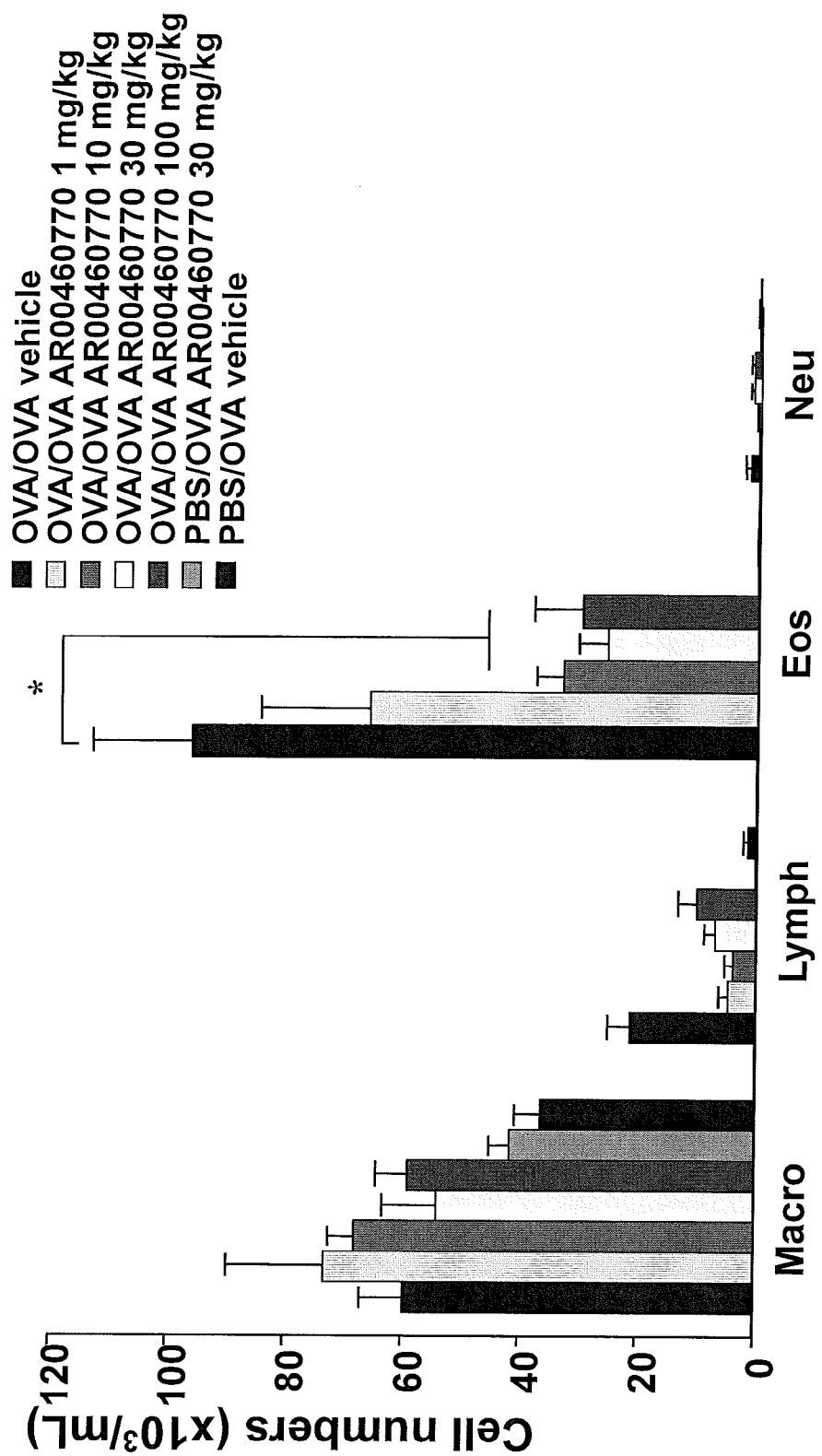

To determine the effect of Pim1 kinase inhibitor treatment on allergen-induced airway inflammation and AHR, mice were treated with the inhibitor or vehicle during the OVA challenge phase in the primary allergen challenge model. As shown in FIGS. 8A and 8B, vehicle-treated mice developed higher airway responses to MCh and eosinophil numbers in BAL fluid following sensitization and challenge with OVA compared to sham-sensitized, OVA challenged mice. Mice treated with the Pim1 inhibitor at doses of 10, 30, or 100 mg/kg developed significantly lower airway responsiveness to inhaled MCh and lower BAL eosinophil numbers compared to the vehicle-treated group. Sham-sensitized but OVA challenged mice were treated with 100 mg/kg of the inhibitor to assess potential effects on smooth muscle contraction. Treatment with the inhibitor in this way did not alter the development of increasing RL to increasing concentrations of inhaled MCh.

Figure 8C:
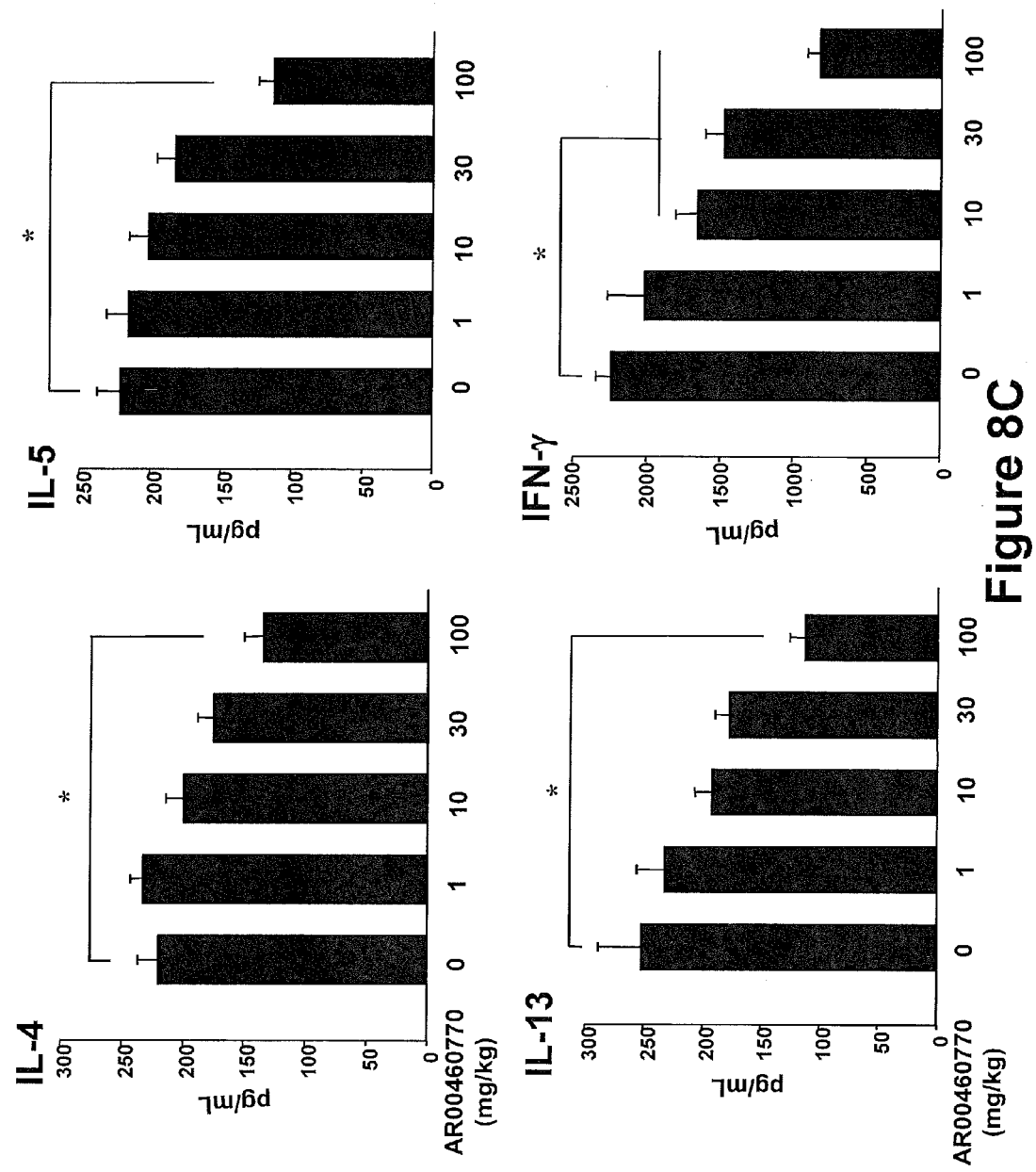

As shown in FIG. 8C, inhibitor treatment of sensitized and challenged mice reduced the levels of IL-4, IL-5, IL-13, and IFN-γ in BAL fluid in a dose-dependent manner with significant changes seen primarily at the highest administered dose of the inhibitor (100 mg/kg).

Histopathological analysis of lung tissue sections revealed that the numbers of inflammatory cells, including eosinophils in the peribronchial and perivascular areas, were increased in mice after OVA sensitization and challenge compared to sham-sensitized and challenged mice (FIG. 8D). Similarly, the numbers of PAS$^+$ mucus-containing goblet cells were increased in the sensitized and challenged mice (FIG. 8E). Administration of the inhibitor significantly decreased the numbers of inflammatory cells and PAS$^+$ mucus-containing goblet cells in the lung tissues in a dose-dependent manner (FIG. 8E).

Example 10

This example shows inhibition of Pim1 kinase can attenuate development of AHR and airway inflammation in the secondary allergen challenge model.

Figure 9B:
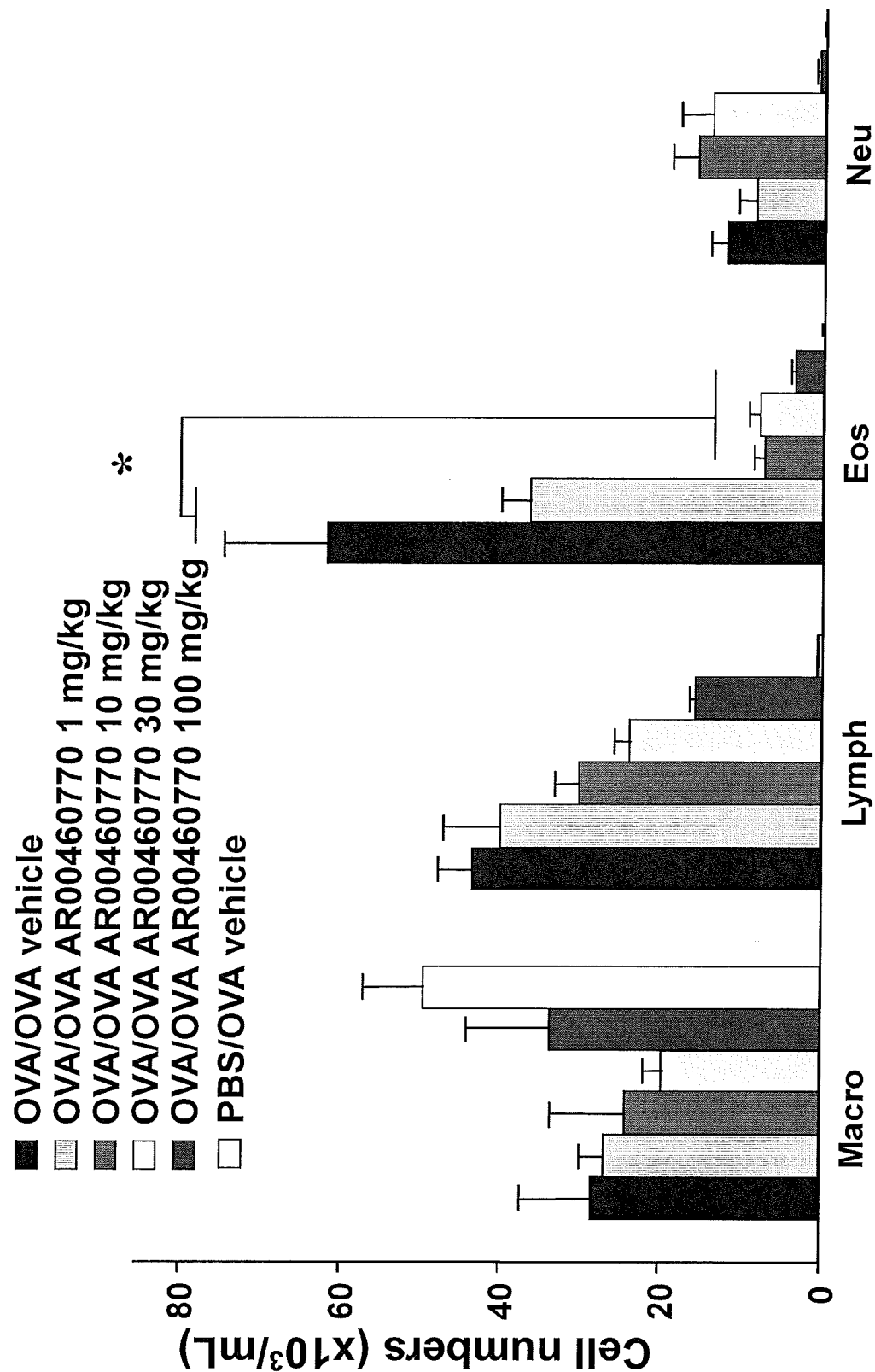
Figure 9C:
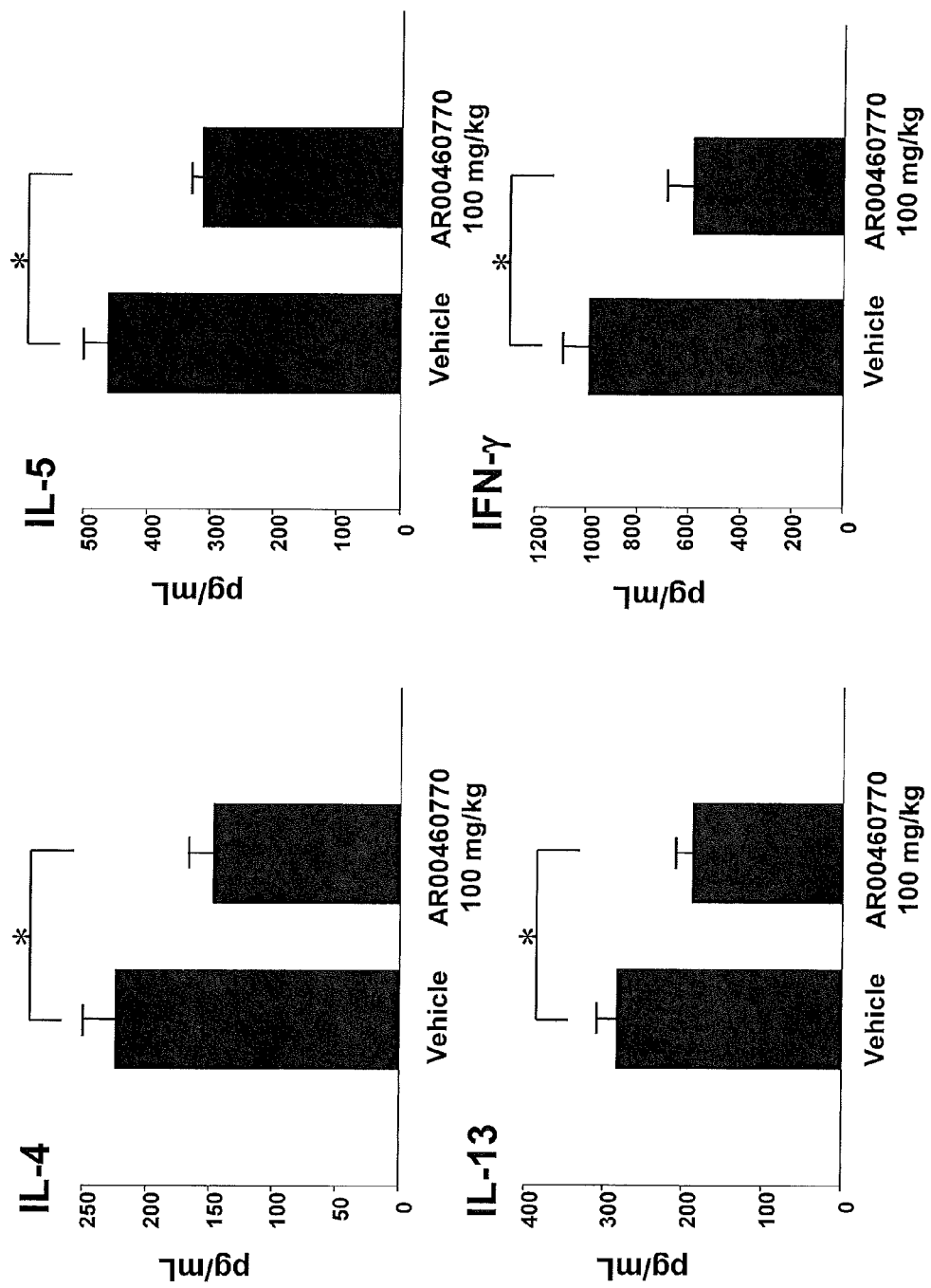

The airway responses in the primary allergen challenge model reflect the first immune responses in the lungs, where adaptive immunity is initiated in response to airborne allergen exposure. For the most part, asthmatics have already developed allergic airway inflammation and airway dysfunction prior to initiation of treatment; immune responses to allergen and tissue remodeling of the airways are generally already established. The secondary allergen challenge model is an approach to examine the response to allergen provocation where allergen-induced airway inflammation has been previously established. To determine the effects of Pim1 kinase inhibition in the secondary allergen challenge model, AHR, cell composition, and cytokine levels in BAL fluid was measured 48 hrs after a single provocative allergen challenge. As in the primary allergen challenge model, vehicle-treated mice developed significantly higher airway responsiveness to MCh and eosinophils in BAL fluid following OVA sensitization and secondary allergen challenge. Similar to the results observed in the primary allergen challenge model, treatment with the Pim1 kinase inhibitor (10, 30, and 100 mg/kg) significantly decreased levels of airway responsiveness and the number of eosinophils in BAL fluid in a dose-dependent manner compared to the vehicle-treated groups (FIGS. 9A and 9B). Assays of BAL cytokine levels demonstrated that IL-4, IL-5, IL-13, and IFN-g were decreased in Pim1 kinase inhibitor (100 mg/kg)-treated mice that had been sensitized and challenged with OVA (FIG. 9C). Histopathological analysis revealed that Pim1 kinase inhibition decreased numbers of inflammatory cell in the lungs and goblet cell metaplasia along the airways (FIG. 9D).

Example 11

This example demonstrates that a decrease of CD4$^+$ and CD8$^+$ T cells in the lungs of sensitized and challenged mice follows treatment with the Pim1 kinase inhibitor.

As both CD4$^+$ and CD8$^+$ T cells are potent effector cells in the development of allergic inflammation, their numbers were examined after inhibitor treatment in sensitized and challenged mice. Lungs from OVA sensitized and challenged mice which received either inhibitor or vehicle were excised and lung MNCs were purified. Numbers of CD4$^+$ and CD8$^+$ T cells were determined by flow cytometry. As shown in FIG. 10, the overall number of CD4$^+$ T cells was significantly lower in the inhibitor-treated mice (1.48±0.26×10$^6$ cells/lung vs. 3.09±0.35×10$^6$ cells/lung in vehicle-treated mice). CD8$^+$ T cells were also decreased following Pim1 kinase inhibition from 0.57±0.21×10$^6$ cells/lung to 0.29±0.06×10$^6$ cells/lung. These results demonstrate that Pim1 kinase inhibition in vivo reduces the numbers of CD4$^+$ and CD8$^+$ T cells that accumulate in the lungs of sensitized and challenged mice.

Example 12

This example shows a reduction of CD4$^+$ and CD8$^+$ T cell proliferation and cytokine production in vitro following Pim1 kinase inhibitor treatment can occur.

To examine the proliferative capacity of T cells following inhibition of Pim 1 kinase, CD4 and CD8 T cells were isolated and purified from spleen and incubated with a combination of anti-CD3 and anti-CD28 for 24 hrs. Cell viabilities of CD4$^+$ or CD8$^+$ T cells were determined in the presence of 10 mM of the inhibitor. After 24 hrs, inhibitor treatment did not show significant effects on cell viabilities compared to vehicle control (from 90.0 to 90.3% in CD4+ T cells and from 80.2-82.8% in CD8+ T cells, respectively). In a dose-dependent manner, the Pim1 kinase inhibitor reduced CD4$^+$ and CD8$^+$ T cell proliferation triggered by the combination of anti-CD3/anti-CD28. In stimulated cell cultures, increased levels of IL-4, IL-5, IL-13, and IFN-g were detected. Treatment with the inhibitor decreased the levels of all of these cytokines in a dose-dependent fashion (FIGS. 11A, 11B and 11C).

The foregoing description of the present invention has been presented for purposes of illustration. The description is not intended to limit the invention to the form disclosed herein. Consequently, variations and modifications commensurate with the above teachings, and the skill or knowledge of the relevant art, are within the scope of the present invention. The embodiments described hereinabove are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Each publication and reference cited herein is incorporated herein by reference in its entirety.

REFERENCES

1. Gavett, S. H., X. Chen, F. Finkelman, and M. Wills-Karp. 1994. Depletion of murine CD4+ T lymphocytes prevents antigen-induced airway hyperreactivity and pulmonary eosinophilia. *Am J Respir Cell Mol Biol* 10:587-593.
2. Umetsu, D. T., J. J. McIntire, O. Akbari, C. Macaubas, and R. H. DeKruyff. 2002. Asthma: an epidemic of dysregulated immunity. *Nat Immunol* 3:715-720.
3. Hogan, S. P., K. I. Matthaei, J. M. Young, A. Koskinen, I. G. Young, and P. S. Foster. 1998. A novel T cell-regulated mechanism modulating allergen-induced airways hyperreactivity in BALB/c mice independently of IL-4 and IL-5. *J Immunol* 161:1501-1509.
4. Wills-Karp, M., J. Luyimbazi, X. Xu, B. Schofield, T. Y. Neben, C. L. Karp, and D. D. Donaldson. 1998. Interleukin-13: central mediator of allergic asthma. *Science* 282:2258-2261.
5. Robinson, D. S., Q. Hamid, S. Ying, A. Tsicopoulos, J. Barkans, A. M. Bentley, C. Corrigan, S. R. Durham, and A. B. Kay. 1992. Predominant TH2-like bronchoalveolar T-lymphocyte population in atopic asthma. *N Engl J Med* 326:298-304.

6. Aaronson, D. S., and C. M. Horvath. 2002. A road map for those who don't know JAK-STAT. *Science* 296:1653-1655.
7. Bachmann, M., and T. Moroy. 2005. The serine/threonine kinase Pim-1. *Int J Biochem Cell Biol* 37:726-730.
8. Wang, Z., N. Bhattacharya, M. Weaver, K. Petersen, M. Meyer, L. Gapter, and N. S. Magnuson. 2001. Pim-1: a serine/threonine kinase with a role in cell survival, proliferation, differentiation and tumorigenesis. *J Vet Sci* 2:167-179.
9. Amaravadi, R., and C. B. Thompson. 2005. The survival kinases Akt and Pim as potential pharmacological targets. *J Clin Invest* 115:2618-2624.
10. Fox, C. J., P. S. Hammerman, and C. B. Thompson. 2005. The Pim kinases control rapamycin-resistant T cell survival and activation. *J Exp Med* 201:259-266.
11. Amson, R., F. Sigaux, S. Przedborski, G. Flandrin, D. Givol, and A. Telerman. 1989. The human protooncogene product p33pim is expressed during fetal hematopoiesis and in diverse leukemias. *Proc Natl Acad Sci USA* 86:8857-8861.
12. Valdman, A., X. Fang, S. T. Pang, P. Ekman, and L. Egevad. 2004. Pim-1 expression in prostatic intraepithelial neoplasia and human prostate cancer. *Prostate* 60:367-371.
13. Cibull, T. L., T. D. Jones, L. Li, J. N. Eble, L. Ann Baldridge, S. R. Malott, Y. Luo, and L. Cheng. 2006. Overexpression of Pim-1 during progression of prostatic adenocarcinoma. *J Clin Pathol* 59:285-288.
14. Nieborowska-Skorska, M., G. Hoser, P. Kossev, M. A. Wasik, and T. Skorski. 2002. Complementary functions of the antiapoptotic protein A1 and serine/threonine kinase pim-1 in the BCR/ABL-mediated leukemogenesis. *Blood* 99:4531-4539.
15. Temple, R., E. Allen, J. Fordham, S. Phipps, H. C. Schneider, K. Lindauer, I. Hayes, J. Lockey, K. Pollock, and R. Jupp. 2001. Microarray analysis of eosinophils reveals a number of candidate survival and apoptosis genes. *Am J Respir Cell Mol Biol* 25:425-433.
16. Andina, N., S. Didichenko, J. Schmidt-Mende, C. A. Dahinden, and H. U. Simon. 2009. Proviral integration site for Moloney murine leukemia virus 1, but not phosphatidylinositol-3 kinase, is essential in the antiapoptotic signaling cascade initiated by IL-5 in eosinophils. *J Allergy Clin Immunol* 123:603-611.
17. Stout, B. A., M. E. Bates, L. Y. Liu, N. N. Farrington, and P. J. Bertics. 2004. IL-5 and granulocyte-macrophage colony-stimulating factor activate STAT3 and STAT5 and promote Pim-1 and cyclin D3 protein expression in human eosinophils. *J Immunol* 173:6409-6417.
18. Busse, W. W., R. L. Coffman, E. W. Gelfand, A. B. Kay, and L. J. Rosenwasser. 1995. Mechanisms of persistent airway inflammation in asthma. A role for T cells and T-cell products. *Am J Respir Crit Care Med* 152:388-393.
19. Cohn, L., R. J. Horner, A. Marinov, J. Rankin, and K. Bottomly. 1997. Induction of airway mucus production By T helper 2 (Th2) cells: a critical role for interleukin 4 in cell recruitment but not mucus production. *J Exp Med* 186:1737-1747.
20. Hogan, S. P., A. Koskinen, K. I. Matthaei, I. G. Young, and P. S. Foster. 1998. Interleukin-5-producing CD4+ T cells play a pivotal role in aeroallergen-induced eosinophilia, bronchial hyperreactivity, and lung damage in mice. *Am J Respir Crit Care Med* 157:210-218.
21. Azzawi, M., B. Bradley, P. K. Jeffery, A. J. Frew, A. J. Wardlaw, G. Knowles, B. Assoufi, J. V. Collins, S. Durham, and A. B. Kay. 1990. Identification of activated T lymphocytes and eosinophils in bronchial biopsies in stable atopic asthma. *Am Rev Respir Dis* 142:1407-1413.
22. Hamelmann, E., A. Oshiba, J. Paluh, K. Bradley, J. Loader, T. A. Potter, G. L. Larsen, and E. W. Gelfand. 1996. Requirement for CD8+ T cells in the development of airway hyperresponsiveness in a marine model of airway sensitization. *J Exp Med* 183:1719-1729.
23. Isogai, S., R. Taha, M. Tamaoka, Y. Yoshizawa, Q. Hamid, and J. G. Martin. 2004. CD8+ alphabeta T cells can mediate late airway responses and airway eosinophilia in rats. *J Allergy Clin Immunol* 114:1345-1352.
24. Miyahara, N., K. Takeda, T. Kodama, A. Joetham, C. Taube, J. W. Park, S. Miyahara, A. Balhorn, A. Dakhama, and E. W. Gelfand. 2004. Contribution of antigen-primed CD8+ T cells to the development of airway hyperresponsiveness and inflammation is associated with IL-13. *J Immunol* 172:2549-2558.
25. Miyahara, N., B. J. Swanson, K. Takeda, C. Taube, S. Miyahara, T. Kodama, A. Dakhama, V. L. Ott, and E. W. Gelfand. 2004. Effector CD8+ T cells mediate inflammation and airway hyper-responsiveness. *Nat Med* 10:865-869.
26. Croft, M., L. Carter, S. L. Swain, and R. W. Dutton. 1994. Generation of polarized antigen-specific CD8 effector populations: reciprocal action of interleukin (IL)-4 and IL-12 in promoting type 2 versus type 1 cytokine profiles. *J Exp Med* 180:1715-1728.
27. Seder, R. A., J. L. Boulay, F. Finkelman, S. Barbier, S. Z. Ben-Sasson, G. Le Gros, and W. E. Paul. 1992. CD8+ T cells can be primed in vitro to produce IL-4. *J Immunol* 148:1652-1656.
28. Coyle, A. J., F. Erard, C. Bertrand, S. Walti, H. Pircher, and G. Le Gros. 1995. Virus-specific CD8+ cells can switch to interleukin 5 production and induce airway eosinophilia. *J Exp Med* 181:1229-1233.
29. Takeda, K., N. Miyahara, T. Kodama, C. Taube, A. Balhorn, A. Dakhama, K. Kitamura, A. Hirano, M. Tanimoto, and E. W. Gelfand. 2005. S-carboxymethylcysteine normalises airway responsiveness in sensitised and challenged mice. *Eur Respir J* 26:577-585.
30. Takeda, K., E. Hamelmann, A. Joetham, L. D. Shultz, G. L. Larsen, C. G. Irvin, and E. W. Gelfand. 1997. Development of eosinophilic airway inflammation and airway hyperresponsiveness in mast cell-deficient mice. *J Exp Med* 186:449-454.
31. Tomkinson, A., G. Cieslewicz, C. Duez, K. A. Larson, J. J. Lee, and E. W. Gelfand. 2001. Temporal association between airway hyperresponsiveness and airway eosinophilia in ovalbumin-sensitized mice. *Am J Respir Crit Care Med* 163:721-730.
32. Oshiba, A., E. Hamelmann, K. Takeda, K. L. Bradley, J. E. Loader, G. L. Larsen, and E. W. Gelfand. 1996. Passive transfer of immediate hypersensitivity and airway hyperresponsiveness by allergen-specific immunoglobulin (Ig) E and IgG1 in mice. *J Clin Invest* 97:1398-1408.
33. Cheng, J. Q., A. K. Godwin, A. Bellacosa, T. Taguchi, T. F. Franke, T. C. Hamilton, P. N. Tsichlis, and J. R. Testa. 1992. AKT2, a putative oncogene encoding a member of a subfamily of protein-serine/threonine kinases, is amplified in human ovarian carcinomas. *Proc Natl Acad Sci USA* 89:9267-9271.
34. Bellacosa, A., D. de Feo, A. K. Godwin, D. W. Bell, J. Q. Cheng, D. A. Altomare, M. Wan, L. Dubeau, G. Scambia, V. Masciullo, G. Fernandina, P. Benedetti Panici, S. Mancuso, G. Neri, and J. R. Testa. 1995. Molecular alterations of the AKT2 oncogene in ovarian and breast carcinomas. *Int J Cancer* 64:280-285.

35. Stahl, J. M., A. Sharma, M. Cheung, M. Zimmerman, J. Q. Cheng, M. W. Bosenberg, M. Kester, L. Sandirasegarane, and G. P. Robertson. 2004. Deregulated Akt3 activity promotes development of malignant melanoma. *Cancer Res* 64:7002-7010.

36. Masure, S., B. Haefner, J. J. Wesselink, E. Hoefnagel, E. Mortier, P. Verhasselt, A. Tuytelaars, R. Gordon, and A. Richardson. 1999. Molecular cloning, expression and characterization of the human serine/threonine kinase Akt-3. *Eur J Biochem* 265:353-360.

37. Yang, L., H. C. Dan, M. Sun, Q. Liu, X. M. Sun, R. I. Feldman, A. D. Hamilton, M. Polokoff, S. V. Nicosia, M. Herlyn, S. M. Sebti, and J. Q. Cheng. 2004. Akt/protein kinase B signaling inhibitor-2, a selective small molecule inhibitor of Akt signaling with antitumor activity in cancer cells overexpressing Akt. *Cancer Res* 64:4394-4399.

38. Kondapaka, S. B., S. S. Singh, G. P. Dasmahapatra, E. A. Sausville, and K. K. Roy. 2003. Perifosine, a novel alkylphospholipid, inhibits protein kinase B activation. *Mol Cancer Ther* 2:1093-1103.

39. van Lohuizen, M., S. Verbeek, P. Krimpenfort, J. Domen, C. Saris, T. Radaszkiewicz, and A. Berns. 1989. Predisposition to lymphomagenesis in pim-1 transgenic mice: cooperation with c-myc and N-myc in murine leukemia virus-induced tumors. *Cell* 56:673-682.

40. Mikkers, H., M. Nawijn, J. Allen, C. Brouwers, E. Verhoeven, J. Jonkers, and A. Berns. 2004. Mice deficient for all PIM kinases display reduced body size and impaired responses to hematopoietic growth factors. *Mol Cell Biol* 24:6104-6115.

41. Katakami, N., H. Kaneto, H. Hao, Y. Umayahara, Y. Fujitani, K. Sakamoto, S. Gorogawa, T. Yasuda, D. Kawamori, Y. Kajimoto, M. Matsuhisa, C. Yutani, M. Hori, and Y. Yamasaki. 2004. Role of pim-1 in smooth muscle cell proliferation. *J Biol Chem* 279:54742-54749.

42. Chen, L. S., S. Redkar, D. Bearss, W. G. Wierda, and V. Gandhi. 2009. Pim kinase inhibitor, SGI-1776, induces apoptosis in chronic lymphocytic leukemia cells. *Blood* 114:4150-4157.

43. Hu, X. F., J. Li, S. Vandervalk, Z. Wang, N. S. Magnuson, and P. X. Xing. 2009. PIM-1-specific mAb suppresses human and mouse tumor growth by decreasing PIM-1 levels, reducing Akt phosphorylation, and activating apoptosis. *J Clin Invest* 119:362-375.

44. Borgonovo, B., G. Casorati, E. Frittoli, D. Gaffi, E. Crimi, and S. E. Burastero. 1997. Recruitment of circulating allergen-specific T lymphocytes to the lung on allergen challenge in asthma. *J Allergy Clin Immunol* 100:669-678.

45. Yan, B., M. Zemskova, S. Holder, V. Chin, A. Kraft, P. J. Koskinen, and M. Lilly 2003. The PIM-2 kinase phosphorylates BAD on serine 112 and reverses BAD-induced cell death. *J Biol Chem* 278:45358-45367.

46. Chen, X. P., J. A. Losman, S. Cowan, E. Donahue, S. Fay, B. Q. Vuong, M. C. Nawijn, D. Capece, V. L. Cohan, and P. Rothman. 2002. Pim serine/threonine kinases regulate the stability of Socs-1 protein. *Proc Natl Acad Sci USA* 99:2175-2180.

47. Maita, H., Y. Harada, D. Nagakubo, H. Kitaura, M. Ikeda, K. Tamai, K. Takahashi, H. Ariga, and S. M. Iguchi-Ariga. 2000. PAP-1, a novel target protein of phosphorylation by pim-1 kinase. *Eur J Biochem* 267:5168-5178.

48. Koike, N., H. Maita, T. Taira, H. Ariga, and S. M. Iguchi-Ariga. 2000. Identification of heterochromatin protein 1 (HP1) as a phosphorylation target by Pim-1 kinase and the effect of phosphorylation on the transcriptional repression function of HP1(1). *FEBS Lett* 467:17-21.

49. Wang, Z., N. Bhattacharya, M. K. Meyer, H. Seimiya, T. Tsuruo, J. A. Tonani, and N. S. Magnuson. 2001. Pim-1 negatively regulates the activity of PTP-U2S phosphatase and influences terminal differentiation and apoptosis of monoblastoid leukemia cells. *Arch Biochem Biophys* 390:9-18.

50. Rainio, E. M., J. Sandholm, and P. J. Koskinen. 2002. Cutting edge: Transcriptional activity of NFATc1 is enhanced by the Pim-1 kinase. *J Immunol* 168:1524-1527.

51. Patra, A. K., T. Drewes, S. Engelmann, S. Chuvpilo, H. Kishi, T. Hunig, E. Serfling, and U. H. Bommhardt. 2006. PKB rescues calcineurin/NFAT-induced arrest of Rag expression and pre-T cell differentiation. *J Immunol* 177:4567-4576.

52. Busse, W. W., and R. F. Lemanske, Jr. 2001. Asthma. *N Engl J Med* 344:350-362.

53. Rosenberg, H. F., S. Phipps, and P. S. Foster. 2007. Eosinophil trafficking in allergy and asthma. *J Allergy Clin Immunol* 119:1303-1310; quiz 1311-1302.

54. Larche, M., D. S. Robinson, and A. B. Kay. 2003. The role of T lymphocytes in the pathogenesis of asthma. *J Allergy Clin Immunol* 111:450-463; quiz 464.

55. Mullarkey, M. F., B. A. Blumenstein, W. P. Andrade, G. A. Bailey, I. Olason, and C. E. Wetzel. 1988. Methotrexate in the treatment of corticosteroid-dependent asthma. A double-blind crossover study. *N Engl J Med* 318:603-607.

56. Alexander, A. G., N. C. Barnes, and A. B. Kay. 1992. Trial of cyclosporin in corticosteroid-dependent chronic severe asthma. *Lancet* 339:324-328.

57. Kweon M N, Yamamoto M, Kajiki M, Takahashi I, Kiyono H. Systemically derived large intestinal CD4 (+) Th2 cells play a central role in STATE-mediated allergic diarrhea. J Clin Invest 2000; 106:199-206

58. Wang M, Takeda K, Shiraishi Y, Okamoto M, Dakhama A, Joetham A, Gelfand E W. Peanut-Induced Intestinal Allergy is Mediated Through a Mast Cell-IgE-FcεRI-IL-13 Pathway. J. Allergy Clin Immunol 2010, 126 (2): 306-316

59. Knight A K, Blázquez A B, Zhang S, Mayer L, Sampson H A, Berin M C. CD4 T cells activated in the mesenteric lymph node mediate gastrointestinal food allergy in mice. Am J Physiol Gastrointest Liver Physiol. 2007; 293(6): G1234-43

60. Kweon M N, Yamamoto M, Kajiki M, Takahashi I, Kiyono H. Systemically derived large intestinal CD4(+) Th2 cells play a central role in STATE-mediated allergic diarrhea. J Clin Invest. 2000; 106(2): 199-206

61. Eigenmann P A. T lymphocytes in food allergy: overview of an intricate network of circulating and organ-resident cells. Pediatr Allergy Immunol 2002; 13:162-71.

62. Eigenmann P A, Huang S K, Ho D G, Sampson H A. Human T cell clones and cell lines specific to ovomucoid recognize different domains and consistently express IL-5. Adv Exp Med Biol 1996; 409:217

63. Blumchen K, Ulbricht H, Staden U, Dobberstein K, Beschorner J, de Oliveira L C, Shreffler W G, Sampson H A, Niggemann B, Wahn U, Beyer K. Oral peanut immunotherapy in children with peanut anaphylaxis. J Allergy Clin Immunol. 2010; 126(1):83-91

64. Kolls J K, Linden A. Interleukin-17 family members and inflammation. Immunity. 2004, 21:467-476

65. Ivanov I I, McKenzie B S, Zhou L, Tadokoro C E, Lepelley A, Lafaille J J, Cua D J, Littman D R. The orphan nuclear receptor RORgammat directs the differentiation program of proinflammatory IL-17+ T helper cells. Cell. 2006; 126(6): 1121-33.

66. Wang Z, Bhattacharya N, Weaver M, Petersen K, Meyer M, Gapter L, Magnuson N S. Pim-1: a serine/threonine kinase with a role in cell survival, proliferation, differentiation and tumorigenesis. J Vet Sci. 2001; 2(3):167-179
67. Aho T L, Sandholm J, Peltola K J, Ito Y, Koskinen P J. Pim-1 kinase phosphorylates RUNX family transcription factors and enhances their activity. BMC Cell Biol. 2006; 7:21-29
68. Rainio E M, Sandholm J, Koskinen P J. Transcriptional activity of NFATc1 is enhanced by the Pim-1 kinase. J Immunol. 2002; 168(4): 1524-7
69. Wingett D, Long A, Kelleher D, Magnuson N S. pim-1 proto-oncogene expression in anti-CD3-mediated T cell activation is associated with protein kinase C activation and is independent of Raf-1. J Immunol. 1996; 156(2):549-57.
70. Tesmer L A, Lundy S K, Sarkar S, Fox D A. Th17 cells in human disease. Immunol Rev. 2008, 223:87-113
71. Brenner O, Levanon D, Negreanu V, Golubkov O, Fainaru O, Woolf E, Groner Y. Loss of Runx3 function in leukocytes is associated with spontaneously developed colitis and gastric mucosal hyperplasia. Proc Natl Acad Sci USA. 2004; 101(45):16016-21
72. Fainaru O, Woolf E, Lotem J, Yarmus M, Brenner O, Goldenberg D, Negreanu V, Bernstein Y, Levanon D, Jung S, Groner Y. Runx3 regulates mouse TGF-beta-mediated dendritic cell function and its absence results in airway inflammation. EMBO J. 2004; 23(4): 969-79
73. Komine O, Hayashi K, Natsume W, Watanabe T, Seki Y, Seki N, Yagi R, Sukzuki W, Tamauchi H, Hozumi K, Habu S, Kubo M, Satake M. The Runx1 transcription factor inhibits the differentiation of naive CD4+ T cells into the Th2 lineage by repressing GATA3 expression. J Exp Med. 2003; 198 (1): 51-61
74. Nawijn M C, Alendar A, Berns A. For better or for worse: the role of Pim oncogenes in tumorigenesis. Nat Rev Cancer. 2011; 11:23-34.
75. Kicic A, Hallstrand T S, Sutanto E N, Stevens P T, Kobor M S, Taplin C, Paré P D, Beyer R P, Stick S M, Knight D A. Decreased fibronectin production significantly contributes to dysregulated repair of asthmatic epithelium. Am J Respir Crit Care Med. 2010; 181:889-98.
76. Lack G, Renz H, Saloga J, Bradley K L, Loader J E, Leung D Y M, Larsen G L, Gelfand E W. Nebulized but not parenteral IFN-decreases IgE production and normalizes airway function in a murine model of allergen sensitization. J Immunol 1994; 152:25446-25454.
77. Flaishon L, Topilaki I, Shoseyov D, Hershkoviz R, Fireman E, Levo Y, Marmor S, Shachar I. Anti-inflammatory properties of low levels of IFN-. J Immunol 2002; 168: 3707-3711.
78. Yoshida M, Leigh R, Matsumoto K, Wattie J, Ellis R, O'Byrne P M, Inman M D. Effect of interferon-on allergic airway responses in interferon-gamma-deficient mice. Amer J Resp Crit Care Med 2002; 166:451-456.
79. Hessel E M, Van Oosterhout A J, Van Ark I, Van Esch B, Hofman G, Van Loveren H, Savelkoul H F, Nijkamp F P. Development of airway hyperresponsiveness is dependent on interferon-gamma and independent of eosinophil infiltration. Amer J Resp Cell Molec Biol 1997; 16:325-334.
80. ten Hacken N H T, Oosterhoff Y, Kauffman H F, Guevarra L, Satoh T, Tollerud D J, Postma D S. Elevated serum interferon-γ in atopic asthma correlates with increased airways responsiveness and circadian peak expiratory flow variation. Eur Resp J 1998; 11:312-316.
81. Heaton T, Rowe J, Turner S, Aalberse R C, de Klerk N, Suriyaarachchi D, Serralha M, Holt B J, Hollams E, Yerkovich S, Holt K, Sly P D, Goldblatt J, Le Souef P, Holt P G. An immunoepidemiological approach to asthma: Identification of in-vitro T cell response patterns associated with different wheezing phenotypes in children. Lancet 2005; 365:142-149.
82. Lopez A F, Sanderson C J, Gamble J R, Campbell H D, Young I G, Vadas M A. Recombinant human interleukin 5 is a selective activator of human eosinophil function. J Exp Med 1988; 167:219-224.
83. Laoukili J, Perret E, Willems T, Minty A, Parthoens E, Houcine O, Coste A, Jorissen M, Marano F, Caput D, Tournier F. IL-13 alters mucociliary differentiation and ciliary beating of human respiratory epithelial cells. J Clin Invest 2001; 108:1817-1824.
84. Cohn L, Tepper J S, Bottomly K. IL-4-independent induction of airway hyperresponsiveness by Th2, but not Th1, cells. J Immunol 1998; 161:3813-3816.
85. Perrier C, Thierry A C, Mercenier A, Corthésy B. Allergen-specific antibody and cytokine responses, mast cell reactivity and intestinal permeability upon oral challenge of sensitized and tolerized mice. Clin Exp Allergy 2010; 40:153-162.
86. Taniuchi I, Osato M, Egawa T, Sunshine M J, Bae S C, Komori T, Ito Y, Littman D R. Differential requirements for Runx proteins in CD4 repression and epigenetic silencing during T lymphocyte development. Cell 2002; 111:621-633.
87. Cruz-Guilloty F, Pipkin M E, Djuretic I M, Levanon D, Lotem J, Lichtenheld M G, Groner Y, Rao A. Runx3 and T-box proteins cooperate to establish the transcriptional program of effector CTLs. *J Exp Med* 2009; 206:51-59.
88. Djuretic I M, Levanon D, Negreanu V, Groner Y, Rao A, Ansel K M. Transcription factors T-bet and Runx3 cooperate to activate IFN and silence IL4 in T helper type 1 cells. *Nat Immunol* 2007; 8:145-153.
89. Kohu K, Ohmori H, Wong W F, Onda D, Wakoh T, Kon S, Yamashita M, Nakayama T, Kubo M, Satake M. The Runx3 transcription factor augments Th1 and down-modulates Th2 phenotypes by interacting with and attenuating GATA3. *J Immunol* 2009; 183:7817-7824.
90. Lee S H, Jeong H M, Choi J M, Cho Y C, Kim T S, Lee K Y, Kang B Y. Runx3 inhibits IL-4 production in T cells via physical interaction with NFAT. *Biochem Biophys Res Commun* 2009; 381:214-217.
91. Aujla M. Targeted therapies: Pim kinase inhibition and chemoresistance. *Nat Rev Clin Oncol* 2010; 7:3.
92. Brault L, Gasser C, Bracher F, Huber K, Knapp S, Schwaller L. PIM serine/threonine kinases in the pathogenesis and therapy of hematologic malignancies and solid cancers. *Haematologica* 2010; 95:1004-1015.
93. Aho T L, Lund R J, Ylikoski E K, Matikainen S, Lahesmaa R, Koskinen P J. Expression of human pim family genes is selectively up-regulated by cytokines promoting T helper type 1, but not T helper type 2, cell differentiation. *Immunology* 2005; 116:82-88.
94. Dautry F, Weil D, Yu J, Dautry-Varsat A. Regulation of pim and myb mRNA accumulation by interleukin 2 and interleukin 3 in murine hematopoietic cell lines. *J Biol Chem* 1988; 263:17615-17620.
95. Lilly M, Le T, Holland P, Hendrickson S L. Sustained expression of the pim-1 kinase is specifically induced in myeloid cells by cytokines whose receptors are structurally related. *Oncogene* 1992; 7:727-732.
96. Matikainen S, Sareneva T, Ronni T, Lehtonen A, Koskinen P J, Julkunen I. Interferon-α activates multiple STAT proteins and up-regulates proliferation-associated IL-2Rα, c-myc, and pim-1 genes in human T cells. *Blood* 1999; 93:1980-1991.
97. Jackson L J, Wright D, Gross S, Robinson J, Marmsater F P, Allen S, Munson M, Carter L L. Inhibition of T cell function in vitro and in vivo using small molecule antagonists of PIM kinases. *J Immunol* 2009; 182:35.33.
98. Walter D M, McIntire J J, Berry G, McKenzie A N, Donaldson D D, DeKruyff R H, Umetsu D T. Critical role for IL-13 in the development of allergen induced airway hyperreactivity. *J Immunol* 2001; 167:4668-4675.
99. Miyahara S, Miyahara N, Matsubara S, Takeda K, Koya T, Gelfand E W. IL-13 is essential to the late-phase response in allergic rhinitis. *J Allergy Clin Immunol* 2006; 118: 1110-1116.
100. Donaldson D D, Whitters M J, Fitz L J, Neben T Y, Finnerty H, Henderson S L, O'Hara Jr R M, Beier D R, Turner K J, Wood C R, Collins M. The murine IL-13 receptor alpha 2: molecular cloning, characterization, and comparison with murine IL-13 receptor alpha 1. *J Immunol* 1998; 161:2317-2324.
101. Taube C, Miyahara N, Ott V, Swanson B, Takeda K, Loader J, Shultz L D, Tager A M, Luster A D, Dakhama A, Gelfand E W. The leukotriene B4 receptor (BLT1) is required for effector CD8+ T cell-mediated, mast cell-dependent airway hyperresponsiveness. *J Immunol* 2006; 176:3157-3164.
102. Wang Y H, Voo K S, Liu B, Chen C Y, Uygungil B, Spoede W, Bernstein J A, Huston D P, Liu Y J. A novel subset of CD4 (+) T(H)2 memory/effector cells that produce inflammatory IL-17 cytokine and promote the exacerbation of chronic allergic asthma. *J Exp Med* 2010; 207: 2479-2491.
103. Szabo S J, Kim S T, Costa G L, Zhang X, Fathman C G, Glimcher L H. A novel transcription factor, bet, directs Th1 lineage commitment. *Cell* 2000; 100:655-669.
104. Zhang D H, Cohn L, Ray P, Bottomly K, Ray A. Transcription factor GATA-3 is differentially expressed in murine Th1 and Th2 cells and controls Th2-specific expression of the interleukin-5 gene. *J Biol Chem* 1997; 272:21597-21603.
105. Zheng W, Flavell R A. The transcription factor GATA-3 is necessary and sufficient for Th2 cytokine gene expression in CD4 T cells. *Cell* 1997; 89:587-596.
106. Zhou L, Lopes J E, Chong M M, Ivanov I I, Min R, Victora G D, Shen Y, Du J, Rubtsov Y P, Rudensky A Y, Ziegler S F, Littman D R. TGF-beta-induced Foxp3 inhibits T(H)17 cell differentiation by antagonizing RORgammat function. *Nature* 2008; 453:236-240.
107. Okamoto K, Iwai Y, Oh-Hora M, Yamamoto M, Morio T, Aoki K, Ohya K, Jetten A M, Akira S, Muta T, Takayanagi H. IkappaBzeta regulates T(H)17 development by cooperating with ROR nuclear receptors. *Nature* 2010; 464:1381-1385.
108. Ichiyama K, Yoshida H, Wakabayashi Y, Chinen T, Saeki K, Nakaya M, Takaesu G, Hori S, Yoshimura A, Kobayashi T. Foxp3 inhibits RORgammat-mediated IL-17A mRNA transcription through direct interaction with RORgammat. *J Biol Chem* 2008; 283:17003-17008.
109. Zhou L, Ivanov I I, Spolski R, Min R, Shenderov K, Egawa T, Levy D E, Leonard W J, Littman D R. IL-6 programs T(H)-17 cell differentiation by promoting sequential engagement of the IL-21 and IL-23 pathways. *Nat Immunol* 2007; 8:967-974.
110. Li X M, Serebrisky D, Lee S Y, Huang C K, Bardina L, Schofield B H, Stanley J S, Burks A W, Bannon G A, Sampson H A. A murine model of peanut anaphylaxis: T- and B-cell responses to a major peanut allergen mimic human responses. *J Allergy Clin Immunol* 2000; 106:150-158.

What is claimed:
1. A method to treat an allergic condition in a subject who has or is at risk of having an allergic condition, comprising administering to the subject a composition comprising a Pim I kinase inhibitor that inhibits Pim1 kinase, wherein the allergic condition is a food allergy, and wherein the Pim I kinase inhibitor is AR460770.
2. The method of claim 1, wherein the food allergy is a peanut allergy.
3. The method of claim 1, wherein the subject has been sensitized to the food allergy and has been exposed to, or is at risk of being exposed to, the food allergy.
4. The method of claim 1, wherein administration of the Pim1 kinase inhibitor induces expression of Runx3.
5. The method of claim 1, wherein administration of the Pim1 kinase inhibitor reduces CD4$^+$ and CD8$^+$ cell proliferation.
6. The method of claim 1, wherein administration of the Pim1 kinase inhibitor suppresses Th2 differentiation.
7. The method of claim 1, wherein administration of the Pim1 kinase inhibitor suppresses Th17 differentiation.
8. The method of claim 1 wherein the composition is administered by a delivery method selected from the group consisting of aerosol delivery, parenteral delivery and oral delivery.

* * * * *